United States Patent
Aihara et al.

(10) Patent No.: US 9,120,773 B2
(45) Date of Patent: Sep. 1, 2015

(54) CYCLIC AZINE DERIVATIVES, PROCESSES FOR PRODUCING THESE, AND ORGANIC ELECTROLUMINESCENT ELEMENT CONTAINING THESE AS COMPONENT

(75) Inventors: Hidenori Aihara, Ayase (JP); Akitoshi Ogata, Ayase (JP); Yousuke Hisamatsu, Ayase (JP); Tsuyoshi Tanaka, Ayase (JP); Nobumichi Arai, Ayase (JP); Mayumi Abe, Ayase (JP); Yuichi Miyashita, Ayase (JP); Takashi Iida, Ayase (JP); Naoki Uchida, Ayase (JP)

(73) Assignees: TOSOH CORPORATION, Yamaguchi (JP); SAGAMI CHEMICAL RESEARCH INSTITUTE, Kanagawa (JP)

( * ) Notice: Subject to any disclaimer, the term of this patent is extended or adjusted under 35 U.S.C. 154(b) by 379 days.

(21) Appl. No.: 13/391,046

(22) PCT Filed: Aug. 20, 2010

(86) PCT No.: PCT/JP2010/064070
§ 371 (c)(1),
(2), (4) Date: May 7, 2012

(87) PCT Pub. No.: WO2011/021689
PCT Pub. Date: Feb. 24, 2011

(65) Prior Publication Data
US 2012/0214993 A1 Aug. 23, 2012

(30) Foreign Application Priority Data

Aug. 21, 2009 (JP) ................. 2009-192470
Sep. 15, 2009 (JP) ................. 2009-212853
Nov. 12, 2009 (JP) ................. 2009-259341
Dec. 21, 2009 (JP) ................. 2009-289752

(51) Int. Cl.
C07D 251/24 (2006.01)
C09K 11/06 (2006.01)
H01L 51/52 (2006.01)
H01L 51/54 (2006.01)
C07D 401/04 (2006.01)
C07D 401/10 (2006.01)
C07D 401/14 (2006.01)
C07D 403/04 (2006.01)
C07D 403/10 (2006.01)
C07D 403/14 (2006.01)
C07B 61/00 (2006.01)
C07D 239/26 (2006.01)
C07D 405/10 (2006.01)
C07D 417/10 (2006.01)
C07D 471/04 (2006.01)
H05B 33/10 (2006.01)
H01L 51/50 (2006.01)

(52) U.S. Cl.
CPC ............ *C07D 401/10* (2013.01); *C07D 239/26* (2013.01); *C07D 251/24* (2013.01); *C07D 403/10* (2013.01); *C07D 405/10* (2013.01); *C07D 417/10* (2013.01); *C07D 471/04* (2013.01); *C09K 11/06* (2013.01); *H05B 33/10* (2013.01); *C09K 2211/1007* (2013.01); *C09K 2211/1011* (2013.01); *C09K 2211/1029* (2013.01); *C09K 2211/1037* (2013.01); *C09K 2211/1044* (2013.01); *C09K 2211/1059* (2013.01); *C09K 2211/1088* (2013.01); *H01L 51/5012* (2013.01); *H01L 51/5072* (2013.01)

(58) Field of Classification Search
CPC .. C07D 251/24; C07D 401/04; C07D 401/10; C07D 401/14; C07D 403/04; C07D 403/10; C07D 403/14; C09K 11/06
USPC ................................. 544/180; 345/82, 72, 76
See application file for complete search history.

(56) References Cited

U.S. PATENT DOCUMENTS 6,656,608 B1 12/2003 Kita et al.
7,994,316 B2 * 8/2011 Yamakawa et al. ........... 544/180
(Continued)

FOREIGN PATENT DOCUMENTS

EP 1 962 354 A1 8/2008
EP 2 141 158 A1 1/2010
(Continued)

OTHER PUBLICATIONS

Tatsuo Ishiyama et al., "Palladium(0)-Catalyzed Cross-Coupling Reaction of Alkoxydiboron with Haloarenes: A Direct Procedure for Arylboronic Esters.", Journal of Organic Chemistry, vol. 60, No. 23., Jul. 10, 1995, pp. 7508-7510.
Miki Murata et al., "Palladium-Catalyzed Borylation of Aryl Hakides or Triflates with Dialkoxyborane: A Novel and Facile Synthetic Route to Arylboronates", Journal of Organic Chemistry, vol. 65, No. 1., 2000, pp. 164-168.
"International Search Report (ISR).", Application No. PCT/JP2010/064070, Date: Sep. 28, 2010, pp. 1-2.
Search report from E.P.O. in EP 14003201.2-1462, mail date is Nov. 27, 2014.

*Primary Examiner* — Venkataraman Balasubramanian
(74) *Attorney, Agent, or Firm* — Greenblum & Bernstein, P.L.C.

(57) ABSTRACT

A cyclic azine compound represented by general formula (1):

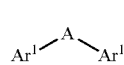

wherein each $Ar^1$ represents an aromatic group, which is unsubstituted or substituted by a $C_{1-4}$ alkyl group, a phenyl group or a pyridyl group; and A represents a group selected from those which are represented by general formulae (2) to (5), described in the description. The cyclic azine compound is useful for an organic compound layer of fluorescent or phosphorescent EL device.

10 Claims, 1 Drawing Sheet

(56) References Cited

U.S. PATENT DOCUMENTS

| | | |
|---|---|---|
| 8,268,997 B2 * | 9/2012 | Yamakawa et al. ............ 544/180 |
| 8,569,485 B2 * | 10/2013 | Yamakawa et al. ............ 544/180 |
| 8,674,091 B2 * | 3/2014 | Aihara et al. ................. 544/180 |
| 8,735,577 B2 * | 5/2014 | Aihara et al. ................. 544/180 |
| 2004/0058195 A1 | 3/2004 | Kita et al. |
| 2004/0062951 A1 | 4/2004 | Kita et al. |
| 2004/0072019 A1 | 4/2004 | Kita et al. |
| 2004/0096696 A1 | 5/2004 | Kita et al. |
| 2006/0025564 A1 | 2/2006 | Craig et al. |
| 2006/0154105 A1 | 7/2006 | Yamamoto et al. |
| 2007/0020485 A1 | 1/2007 | Kita et al. |
| 2007/0190355 A1 | 8/2007 | Ikeda et al. |
| 2008/0199726 A1 | 8/2008 | Schafer et al. |
| 2010/0249406 A1 | 9/2010 | Yamakawa et al. |
| 2011/0190494 A1 | 8/2011 | Aihara et al. |
| 2011/0288295 A1 | 11/2011 | Aihara et al. |

FOREIGN PATENT DOCUMENTS

| | | |
|---|---|---|
| EP | 2383323 | 11/2011 |
| JP | 2001-143869 A | 5/2001 |
| JP | 2003-45662 A | 2/2003 |
| JP | 2004-22334 | 1/2004 |
| JP | 2004-22334 A | 1/2004 |
| JP | 2004-31004 A | 1/2004 |
| JP | 2004-253298 | 9/2004 |
| JP | 2005-276801 | 10/2005 |
| JP | 2006-510732 A | 3/2006 |
| JP | 2004-2297 A | 1/2007 |
| JP | 2007-137829 | 6/2007 |
| JP | 2007-534722 | 11/2007 |
| JP | 2008-159741 | 7/2008 |
| JP | 2008-280330 A | 11/2008 |
| JP | 2009-021336 | 1/2009 |
| WO | 2004/039786 A1 | 5/2004 |
| WO | 2005/085387 A1 | 9/2005 |
| WO | 2005/105950 A1 | 11/2005 |
| WO | 2007/069569 A1 | 6/2007 |
| WO | 2008/129912 | 10/2008 |

* cited by examiner

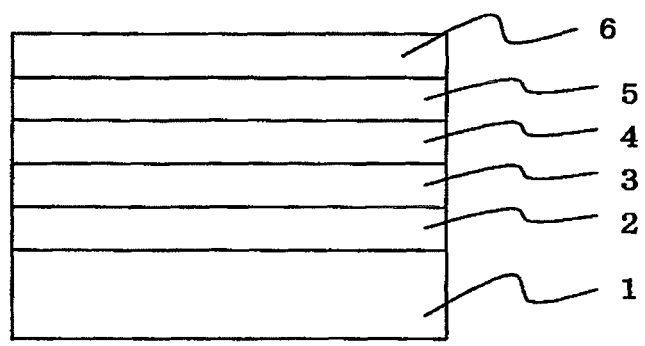

CYCLIC AZINE DERIVATIVES, PROCESSES FOR PRODUCING THESE, AND ORGANIC ELECTROLUMINESCENT ELEMENT CONTAINING THESE AS COMPONENT

TECHNICAL FIELD

This invention relates to cyclic azine compounds having two different substituents on an azine ring, and a process for producing the cyclic azine compounds.

The cyclic azine compounds exhibit good charge-transporting property, therefore, are useful as a component of a fluorescent or phosphorescent organic electroluminescent device.

Thus, this invention further relates to an organic electroluminescent device having at least one organic compound layer containing the cyclic azine derivative as a component, which is a highly efficient organic electroluminescent device exhibiting improved drivability and light emission.

BACKGROUND ART

An organic electroluminescent (hereinafter abbreviated to "EL" when appropriate) device has a multilayer structure comprising (i) a luminescent layer comprising a light emitting material and (ii) a hole transport layer and an electron transport layer, which sandwich the luminescent layer, and (iii) an anode and a cathode, which sandwich the hole transport layer, the luminescent layer and the electron transport layer. The organic EL device utilizes light emission (fluorescence or phosphorescence) occurring at deactivation of an exciton formed by the recombination of electron with hole, which are injected in the luminescent layer. The organic EL device is widely used for a display and other applications.

Patent documents 1 and 2 disclose organic EL device containing a pyrimidine compound as a luminescent material. The pyrimidine compound includes those which have a substituted phenyl substituent at a 2-position in the pyrimidine ring, but, the positions at which substituents are bonded to the phenyl substituent are not limited. These patent documents are silent on pyrimidine compounds having a substituted phenyl substituent at a 2-position in the pyrimidine ring, which has two specific substituents at 3- and 5-positions of the phenyl substituent. Thus, these patent documents are silent on a pyrimidine compounds of the formula (1a), described below, of the present invention which has a substituted phenyl substituent at a 2-position in the pyrimidine ring, which has two specific substituents at 3- and 5-positions of the phenyl substituent.

Patent documents 3 and 4 disclose an organic EL device containing a pyrimidine compound having a 4-substituted phenyl substituent. However, these documents are silent on a pyrimidine compound of the formula (1a), described below, of the present invention which has a substituted phenyl substituent at a 2-position in the pyrimidine ring, which has two specific substituents at 3- and 5-positions of the phenyl substituent.

Patent document 5 discloses an organic EL device containing a pyrimidine compound having a phenyl group condensed with an aromatic hetero 5-membered ring. However, this document is silent on a pyrimidine compound of the formula (1a), described below, of the present invention which has a substituted phenyl substituent at a 2-position in the pyrimidine ring, which has two substituents at 3- and 5-positions of the phenyl substituent.

Patent document 6 discloses an organic EL device containing a pyrimidine compound. As one example of the pyrimidine compounds, a pyrimidine compound having a substituted phenyl substituent at 2-position of the pyrimidine ring, wherein the phenyl substituent has two phenyl groups at 3- and 5-positions of the phenyl substituent. The two phenyl groups at 3- and 5-positions thereof have no substituent. In contrast, the pyrimidine compounds of the formula (1a), described below, of the present invention has a substituted phenyl substituent at a 2-position in the pyrimidine ring, which has two specific substituents at 3- and 5-positions of the phenyl substituent, wherein each substituent is a phenyl group having a substituent or a condensed aromatic hydrocarbon group. Thus, the pyrimidine compound disclosed in patent document 6 is distinguished from the pyrimidine compound of the formula (1a). The pyrimidine compound disclosed in patent document 6 is also distinguished from the pyrimidine compound of the formula (1c), described below, of the present invention.

Patent document 7 discloses an organic EL device containing a pyrimidine compound. This pyrimidine compound has no polycyclic aromatic group, and thus, is distinguished from the pyrimidine compounds of the formulae (1b) and (1c) of the present invention.

Patent documents 8 and 9 disclose an organic EL device containing 1,3,5-triazine compounds having polycyclic aromatic groups. The triazine compounds are characterized as exhibiting a structural isomerism occurring steric hindrance, and thus, these compounds are distinguished from the pyrimidine compounds of the formulae (1b) and (1c) of the present invention. In patent document 8, there is no working example wherein a 1,3,5-triazine compound having a phenyl group bonded to the triazine ring, said phenyl group having two aromatic hydrocarbon groups each having 2 to 4 rings. Further the two patent documents 8 and 9 suggest nothing about the glass transition temperature (Tg) and electron mobility of the triazine compound.

More specifically patent documents 8 and 9 give only working examples wherein 1,3,5-triazine compounds having the same substituents at 2-, 4- and 6-positions thereof are described, and any description of glass transition temperature (Tg) is not specifically given.

For the use as a basic material of an organic EL device, a thin film of the basic material must be amorphous and have smooth surface. A triazine compound having a highly symmetrical skeletal is highly crystalline, therefore, unsatisfactory for the basic material of the EL device. The cyclic azine compound of the formula (1d), described below, of the present invention has a structure such that different substituents are arranged at 2-, 4- and 6-positions of a 1,3,5-triazne ring, and thus crystallization of a thin film of the cyclic azine compound is controlled. The cyclic azine compound of the present invention has characteristics occurring due to the molecule skeletal which are distinguished from those of the triazine compound having a symmetrical skeletal.

Patent document 10 discloses a nitrogen-containing heterocyclic compound for use in an organic EL device. As one example of the heterocyclic compound, a compound having a 1,3,5-triazine ring and a pyrenyl group is mentioned (Table 12, No. 6-13). However, any specific explanation of this compound and working example thereof are not given, and Tg and electron mobility thereof are not mentioned.

Patent documents 9 and 11 disclose a cyclic azine compound, i.e., 1,3,5-triazine compound for use in an organic EL device. This triazine compound includes those which have substituted phenyl groups at 2-, 4- and 6-positions of the triazine ring, but, the positions of the substituents of the phenyl groups are not limited. These patent documents are silent on the cyclic azine compound of the formula (1c) of the present invention, said azine compound having a phenyl group at 2-position of the triazine ring, which phenyl group has 3,5-di-substituted phenyl groups or 2,6-di-substituted pyridyl groups.

PRIOR ART DOCUMENTS

Patent Documents

Patent document 1: JP 2003-45662
Patent document 2: JP 2004-31004
Patent document 3: WO 2004/039786
Patent document 4: WO 2005/105950
Patent document 5: WO 2007/069569
Patent document 6: WO 2005/085387
Patent document 7: JP 2008-280330
Patent document 8: JP 2001-143869
Patent document 9: JP 2004-22334
Patent document 10: JP 2004-2297
Patent document 11: JP 2007-137829

DISCLOSURE OF THE INVENTION

Problems to Be Solved by the Invention

An object of the present invention is to provide a cyclic azine compound having a novel chemical structure which gives, when it is used as a basic material for an organic EL device, an organic EL device exhibiting improved drivability at a low voltage and enhanced light emission with a high efficiency; an organic EL device having high glass transition temperature and high electron mobility; or an organic EL element exhibiting good charge-injection and charge-transport property and having enhanced durability and life.

Another object of the present invention is to provide an industrially advantageous process for producing the above-mentioned cyclic azine compound.

A further object of the present invention is to provide an industrially advantageous organic EL device containing the above-mentioned cyclic azine compound as a constitutional component.

Means for Solving the Problems

The inventors made an extensive search to solve the above-mentioned problems, and have found that a cyclic azine compound of the formula (1) having two different substituents on the azine ring according to the present invention can be formed into a thin film by the conventional procedure such as vacuum deposition and spin coating, and the thin film exhibits good electron transport characteristics. The inventors further have found that a fluorescent or phosphorescent organic EL device having an organic compound layer comprised of the cyclic azine compound is characterized as confining an exciton therein with high efficiency, and hence, as exhibiting enhanced drivability at a low voltage as well as improved light emission with high efficiency.

Thus, in one aspect of the present invention, there is provided a cyclic azine compound represented by the general formula (1):

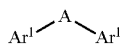

(1)

wherein, in the formula (1), each $Ar^1$ represents an aromatic group, which is unsubstituted or substituted by an alkyl group having 1 to 4 carbon atoms, a phenyl group or a pyridyl group; and
A represents a group selected from the group consisting of those which are represented by the following general formulae (2) to (5).

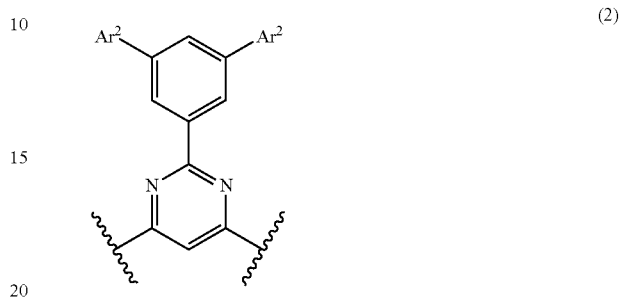

(2)

wherein, in the formula (2), each $Ar^2$ represents a substituted phenyl group or a condensed aromatic hydrocarbon group not having a 16 group element, provided that a 1,3,5-trimethylphenyl group is excluded from $Ar^2$;

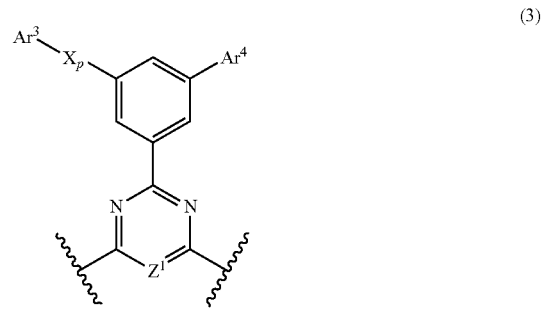

(3)

wherein, in the formula (3), $Ar^3$ represents a phenyl group, a pyridyl group or a pyrimidyl group; $Ar^4$ represents a substituted or unsubstituted aromatic hydrocarbon group having 2 to 4 rings; X represents a phenylene group or a pyridylene group; p represents an integer of 0 to 2 provided that, when p is 2, the two Xs may be the same or different; and $Z^1$ represents a carbon or nitrogen atom;

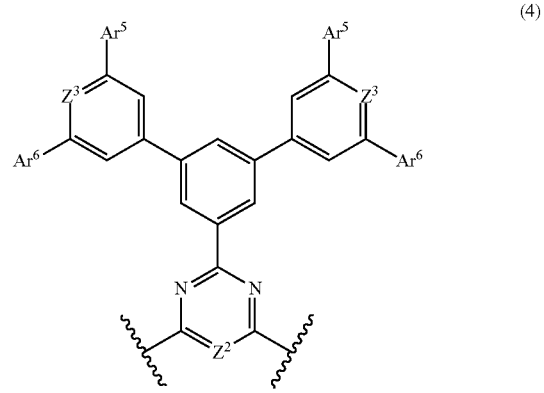

(4)

wherein, in the formula (4), each $Ar^5$ and each $Ar^6$ represent a phenyl group or a pyridyl group; $Z^2$ and each $Z^3$ represent a carbon atom or a nitrogen atom, provided that, when each $Z^3$ represents a carbon atom, each $Ar^5$ and each $Ar^6$ cannot represent simultaneously a phenyl group; and

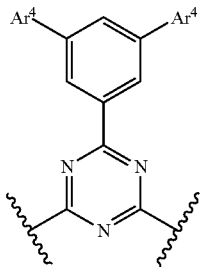
(5)

wherein, in the formula (5), each $Ar^4$ independently represents an aromatic hydrocarbon group having 2 to 4 rings.

In another aspect of the present invention, there is provided a process for preparing a cyclic azine compound represented by the general formula (1a):

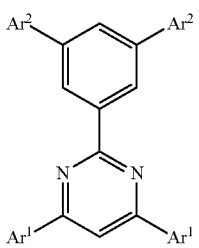
(1a)

wherein, in the formula (1a), each $Ar^1$ represents an aromatic group, which is unsubstituted or substituted by an alkyl group having 1 to 4 carbon atoms, a phenyl group or a pyridyl group; and each $Ar^2$ represents a substituted phenyl group or a condensed aromatic hydrocarbon group not having a 16 group element, provided that a 1,3,5-trimethylphenyl group is excluded from $Ar^2$;

characterized by coupling a compound represented by the general formula (6) with a compound represented by the general formula (7) in the presence of a palladium catalyst and in the presence or absence of a base;

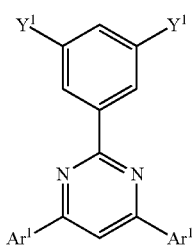
(6)

wherein, in the formula (6), each $Ar^1$ represents an aromatic group, which is unsubstituted or substituted by an alkyl group having 1 to 4 carbon atoms, a phenyl group or a pyridyl group; and each $Y^1$ represents a chlorine, bromine or iodine atom;

$$Ar^2-M \quad (7)$$

wherein, in the formula (7), $Ar^2$ represents a substituted phenyl group or a condensed aromatic hydrocarbon group not having a 16 group element, provided that a 1,3,5-trimethylphenyl group is excluded from $Ar^2$; and M represents a metal group or a hetero atom group.

In still another aspect of the present invention, there is provided a process for preparing a cyclic azine compound represented by the general formula (1a):

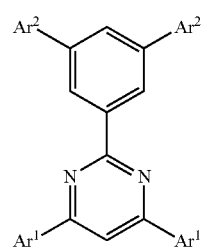
(1a)

wherein, in the formula (1a), each $Ar^1$ represents an aromatic group, which is unsubstituted or substituted by an alkyl group having 1 to 4 carbon atoms, a phenyl group or a pyridyl group; and each $Ar^2$ represents a substituted phenyl group or a condensed aromatic hydrocarbon group not having a 16 group element, provided that a 1,3,5-trimethylphenyl group is excluded from $Ar^2$;

characterized by coupling a compound represented by the general formula (8) with a compound represented by the general formula (9) in the presence of a palladium catalyst and a base;

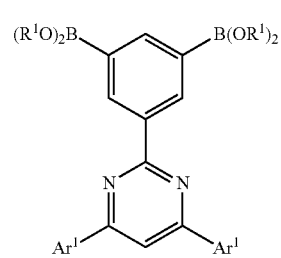
(8)

wherein, in the formula (8), each $Ar^1$ represents an aromatic group, which is unsubstituted or substituted by an alkyl group having 1 to 4 carbon atoms, a phenyl group or a pyridyl group; each $R^1$ represents a hydrogen atom, an alkyl group having 1 to 4 carbon atoms or a phenyl group; and groups $R^1$ in the two —$B(OR^1)$ groups may be the same or different, and two groups $R^1$ in each of the two —$B(OR^1)$ groups may form a ring together with the oxygen atoms and the boron atom;

$$Ar^2-Y^1 \quad (9)$$

wherein, in the formula (9), $Ar^2$ represents a substituted phenyl group or a condensed aromatic hydrocarbon group not having a 16 group element, provided that a 1,3,5-trimethylphenyl group is excluded from $Ar^2$; and $Y^1$ represents a chlorine, bromine or iodine atom.

In a further aspect of the present invention, there is provided a process for preparing a cyclic azine derivative represented by the general formula (1b):

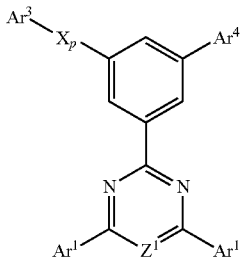

(1b)

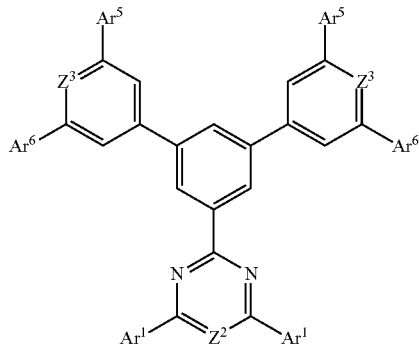

(1c)

wherein, in the formula (1b), each $Ar^1$ represents an aromatic group, which is unsubstituted or substituted by an alkyl group having 1 to 4 carbon atoms, a phenyl group or a pyridyl group; $Ar^3$ represents a phenyl group, a pyridyl group or a pyrimidyl group; $Ar^4$ represents a substituted or unsubstituted aromatic hydrocarbon group having 2 to 4 rings; X represents a phenylene group or a pyridylene group; p represents an integer of 0 to 2 provided that, when p is 2, the two Xs may be the same or different; and $Z^1$ represents a carbon or nitrogen atom;

characterized by coupling a compound represented by the general formula (10) with a compound represented by the general formula (11) in the presence of a palladium catalyst and in the presence or absence of a base;

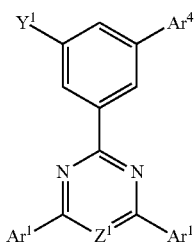

(10)

wherein, in the formula (10), each $Ar^1$ represents an aromatic group, which is unsubstituted or substituted by an alkyl group having 1 to 4 carbon atoms, a phenyl group or a pyridyl group; $Ar^4$ represents a substituted or unsubstituted aromatic hydrocarbon group having 2 to 4 rings; $Z^1$ represents a carbon or nitrogen atom; and $Y^1$ represents a chlorine, bromine or iodine atom;

$Ar^3$—Xp-M (11)

wherein, in the formula (11), $Ar^3$ represents a phenyl group, a pyridyl group or a pyrimidyl group; X represents a phenylene group or a pyridylene group; p represents an integer of 0 to 2 provided that, when p is 2, the two Xs may be the same or different; and M represents a metal group or a hetero atom group.

In a further aspect of the present invention, there is provided a process for preparing a cyclic azine compound represented by the general formula (1c):

wherein, in the formula (1c), each $Ar^1$ represents an aromatic group which is unsubstituted or substituted by an alkyl group having 1 to 4 carbon atoms, a phenyl group or a pyridyl group; each $Ar^5$ and each $Ar^6$ represent a phenyl group or a pyridyl group; and $Z^2$ and each $Z^3$ represent a carbon or nitrogen atom, provided that, when each $Z^3$ represents a carbon atom, each $Ar^5$ and each $Ar^6$ cannot be simultaneously a phenyl group;

characterized by coupling a compound represented by the general formula (12) with a compound represented by the general formula (13) in the presence of a palladium catalyst and a base;

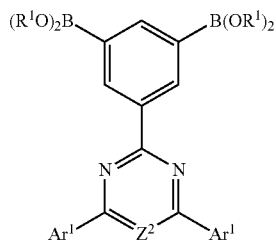

(12)

wherein, in the formula (12), each $Ar^1$ represents an aromatic group, which is unsubstituted or substituted by an alkyl group having 1 to 4 carbon atoms, a phenyl group or a pyridyl group; $Z^2$ represents a carbon or nitrogen atom; each $R^1$ represents a hydrogen atom, an alkyl group having 1 to 4 carbon atoms or a phenyl group; and groups $R^1$ in the two —$B(OR^1)_2$ groups may be the same or different, and two groups $R^1$ in each of the two —$B(OR^1)_2$ groups may form a ring together with the oxygen atoms and the boron atom;

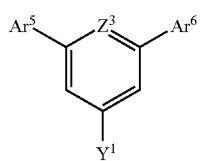

(13)

wherein, in the formula (13), $Ar^5$ and $Ar^6$ represent a phenyl group or a pyridyl group; and $Z^3$ represents a carbon or nitrogen atom, provided that, when $Z^3$ represents a carbon atom, $Ar^5$ and $Ar^6$ cannot be simultaneously a phenyl group; and $Y^1$ represents a chlorine, bromine or iodine atom.

In a further aspect of the present invention, there is provided a process for preparing a cyclic azine compound represented by the general formula (1d):

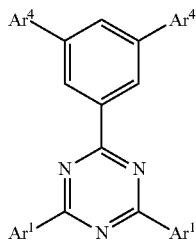
(1d)

wherein, in the formula (1d), each Ar¹ represents an aromatic group, which is unsubstituted or substituted by an alkyl group having 1 to 4 carbon atoms, a phenyl group or a pyridyl group; and each Ar⁴ independently represents an unsubstituted or substituted aromatic hydrocarbon group having 2 to 4 rings;

characterized by coupling a compound represented by the general formula (14) with a compound represented by the general formula (15) in the presence of a palladium catalyst and a base;

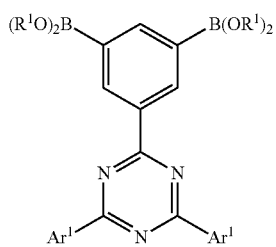
(14)

wherein, in the formula (14), each Ar¹ represents an aromatic group, which is unsubstituted or substituted by an alkyl group having 1 to 4 carbon atoms, a phenyl group or a pyridyl group; each R¹ represents a hydrogen atom, an alkyl group having 1 to 4 carbon atoms or a phenyl group; and groups R¹ in the two —B(OR¹)₂ groups may be the same or different, and two groups R¹ in each of the two —B(OR¹)₂ groups may form a ring together with the oxygen atoms and the boron atom;

Ar⁴—Y¹ (15)

wherein, in the formula (15), Ar⁴ represents an unsubstituted or substituted aromatic hydrocarbon group having 2 to 4 rings; and Y¹ represents a chlorine, bromine or iodine atom.

In a further aspect of the present invention, there is provided an organic electroluminescent device comprising as a constituent a cyclic azine compound represented by the general formula (1):

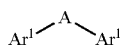
(1)

wherein, in the formula (1), each Ar¹ represents an aromatic group, which is unsubstituted or substituted by an alkyl group having 1 to 4 carbon atoms, a phenyl group or a pyridyl group; and A represents a group selected from the group consisting of those which are represented by the following general formulae (2) to (5):

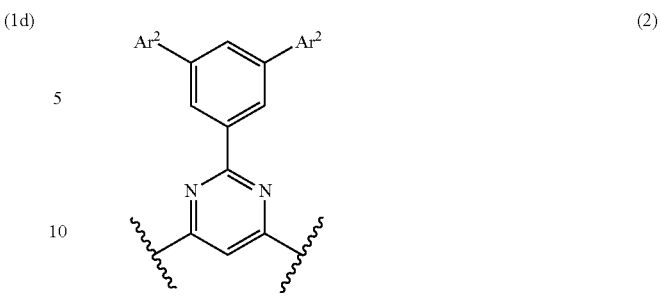
(2)

wherein, in the formula (2), each Ar² represents a substituted phenyl group or a condensed aromatic hydrocarbon group not having a 16 group element, provided that a 1,3,5-trimethylphenyl group is excluded from Ar²;

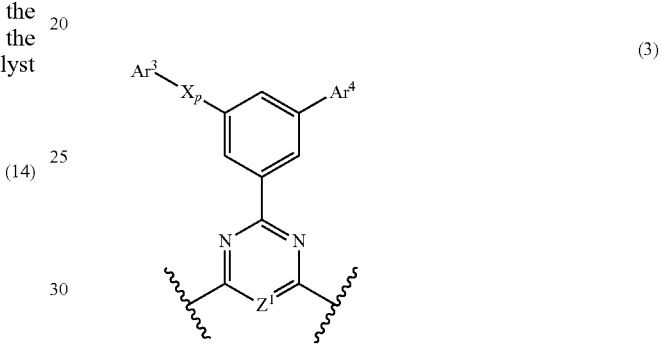
(3)

wherein, in the formula (3), Ar³ represents a phenyl group, a pyridyl group or a pyrimidyl group; Ar⁴ represents a substituted or unsubstituted aromatic hydrocarbon group having 2 to 4 rings; X represents a phenylene group or a pyridylene group; p represents an integer of 0 to 2 provided that, when p is 2, the two Xs may be the same or different; and Z¹ represents a carbon or nitrogen atom;

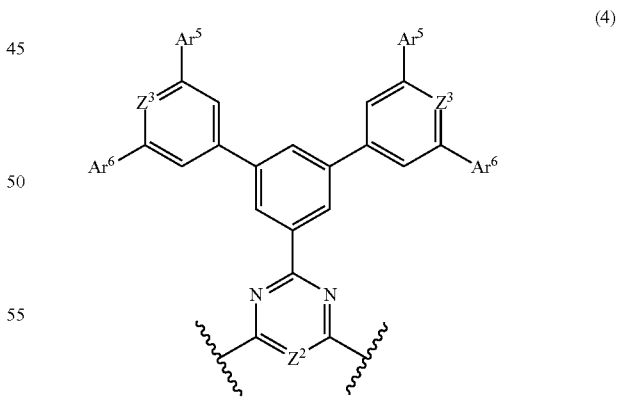
(4)

wherein, in the formula (4), each Ar⁵ and each Ar⁶ represent a phenyl group or a pyridyl group; Z² and each Z³ represent a carbon atom or a nitrogen atom, provided that, when each Z³ represents a carbon atom, each Ar⁵ and each Ar⁶ cannot represent simultaneously a phenyl group; and

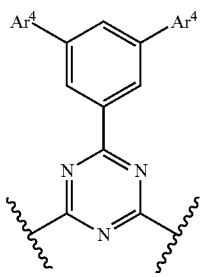

(5)

wherein, in the formula (5), each Ar⁴ independently represents an aromatic hydrocarbon group having 2 to 4 carbon atoms.

Effect of the Invention

The cyclic azine derivative having a novel chemical structure according to the present invention gives, when it is used as a basic material for a fluorescent or phosphorescent organic EL device, an organic EL device exhibiting improved drivability at a low voltage and enhanced light emission with a high efficiency.

More specifically, a thin film comprised of the cyclic azine compound of the present invention has high surface smoothness, amorphousness, heat resistance, electron transportability, hole block capability, resistance to oxidation and reduction, moisture resistance, oxygen resistance and electron injection characteristics, and therefore, the thin film is suitable as a component an organic EL device, especially useful as electron transport material, hole blocking material and fluorescent host material.

BRIEF DESCRIPTION OF THE DRAWINGS

FIG. 1 illustrates a schematic cross-section of an example of an organic EL device having a thin film layer comprised of the cyclic azine compound of the present invention.

EXPLANATION OF REFERENCE NUMERALS

1. Glass substrate with transparent ITO electrode
2. Hole injection layer
3. Hole transport layer
4. Light emitting layer
5. Electron transport layer
6. Cathode layer

MODE FOR CARRYING OUT THE INVENTION

The invention will now be described in detail.

In the general formula (1), each Ar¹ represents an aromatic group, which is unsubstituted or substituted by an alkyl group having 1 to 4 carbon atoms, a phenyl group or a pyridyl group. Ar¹ includes, for example, a phenyl group which is unsubstituted or substituted by an alkyl group having 1 to 4 carbon atoms, a phenyl group or a pyridyl group; a naphthyl group which is unsubstituted or substituted by an alkyl group having 1 to 4 carbon atoms, a phenyl group or a pyridyl group; an anthryl group which is unsubstituted or substituted by an alkyl group having 1 to 4 carbon atoms, a phenyl group or a pyridyl group; a phenanthryl group which is unsubstituted or substituted by an alkyl group having 1 to 4 carbon atoms, a phenyl group or a pyridyl group; and a pyridyl group which is unsubstituted or substituted by an alkyl group having 1 to 4 carbon atoms, a phenyl group or a pyridyl group.

Specific examples of such unsubstituted or substituted aromatic groups are mentioned below, but should not be limited thereto.

As specific examples of the phenyl group which is unsubstituted or substituted by an alkyl group having 1 to 4 carbon atoms, a phenyl group or a pyridyl group, there can be mentioned phenyl group, and substituted phenyl groups such as a p-tolyl group, m-tolyl group, o-tolyl group, 4-trifluoromethylphenyl group, 3-trifluoromethylphenyl group, 2-trifluoromethylphenyl group, 2,4-dimethylphenyl group, 3,5-dimethylphenyl group, 2,6-dimethylphenyl group, a mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group, 2,4-dibutylphenyl group, 3,5-dibutylphenyl group, 2-tert-butylphenyl group, 3-tert-butylphenyl group, 4-tert-butylphenyl group, 2,4-di-tert-butylphenyl group and 3,5-di-tert-butylphenyl group; biphenyl groups such as 4-biphenylyl group, 3-biphenylyl group and 2-biphenylyl group; terphenyl groups such as 1,1':4',1"-terphenyl-3-yl group, 1,1':4',1"-terphenyl-4-yl group, 1,1':3',1"-terphenyl-3-yl group, 1,1':3',1"-terphenyl-4-yl group, 1,1':3',1"-terphenyl-5'-yl group, 1,1':2',1"-terphenyl-3-yl group, 1,1':2',1"-terphenyl-4-yl group and 1,1':2',1"-terphenyl-4'-yl group; and 2-(2-pyridyl)phenyl group, 3-(2-pyridyl)phenyl group, 4-(2-pyridyl)phenyl group, 2-(3-pyridyl)phenyl group, 3-(3-pyridyl)phenyl group, 4-(3-pyridyl)phenyl group, 2-(4-pyridyl)phenyl group, 3-(4-pyridyl)phenyl group and 4-(4-pyridyl)phenyl group.

Of these, as the unsubstituted or substituted phenyl groups, phenyl group, p-tolyl group, m-tolyl group, o-tolyl group, 2,6-dimethylphenyl group, 4-tert-butylphenyl group, 4-biphenylyl group, 3-biphenylyl group, 2-biphenylyl group; 1,1':4',1"-terphenyl-4-yl group, 1,1':2',1"-terphenyl-4-yl group, 1,1':3',1"-terphenyl-5'-yl group, 3-(2-pyridyl)phenyl group, 4-(2-pyridyl)phenyl group, 3-(3-pyridyl)phenyl group, 4-(3-pyridyl)phenyl group, 3-(4-pyridyl)phenyl group and 4-(4-pyridyl)phenyl group are preferable in view of the performance thereof as a material for an organic electroluminescent device. Phenyl group, p-tolyl group, 4-biphenylyl group, 2-biphenylyl group and 4-(3-pyridyl)phenyl are especially preferable in view of ease in synthesis.

As specific examples of the unsubstituted or substituted naphthyl groups, there can be mentioned 1-naphthyl group and 2-naphthyl group; and 4-methylnaphthalen-1-yl group, 4-trifluoromethylnaphthalen-1-yl group, 4-ethylnaphthalen-1-yl group, 4-propylnaphthalen-1-yl group, 4-butylnaphthalen-1-yl group, 4-tert-butylnaphthalen-1-yl group, 5-methylnaphthalen-1-yl group, 5-trifluoromethylnaphthalen-1-yl group, 5-ethylnaphthalen-1-yl group, 5-propylnaphthalen-1-yl group, 5-butylnaphthalen-1-yl group, 5-tert-butylnaphthalen-1-yl group, 6-methylnaphthalen-2-yl group, 6-trifluoromethylnaphthalen-2-yl group, 6-ethylnaphthalen-2-yl group, 6-propylnaphthalen-2-yl group, 6-butylnaphthalen-2-yl group, 6-tert-butylnaphthalen-2-yl group, 7-methylnaphthalen-2-yl group, 7-trifluoromethylnaphthalen-2-yl group, 7-ethylnaphthalen-2-yl group, 7-propylnaphthalen-2-yl group, 7-butylnaphthalen-2-yl group and 7-tert-butylnaphthalen-2-yl group.

Of these, as the unsubstituted or substituted naphthyl groups, 1-naphthyl group, 4-methylnaphthalene-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylaphthalene-2-yl group and 7-tert-butylnaphthalen-2-yl group are preferable in view of the performance thereof as a material for an organic electroluminescent device. 2-Naphthyl group is especially preferable because of ease in synthesis.

As specific examples of the unsubstituted or substituted anthryl groups, there can be mentioned 1-anthryl group, 2-anthryl group and 9-anthryl group; and 2-methylanthracen-1-yl group, 3-methylanthracen-1-yl group, 4-methylanthracen-1-yl group, 9-methylanthracen-1-yl group, 10-methylanthracen-1-yl group, 2-phenylanthracen-1-yl group, 3-phenylanthracen-1-yl group, 4-phenylanthracen-1-yl group, 5-phenylanthracen-1-yl group, 6-phenylanthracen-1-yl group, 7-phenylanthracen-1-yl group, 8-phenylanthracen-1-yl group, 9-phenylanthracen-1-yl group, 10-phenylanthracen-1-yl group, 1-methylanthracen-2-yl group, 3-methylanthracen-2-yl group, 4-methylanthracen-2-yl group, 9-methylanthracen-2-yl group, 10-methylanthracen-2-yl group, 1-phenylanthracen-2-yl group, 3-phenylanthracen-2-yl group, 4-phenylanthracen-2-yl group, 5-phenylanthracen-2-yl group, 6-phenylanthracen-2-yl group, 7-phenylanthracen-2-yl group, 8-phenylanthracen-2-yl group, 9-phenylanthracen-2-yl group, 10-phenylanthracen-2-yl group, 2-methylanthracen-9-yl group, 3-methylanthracen-9-yl group, 4-methylanthracen-9-yl group, 10-methylanthracen-9-yl group, 2-phenylanthracen-9-yl group, 3-phenylanthracen-9-yl group, 4-phenylanthracen-9-yl group, 5-phenylanthracen-9-yl group, 6-phenylanthracen-9-yl group, 7-phenylanthracen-9-yl group, 1-phenylanthracen-9-yl group and 10-phenylanthracen-9-yl group.

Of these, as the unsubstituted or substituted anthryl groups, 1-anthryl group, 2-anthryl group, 9-anthryl group, 4-phenylanthracen-1-yl group and 4-phenylanthracen-9-yl group are preferable in view of the performance thereof as a material for an organic electroluminescent device. 1-Anthryl group, 2-anthryl group and 9-anthryl group are especially preferable because of low molecular weight.

As specific examples of the unsubstituted or substituted phenanthryl groups, there can be mentioned 1-phenanthryl group, 2-phenanthryl group, 3-phenanthryl group, 4-phenanthryl group and 9-phenanthryl group; and 2-phenylphenanthren-1-yl group, 3-phenylphenanthren-1-yl group, 4-phenylphenanthren-1-yl group, 9-phenylphenanthren-1-yl group, 1-phenylphenanthren-2-yl group, 3-phenylphenanthren-2-yl group, 4-phenylphenanthren-2-yl group, 8-phenylphenanthren-2-yl group, 8-phenylphenanthren-3-yl group, 9-phenylphenanthren-2-yl group, 1-phenylphenanthren-3-yl group, 2-phenylphenanthren-3-yl group, 4-phenylphenanthren-3-yl group, 9-phenylphenanthren-3-yl group, 1-phenylphenanthren-4-yl group, 2-phenylphenanthren-4-yl group, 3-phenylphenanthren-4-yl group, 9-phenylphenanthren-4-yl group, 1-phenylphenanthren-9-yl group, 2-phenylphenanthren-9-yl group, 3-phenylphenanthren-9-yl group and 4-phenylphenanthren-9-yl group.

Of these, as the unsubstituted or substituted phenanthryl groups, 2-phenanthryl group, 3-phenanthryl group, 8-phenylphenanthren-2-yl group and 8-phenylphenanthren-3-yl group are preferable in view of the performance thereof as a material for an organic electroluminescent device. 2-Phenanthryl group and 3-phenanthryl group are especially preferable because of low molecular weight.

As specific examples of the unsubstituted or substituted pyridyl groups, there can be mentioned 2-pyridyl group, 3-pyridyl group and 4-pyridyl group; and 3-methylpyridin-2-yl group, 4-methylpyridin-2-yl group, 5-methylpyridin-2-yl group, 6-methylpyridin-2-yl group, 2-methylpyridin-3-yl group, 4-methylpyridin-3-yl group, 5-methylpyridin-3-yl group, 6-methylpyridin-3-yl group, 2-methylpyridin-4-yl group, 3-methylpyridin-4-yl group, 3-ethylpyridin-2-yl group, 4-ethylpyridin-2-yl group, 2-ethylpyridin-3-yl group, 5-ethylpyridin-3-yl group, 2-ethylpyridin-4-yl group, 3-ethylpyridin-4-yl group, 3-propylpyridin-2-yl group, 4-butylpyridin-2-yl group, 5-butylpyridin-2-yl group, 2-propylpyridin-3-yl group, 2-butylpyridin-4-yl group, 4-tert-butylpyridin-2-yl group, 5-tert-butylpyridin-2-yl group, 6-tert-butylpyridin-2-yl group, 5-tert-butylpyridin-3-yl group, 6-tert-butylpyridin-3-yl group, 2-tert-butylpyridin-4-yl group, 3-phenylpyridin-2-yl group, 4-phenylpyridin-2-yl group, 5-phenylpyridin-2-yl group, 6-phenylpyridin-2-yl group, 2-phenylpyridin-3-yl group, 4-phenylpyridin-3-yl group, 5-phenylpyridin-3-yl group, 6-phenylpyridin-3-yl group, 2-phenylpyridin-4-yl group and 3-phenylpyridin-4-yl group.

Of these, as the unsubstituted or substituted pyridyl groups, 2-pyridyl group, 3-pyridyl group, 4-pyridyl group, 4-methylpyridin-2-yl group, 6-methylpyridin-2-yl group, 6-methylpyridin-3-yl group, 4-tert-butylpyridin-2-yl group and 6-tert-butylpyridin-2-yl group are preferable in view of the performance thereof as a material for an organic electroluminescent device. 2-Pyridyl group is especially preferable because of ease in synthesis.

In the general formula (2), a substituted phenyl group represented by each $Ar^2$ includes, for example, a phenyl group substituted by an alkyl group having 1 to 4 carbon atoms, provided that 1,3,5-trimethylphenyl group is excluded from the alkyl-substituted phenyl group; a phenyl group substituted by a halogen atom; a phenyl group substituted by an unsubstituted or substituted phenyl group; a phenyl group substituted by an unsubstituted or substituted pyrimidinyl group; a phenyl group substituted by an unsubstituted or substituted thiazolyl group; a phenyl group substituted by a pyridyl group; and a phenyl group substituted by a phenanthrolinyl group.

Specific examples of the substituted phenyl group are mentioned below, but should not be limited thereto.

As specific examples of the phenyl group substituted by an alkyl group having 1 to 4 carbon atoms, there can be mentioned p-tolyl group, m-tolyl group, o-tolyl group, 4-trifluoromethylphenyl group, 3-trifluoromethylphenyl group, 2-trifluoromethylphenyl group, 2,4-dimethylphenyl group, 3,5-dimethylphenyl group, 2,6-dimethylphenyl group, a mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group, 2,4-dibutylphenyl group, 3,5-dibutylphenyl group, 2-tert-butylphenyl group, 3-tert-butylphenyl group, 4-tert-butylphenyl group, 2,4-di-tert-butylphenyl group and 3,5-di-tert-butylphenyl group;

Of these, as the phenyl group substituted by an alkyl group having 1 to 4 carbon atoms, p-tolyl group, m-tolyl group, o-tolyl group, 4-trifluoromethylphenyl group and 4-butylphenyl group are preferable in view of the performance thereof as a material for an organic electroluminescent device. P-tolyl group and m-tolyl group are especially preferable because of inexpensiveness.

As specific examples of the phenyl group substituted by a halogen atom, there can be mentioned 3-chlorophenyl group, 4-chlorophenyl group, 3,4-dichlorophenyl group, 3,5-dichlorophenyl group, 3-bromophenyl group, 4-bromophenyl group, 3,4-dibromophenyl group and 3,5-dibromophenyl group. Of these, 3-chlorophenyl group is preferable because of ease in synthesis.

As specific examples of the phenyl group substituted by an unsubstituted or substituted phenyl group, there can be mentioned 4-biphenylyl group, 3-biphenylyl group, 2-biphenylyl group, 2-methylbiphenyl-4-yl group, 3-methylbiphenyl-4-yl group, 2'-methylbiphenyl-4-yl group, 4'-methylbiphenyl-4-yl group, 2,2'-dimethylbiphenyl-4-yl group, 2',4',6'-trimethylbiphenyl-4-yl group, 6-methylbiphenyl-3-yl group, 5-methylbiphenyl-3-yl group, 2'-methylbiphenyl-3-yl group, 4'-methylbiphenyl-3-yl group, 6,2'-dimethylbiphenyl-3-yl group, 2',4',6'-trimethylbiphenyl-3-yl group, 5-methylbiphenyl-2-yl group, 6-methylbiphenyl-2-yl group, 2'-methylbiphenyl-2-yl group, 4'-methylbiphenyl-2-yl group, 6,2'-dimethylbiphenyl-2-yl group, 2',4',6'-trimethylbiphenyl-2-yl group, 2-trifluoromethylbiphenyl-4-yl group, 3-trifluoromethylbiphenyl-4-yl group, 2'-trifluoromethylbiphenyl-4-yl group, 4'-trifluoromethylbiphenyl-4-yl group, 6-trifluoromethylbiphenyl-3-yl group, 5-trifluoromethylbiphenyl-3-yl group, 2'-trifluoromethylbiphenyl-3-yl group, 4'-trifluoromethylbiphenyl-3-yl group, 5-trifluoromethylbiphenyl-2-yl group, 6-trifluoromethylbiphenyl-2-yl group, 2'-trifluoromethylbiphenyl-2-yl group, 4'-trifluoromethylbiphenyl-2-yl group, 3-ethylbiphenyl-4-yl group, 4'-ethylbiphenyl-4-yl group, 2',4',6'-triethylbiphenyl-4-yl group, 6-ethylbiphenyl-3-yl group, 4'-ethylbiphenyl-3-yl group, 5-ethylbiphenyl-2-yl group, 4'-ethylbiphenyl-2-yl group, 2',4',6'-triethylbiphenyl-2-yl group, 3-propylbiphenyl-4-yl group, 4'-propylbiphenyl-4-yl group, 2',4',6'-tripropylbiphenyl-4-yl group, 6-propylbiphenyl-3-yl group, 4'-propylbiphenyl-3-yl group, 5-propylbiphenyl-2-yl group, 4'-propylbiphenyl-2-yl group, 2',4',6'-tripropylbiphenyl-2-yl group, 3-isopropylbiphenyl-4-yl group, 4'-isopropylbiphenyl-4-yl group, 2',4',6'-triisopropylbiphenyl-4-yl group, 6-isopropylbiphenyl-3-yl group, 4'-isopropylbiphenyl-3-yl group, 5-isopropylbiphenyl-2-yl group, 4'-isopropylbiphenyl-2-yl group, 2',4',6'-triisopropylbiphenyl-2-yl group, 3-butylbiphenyl-4-yl group, 4'-butylbiphenyl-4-yl group, 2',4',6'-tributylbiphenyl-4-yl group, 6-butylbiphenyl-3-yl group, 4'-butylbiphenyl-3-yl group, 5-butylbiphenyl-2-yl group, 4'-butylbiphenyl-2-yl group, 2',4',6'-tributylbiphenyl-2-yl group, 3-tert-butylbiphenyl-4-yl group, 4'-tert-butylbiphenyl-4-yl group, 2',4',6'-tri-tert-butylbiphenyl-4-yl group, 6-tert-butylbiphenyl-3-yl group, 4'-tert-butylbiphenyl-3-yl group, 5-tert-butylbiphenyl-2-yl group, 4'-tert-butylbiphenyl-2-yl group, 2',4',6'-tri-tert-butylbiphenyl-2-yl group, 1,1':4',1''-terphenyl-3-yl group, 1,1':4',1''-terphenyl-4-yl group, 1,1':3',1''-terphenyl-3-yl group, 1,1':3',1''-terphenyl-4-yl group, 1,1':3',1''-terphenyl-5'-yl group, 1,1':2',1''-terphenyl-3-yl group, 1,1':2',1''-terphenyl-4-yl group, 1,1':2',1''-terphenyl-4'-yl group, 2'-(2-pyridyl)biphenyl-2-yl group, 3'-(2-pyridyl)biphenyl-2-yl group, 4'-(2-pyridyl)biphenyl-2-yl group, 2'-(3-pyridyl)biphenyl-2-yl group, 3'-(3-pyridyl)biphenyl-2-yl group, 4'-(3-pyridyl)biphenyl-2-yl group, 2'-(4-pyridyl)biphenyl-2-yl group, 3'-(4-pyridyl)biphenyl-2-yl group, 4'-(4-pyridyl)biphenyl-2-yl group, 2'-(2-pyridyl)biphenyl-3-yl group, 3'-(2-pyridyl)biphenyl-3-yl group, 4'-(2-pyridyl)biphenyl-3-yl group, 2'-(3-pyridyl)biphenyl-3-yl group, 3'-(3-pyridyl)biphenyl-3-yl group, 4'-(3-pyridyl)biphenyl-3-yl group, 2'-(4-pyridyl)biphenyl-3-yl group, 3'-(4-pyridyl)biphenyl-3-yl group, 4'-(4-pyridyl)biphenyl-3-yl group, 2'-(2-pyridyl)biphenyl-4-yl group, 3'-(2-pyridyl)biphenyl-4-yl group, 4'-(2-pyridyl)biphenyl-4-yl group, 2'-(3-pyridyl)biphenyl-4-yl group, 3'-(3-pyridyl)biphenyl-4-yl group, 4'-(3-pyridyl)biphenyl-4-yl group, 2'-(4-pyridyl)biphenyl-4-yl group, 3'-(4-pyridyl)biphenyl-4-yl group and 4'-(4-pyridyl)biphenyl-4-yl group.

Of these, as the phenyl group substituted by an unsubstituted or substituted phenyl group, 2-biphenylyl group, 3-biphenylyl group, 4-biphenylyl group, 1,1':3',1''-terphenyl-5'-yl group, 2'-(2-pyridyl)biphenyl-3-yl group, 3'-(2-pyridyl)biphenyl-3-yl group and 4'-(2-pyridyl)biphenyl-3-yl group are preferable in view of the performance thereof as a material for an organic electroluminescent device. 3-Biphenylyl group and 3'-(2-pyridyl)biphenyl-3-yl group are especially preferable because of ease in synthesis.

As specific examples of the phenyl group which is substituted by unsubstituted or substituted pyrimidinyl groups, there can be mentioned 2-(2-pyrimidinyl)phenyl group, 3-(2-pyrimidinyl)phenyl group, 4-(2-pyrimidinyl)phenyl group, 2-(4-pyrimidinyl)phenyl group, 3-(4-pyrimidinyl)phenyl group, 4-(4-pyrimidinyl)phenyl group, 2-(5-pyrimidinyl)phenyl group, 3-(5-pyrimidinyl)phenyl group, 4-(5-pyrimidinyl)phenyl group, 2-(4,6-dimethylpyrimidin-2-yl)phenyl group, 3-(4,6-dimethylpyrimidin-2-yl)phenyl group, 4-(4,6-dimethylpyrimidin-2-yl)phenyl group, 2-(4,6-diphenylpyrimidin-2-yl)phenyl group, 3-(4,6-diphenylpyrimidin-2-yl)phenyl group, 4-(4,6-diphenylpyrimidin-2-yl)phenyl group, 3-(4,6-di-p-tolylpyrimidin-2-yl)phenyl group, 4-(4,6-di-m-tolylpyrimidin-2-yl)phenyl group, 3-[4,6-bis(3,5-dimethylphenyl)pyrimidin-2-yl]phenyl group, 4-[4,6-bis(2,6-dimethylphenyl)pyrimidin-2-yl]phenyl group, 3-[4,6-bis(2-biphenylyl)pyrimidin-2-yl]phenyl group, 4-[4,6-bis(3-biphenylyl)pyrimidin-2-yl]phenyl group, 3-[4,6-di(2-naphtyl)pyrimidin-2-yl]phenyl group and 4-[4,6-di(9-anthryl)pyrimidin-2-yl]phenyl group.

Of these, as the phenyl group substituted by an unsubstituted or substituted pyrimidinyl group, 4-(2-pyrimidinyl)phenyl group, 4-(5-pyrimidinyl)phenyl group, 3-(4,6-dimethylpyrimidin-2-yl)phenyl group, 4-(4,6-dimethylpyrimidin-2-yl)phenyl group, 3-(4,6-diphenylpyrimidin-2-yl)phenyl group and 4-(4,6-diphenylpyrimidin-2-yl)phenyl group are preferable in view of the performance thereof as a material for an organic EL device. 4-(2-Pyrimidinyl)phenyl group and 4-(5-pyrimidinyl)phenyl group are especially preferable because of ease in synthesis.

As specific examples of the phenyl group unsubstituted or substituted thiazolyl group, there can be mentioned 2-(2-thiazolyl)phenyl group, 3-(2-thiazolyl)phenyl group, 4-(2-thiazolyl)phenyl group, 2-(4-thiazolyl)phenyl group, 3-(4-thiazolyl)phenyl group, 4-(4-thiazolyl)phenyl group, 2-(5-thiazolyl)phenyl group, 3-(5-thiazolyl)phenyl group, 4-(5-thiazolyl)phenyl group, 3-(2-thiazolyl)phenyl group, 4-(2-methylthiazol-5-yl)phenyl group, 2-(4,5-dimethylthiazol-2-yl)phenyl group, 3-(4,5-methylthiazol-2-yl)phenyl group, 4-(4,5-methylthiazol-2-yl)phenyl group, 2-(2-phenylthiazol-4-yl)phenyl group, 3-(2-phenylthiazol-4-yl)phenyl group, 4-(2-phenylthiazol-4-yl)phenyl group, 4-(2-phenylthiazol-5-yl)phenyl group, 2-(4,5-diphenylthiazol-2-yl)phenyl group, 3-(4,5-diphenylthiazol-2-yl)phenyl group, 4-(4,5-diphenylthiazol-2-yl)phenyl group, 2-(2-benzothiazolyl)phenyl group, 3-(2-benzothiazolyl)phenyl group, 4-(2-benzothiazolyl)phenyl group, 3-(2-naphthothiazolyl)phenyl group and 4-(2-naphthothiazolyl)phenyl group.

Of these, as the phenyl group substituted by an unsubstituted or substituted thiazolyl group, 3-(4,5-diphenylthiazol-2-yl)phenyl group, 4-(4,5-diphenylthiazol-2-yl)phenyl group and 4-(2-benzothiazolyl)phenyl group are preferable in view of the performance thereof as a material for an organic electroluminescent device. 4-(2-Benzothiazolyl)phenyl group is especially preferable because of ease in synthesis.

As specific examples of the phenyl group substituted by a pyridyl group, there can be mentioned 2-(2-pyridyl)phenyl group, 3-(2-pyridyl)phenyl group, 4-(2-pyridyl)phenyl group, 2-(3-pyridyl)phenyl group, 3-(3-pyridyl)phenyl group, 4-(3-pyridyl)phenyl group, 2-(4-pyridyl)phenyl group, 3-(4-pyridyl)phenyl group, 4-(4-pyridyl)phenyl group, 4-phenyl-2-(2-pyridyl)phenyl group, 5-phenyl-2-(2-pyridyl)phenyl group, 4-phenyl-3-(2-pyridyl)phenyl group, 5-phenyl-3-(2-pyridyl)phenyl group, 6-phenyl-3-(2-pyridyl)phenyl group, 3-phenyl-4-(2-pyridyl)phenyl group, 3-phenyl-2-(3-pyridyl)phenyl group, 4-phenyl-2-(3-pyridyl)phenyl group, 4-phenyl-3-(3-pyridyl)phenyl group, 5-phenyl-3-(3-pyridyl)phenyl group, 6-phenyl-3-(3-pyridyl)phenyl group, 2-phenyl-4-(3-pyridyl)phenyl group, 4-phenyl-2-(4-pyridyl)phenyl group, 4-phenyl-3-(4-pyridyl)phenyl group, 5-phenyl-3-(4-pyridyl)phenyl group, 3-phenyl-4-(4-pyridyl)phenyl group, 3,4-di(2-pyridyl)phenyl group, 3,4-di(3-pyridyl)phenyl group, 3,4-di(4-pyridyl)phenyl group, 3-(2-pyridyl)-4-(3-pyridyl)phenyl group, 3-(2-pyridyl)-4-(4-pyridyl)phenyl group, 3-(3-pyridyl)-4-(2-pyridyl)phenyl group, 3-(4-pyridyl)-4-(2-pyridyl)phenyl group, 3,5-di(2-pyridyl)phenyl group, 3,5-di(3-pyridyl)phenyl group and 3,5-di(4-pyridyl)phenyl group.

Of these, as the phenyl group substituted by a pyridyl group, 2-(2-pyridyl)phenyl group, 3-(2-pyridyl)phenyl group, 4-(2-pyridyl)phenyl group, 3-(3-pyridyl)phenyl group, 4-(3-pyridyl)phenyl group, 3-(4-pyridyl)phenyl group, 4-(4-pyridyl)phenyl group, 5-phenyl-3-(2-pyridyl)phenyl group, 5-phenyl-3-(3-pyridyl)phenyl group, 5-phenyl-3-(4-pyridyl)phenyl group and 3,5-di(2-pyridyl)phenyl group are preferable in view of the performance thereof as a material for an organic EL device. 2-(2-Pyridyl)phenyl group, 3-(2-pyridyl)phenyl group, 4-(3-pyridyl)phenyl group and 4-(4-pyridyl)phenyl group are especially preferable because of ease in synthesis.

As specific examples of the phenyl group substituted by a phenanthrolinyl group, there can be mentioned 2-(2-phenanthrolinyl)phenyl group, 3-(2-phenanthrolinyl)phenyl group, 4-(2-phenanthrolinyl)phenyl group, 2-(3-phenanthrolinyl)phenyl group, 3-(3-phenanthrolinyl)phenyl group, 4-(3-phenanthrolinyl)phenyl group, 2-(4-phenanthrolinyl)phenyl group, 3-(4-phenanthrolinyl)phenyl group and 4-(4-phenanthrolinyl)phenyl group.

Of these, as the phenyl group substituted by a phenanthrolinyl group, 3-(2-phenanthrolinyl)phenyl group, 4-(2-phenanthrolinyl)phenyl group, 3-(3-phenanthrolinyl)phenyl group and 4-(3-phenanthrolinyl)phenyl group are preferable in view of the performance thereof as a material for an organic EL device. 4-(2-Phenanthrolinyl)phenyl group is especially preferable because of ease in synthesis.

In the general formula (2), a condensed aromatic hydrocarbon group not having a 16 group element represented by each $Ar^2$ must have a cyclic structure which does not contain an element of 16 group of the Periodic Table such as an oxygen atom or a sulfur atom. As specific examples of such condensed aromatic hydrocarbon group, there can be mentioned 1-naphthyl group, 2-naphthyl group, 2-anthryl group, 9-anthryl group, 2-phenanthryl group, 3-phenanthryl group, 4-phenanthryl group, 1-pyrenyl group, 2-pyrenyl group, 5-quinolyl group, 6-quinolyl group, 7-quinolyl group, 8-qunolyl group, 5-isoquinolyl group, 6-isoquinolyl group, 7-isoqunolyl group and 8-quinolyl group.

Of these, as the condensed aromatic hydrocarbon group, 2-naphthyl group, 9-anthryl group, 3-phenanthryl group and 6-quinolyl group are preferable in view of the performance thereof as a material for an organic electroluminescent device. 6-Quinolyl group is especially preferable because of ease in synthesis.

In the general formula (3), $Ar^3$ represents a phenyl group, a pyridyl group or a pyrimidinyl group.

In the general formula (3), $Ar^4$ represents an unsubstituted or substituted aromatic hydrocarbon group having 2 to 4 rings, and includes, for example, an unsubstituted or substituted naphthyl group, an unsubstituted or substituted anthryl group, an unsubstituted or substituted phenanthryl group, an unsubstituted or substituted fluorenyl group, an unsubstituted or substituted benzofluorenyl group, an unsubstituted or substituted pyrenyl group and an unsubstituted or substituted triphenylenyl group.

As specific examples of the unsubstituted or substituted naphthyl group represented by $Ar^4$ in the general formula (3), there can be mentioned 1-naphthyl group and 2-naphthyl group; and naphthyl groups substituted by an alkyl group having 1 to 4 carbon atoms, such as 4-methylnaphthalen-1-yl group, 4-trifluoromethylnaphthalen-1-yl group, 4-ethylnaphthalen-1-yl group, 4-propylnaphthalen-1-yl group, 4-butylnaphthalen-1-yl group, 4-tert-butylnaphthalen-1-yl group, 5-methylnaphthalen-1-yl group, 5-trifluoromethylnaphthalen-1-yl group, 5-ethylnaphthalen-1-yl group, 5-propylnaphthalen-1-yl group, 5-butylnaphthalen-1-yl group, 5-tert-butylnaphthalen-1-yl group, 6-methylnaphthalen-2-yl group, 6-trifluoromethylnaphthalen-2-yl group, 6-ethylnaphthalen-2-yl group, 6-propylnaphthalen-2-yl group, 6-butylnaphthalen-2-yl group, 6-tert-butylnaphthalen-2-yl group, 7-methylnaphthalen-2-yl group, 7-trifluoromethylnaphthalen-2-yl group, 7-ethylnaphthalen-2-yl group, 7-propylnaphthalen-2-yl group, 7-butylnaphthalen-2-yl group and 7-tert-butylnaphthalen-2-yl group.

Of these unsubstituted or substituted naphthyl groups, 1-naphthyl group, 4-methylnaphthalen-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylnaphthalen-2-yl group and 7-tert-butylnaphthalen-2-yl group are preferable in view of the performance thereof as a material for an organic electroluminescent device. 1-Naphthyl group is especially preferable because of ease in synthesis.

As specific examples of the unsubstituted or substituted anthryl group represented by $Ar^4$, there can be mentioned 1-anthryl group, 2-anthryl group and 9-anthryl group; and anthryl groups substituted by an alkyl group having 1 to 4 carbon atoms or a phenyl group, such as 2-methylanthracen-1-yl group, 3-methylanthracen-1-yl group, 4-methylanthracen-1-yl group, 9-methylanthracen-1-yl group, 10-methylanthracen-1-yl group, 2-phenylanthracen-1-yl group, 3-phenylanthracen-1-yl group, 4-phenylanthracen-1-yl group, 5-phenylanthracen-1-yl group, 6-phenylanthracen-1-yl group, 7-phenylanthracen-1-yl group, 8-phenylanthracen-1-yl group, 9-phenylanthracen-1-yl group, 10-phenylanthracen-1-yl group, 1-methylanthracen-2-yl group, 3-methylanthracen-2-yl group, 4-methylanthracen-2-yl group, 9-methylanthracen-2-yl group, 10-methylanthracen-2-yl group, 1-phenylanthracen-2-yl group, 3-phenylanthracen-2-yl group, 4-phenylanthracen-2-yl group, 5-phenylanthracen-2-yl group, 6-phenylanthracen-2-yl group, 7-phenylanthracen-2-yl group, 8-phenylanthracen-2-yl group, 9-phenylanthracen-2-yl group, 10-phenylanthracen-2-yl group, 2-methylanthracen-9-yl group, 3-methylanthracen-9-yl group, 4-methylanthracen-9-yl group, 10-methylanthracen-9-yl group, 2-phenylanthracen-9-yl group, 3-phenylanthracen-9-yl group, 4-phenylanthracen-9-yl group, 5-phenylanthracen-9-yl group, 6-phenylanthracen-9-yl group, 7-phenylanthracen-9-yl group, 8-phenylanthracen-9-yl group and 10-phenylanthracen-9-yl group.

Of these unsubstituted or substituted anthryl groups, 1-anthryl group, 2-anthryl group, 9-anthryl group, and 10-phenylanthracen-9-yl group are preferable in view of the performance thereof as a material for an organic electroluminescent device. 9-Anthryl group is especially preferable because of ease in synthesis.

As specific examples of the unsubstituted or substituted phenanthryl group represented by $Ar^4$, there can be mentioned 1-phenanthryl group, 2-phenanthryl group, 3-phenanthryl group and 4-phenanthryl group and 9-phenanthryl group; and phenanthryl groups substituted by an alkyl group having 1 to 4 carbon atoms or a phenyl group, such as 2-phenylphenanthren-1-yl group, 3-phenylphenanthren-1-yl group, 4-phenylphenanthren-1-yl group, 9-phenylphenanthren-1-yl group, 1-phenylphenanthren-2-yl group, 3-phenylphenanthren-2-yl group, 4-phenylphenanthren-2-yl group, 9-phenylphenanthren-2-yl group, 1-phenylphenanthren-3-yl group, 2-phenylphenanthren-3-yl group, 4-phenylphenanthren-3-yl group, 9-phenylphenanthren-3-yl group, 1-phenylphenanthren-4-yl group, 2-phenylphenanthren-4-yl group, 3-phenylphenanthren-4-yl group, 9-phenylphenanthren-4-yl group, 1-phenylphenanthren-9-yl group, 2-phenylphenanthren-9-yl group, 3-phenylphenanthren-9-yl group and 4-phenylphenanthren-9-yl group.

Of these unsubstituted or substituted phenanthryl groups, 1-phenanthryl group, 2-phenanthryl group, 3-phenanthryl group, 4-phenanthryl group and 9-phenanthryl group are preferable in view of the performance thereof as a material for an organic electroluminescent device. 9-Phenanthryl group is especially preferable because of ease in synthesis.

As specific examples of the unsubstituted or substituted fluorenyl group represented by $Ar^4$, there can be mentioned unsubstituted fluorenyl group; and fluorenyl groups substituted by an alkyl group having 1 to 4 carbon atoms or a phenyl group, such as 9,9-dimethylfluoren-1-yl group, 9,9-dimethylfluoren-2-yl group, 9,9-dimethylfluoren-3-yl group, 9,9-dimethylfluoren-4-yl group, 9,9-diphenylfluoren-1-yl group, 9,9-diphenylfluoren-2-yl group, 9,9-diphenylfluoren-3-yl group and 9,9-diphenylfluoren-4-yl group.

Of these unsubstituted or substituted fluorenyl groups, 9,9-dimethylfluoren-2-yl group, 9,9-dimethylfluoren-3-yl group and 9,9-diphenylfluoren-2-yl group are preferable in view of the performance thereof as a material for an organic electroluminescent device. 9,9-Dimethylfluoren-2-yl group is especially preferable because of ease in synthesis.

As specific examples of the unsubstituted or substituted benzofluorenyl group represented by $Ar^4$, there can be mentioned unsubstituted benzofluorenyl group; and benzofluorenyl groups substituted by an alkyl group having 1 to 4 carbon atoms or a phenyl group, such as 9,9-dimethylbenzo[a]fluoren-3-yl group, 9,9-dimethylbenzo[a]fluoren-4-yl group, 9,9-dimethylbenzo[a]fluoren-5-yl group, 9,9-dimethylbenzo[a]fluoren-6-yl group, 9,9-dimethylbenzo[a]fluoren-7-yl group, 9,9-dimethylbenzo[a]fluoren-8-yl group, 9,9-dimethylbenzo[b]fluoren-1-yl group, 9,9-dimethylbenzo[b]fluoren-4-yl group, 9,9-dimethylbenzo[b]fluoren-5-yl group, 9,9-dimethylbenzo[b]fluoren-6-yl group, 9,9-dimethylbenzo[b]fluoren-7-yl group, 9,9-dimethylbenzo[b]fluoren-8-yl group, 9,9-dimethylbenzo[c]fluoren-1-yl group, 9,9-dimethylbenzo[c]fluoren-2-yl group, 9,9-dimethylbenzo[c]fluoren-5-yl group, 9,9-dimethylbenzo[c]fluoren-6-yl group, 9,9-dimethylbenzo[c]fluoren-7-yl group, 9,9-dimethylbenzo[c]fluoren-8-yl group, 9,9-diphenylbenzo[a]fluoren-3-yl group, 9,9-diphenylbenzo[a]fluoren-4-yl group, 9,9-diphenylbenzo[a]fluoren-5-yl group, 9,9-diphenylbenzo[a]fluoren-6-yl group, 9,9-diphenylbenzo[a]fluoren-7-yl group, 9,9-diphenylbenzo[a]fluoren-8-yl group, 9,9-diphenylbenzo[b]fluoren-1-yl group, 9,9-diphenylbenzo[b]fluoren-4-yl group, 9,9-diphenylbenzo[b]fluoren-5-yl group, 9,9-diphenylbenzo[b]fluoren-6-yl group, 9,9-diphenylbenzo[b]fluoren-7-yl group, 9,9-diphenylbenzo[b]fluoren-8-yl group, 9,9-diphenylbenzo[c]fluoren-1-yl group, 9,9-diphenylbenzo[c]fluoren-2-yl group, 9,9-diphenylbenzo[c]fluoren-5-yl group, 9,9-diphenylbenzo[c]fluoren-6-yl group, 9,9-diphenylbenzo[c]fluoren-7-yl group and 9,9-diphenylbenzo[c]fluoren-8-yl group.

Of these unsubstituted or substituted benzofluorenyl groups, 9,9-dimethylbenzo[a]fluoren-6-yl group, 9,9-dimethylbenzo[a]fluoren-7-yl group, 9,9-dimethylbenzo[b]fluoren-6-yl group, 9,9-dimethylbenzo[b]fluoren-7-yl group, 9,9-dimethylbenzo[c]fluoren-2-yl group, 9,9-dimethylbenzo[c]fluoren-6-yl group and 9,9-dimethylbenzo[c]fluoren-7-yl group are preferable in view of the performance thereof as a material for an organic electroluminescent device. 9,9-Dimethylbenzo[c]fluoren-2-yl group is especially preferable because of ease in synthesis.

As specific examples of the unsubstituted or substituted pyrenyl group represented by $Ar^4$, there can be mentioned 1-pyrenyl group, 6-phenylpyren-1-yl group, 7-phenylpyren-1-yl group, 8-phenylpyren-1-yl group, 2-pyrenyl group, 6-phenylpyren-2-yl group, 7-phenylpyren-2-yl group and 8-phenylpyren-2-yl group.

Of these unsubstituted or substituted pyrenyl groups, 1-pyrenyl group and 2-pyrenyl group are preferable in view of the performance thereof as a material for an organic electroluminescent device. 2-Pyrenyl group is especially preferable because of ease in synthesis.

As specific examples of the unsubstituted or substituted triphenylenyl group represented by $Ar^4$, 1-triphenylenyl group and 2-triphenylenyl group are mentioned.

In the general formulae (3) and (11), X represents a phenylene group or a pyridylene group.

The compound represented by the general formula (11) can be produced, for example, by a process described in JP 2008-280330A, paragraphs [0061]-[0076]. As specific examples of the compound of the formulae (11), the following compounds (11-1) through (11-79) are mentioned, but the compounds used in the present invention should not be limited thereto.

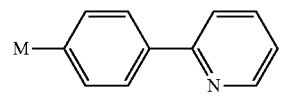

11-1

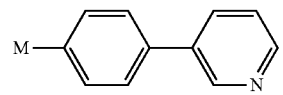

11-2

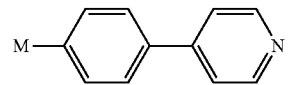

11-3

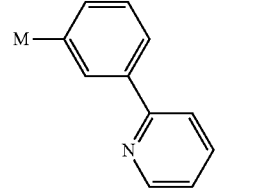

11-4

-continued
11-5 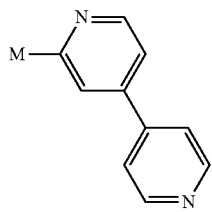
11-6 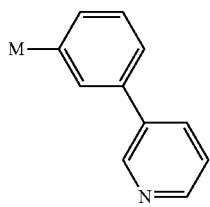
11-12 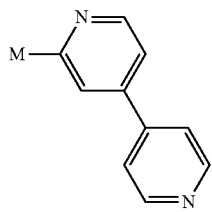
11-13 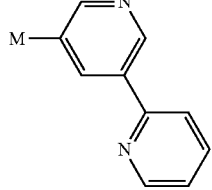
11-7 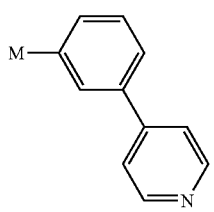
11-14 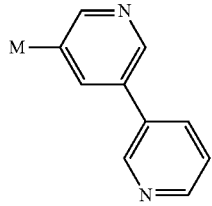
11-8 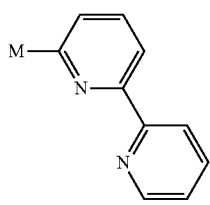
11-15 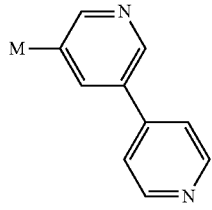
11-9 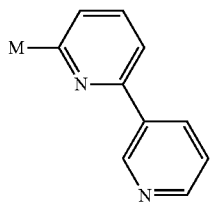
11-16 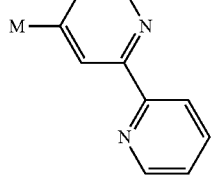
11-17 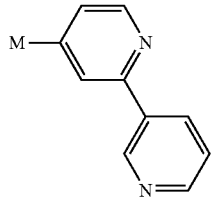
11-10 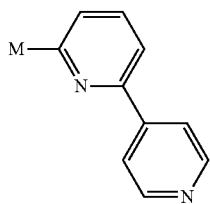
11-18 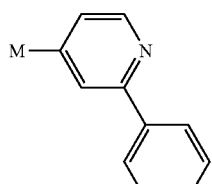
11-11 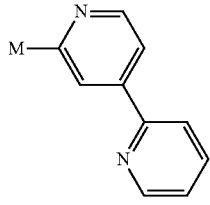
11-19 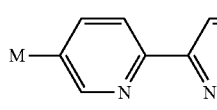
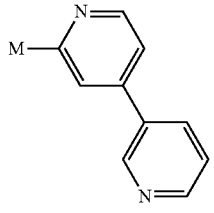

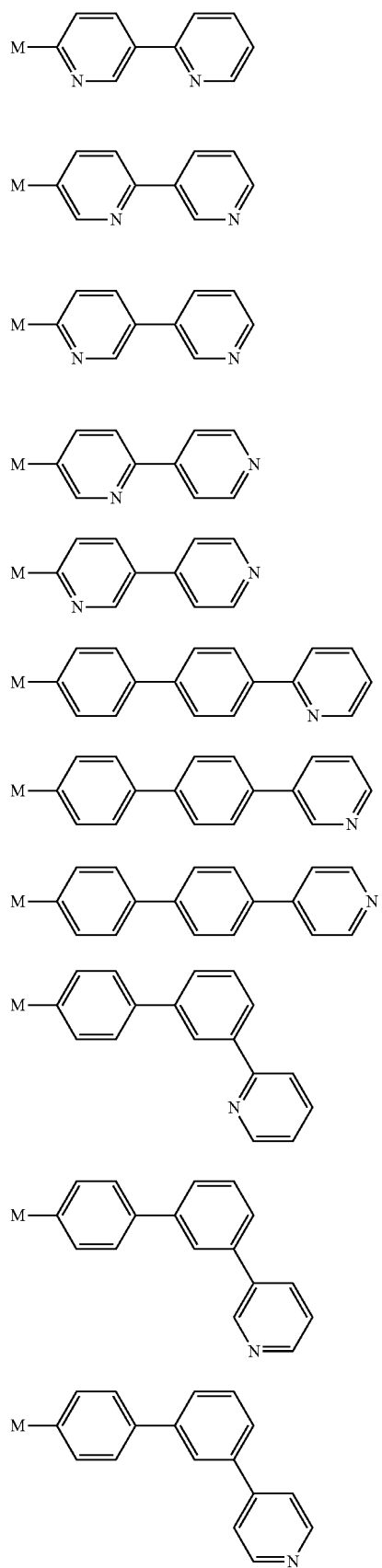
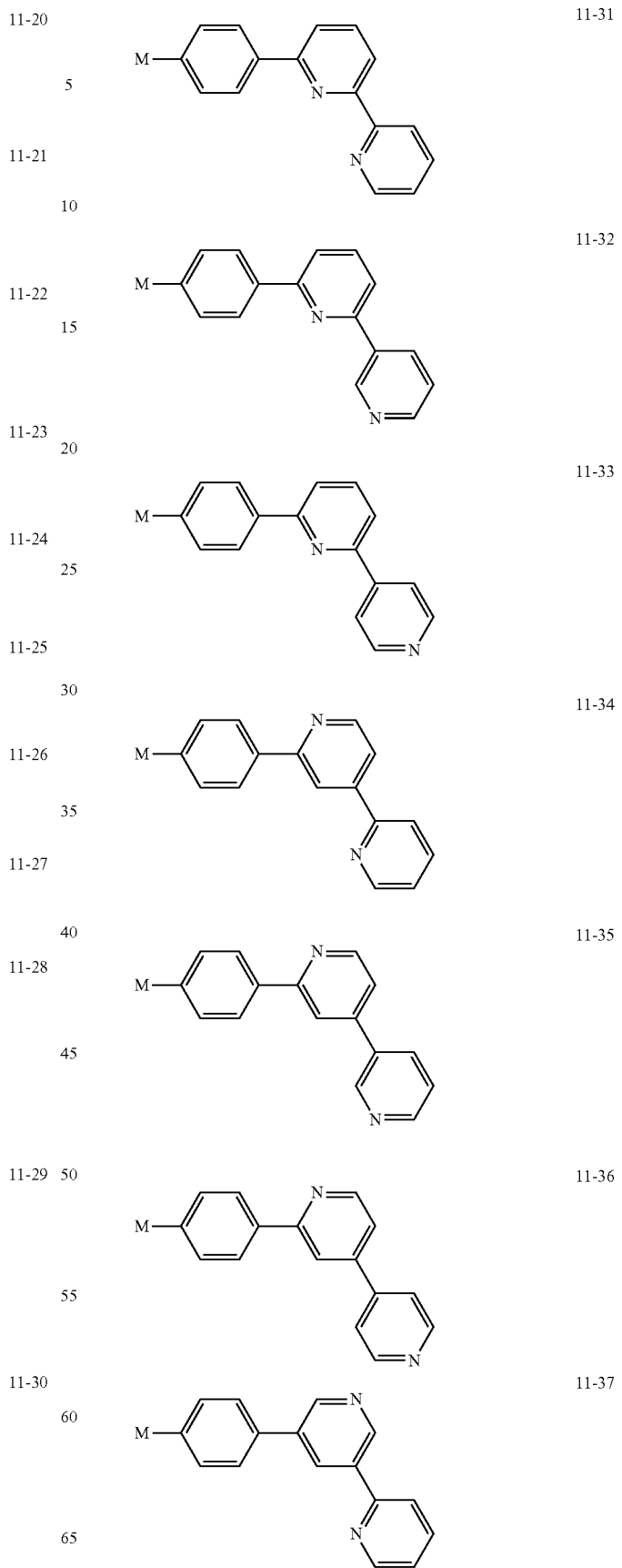

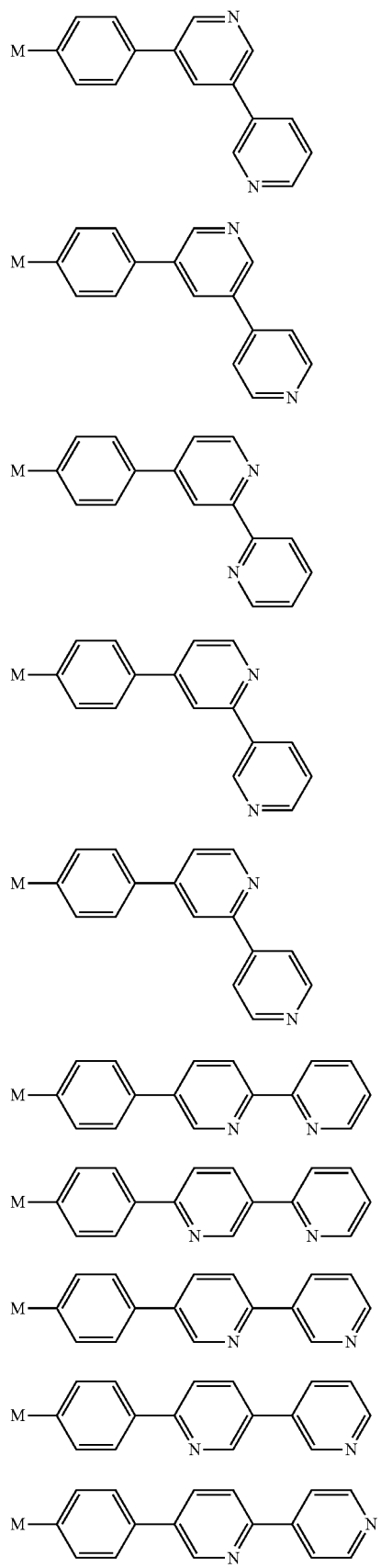
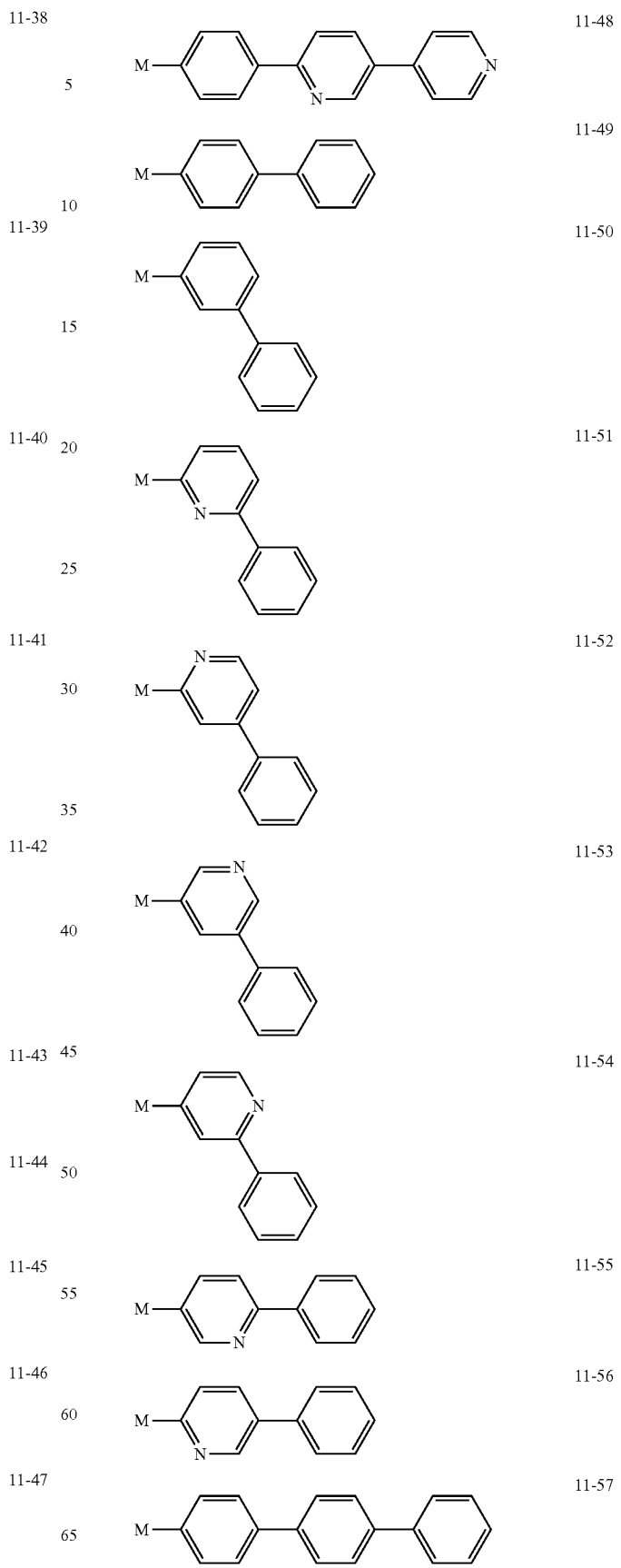

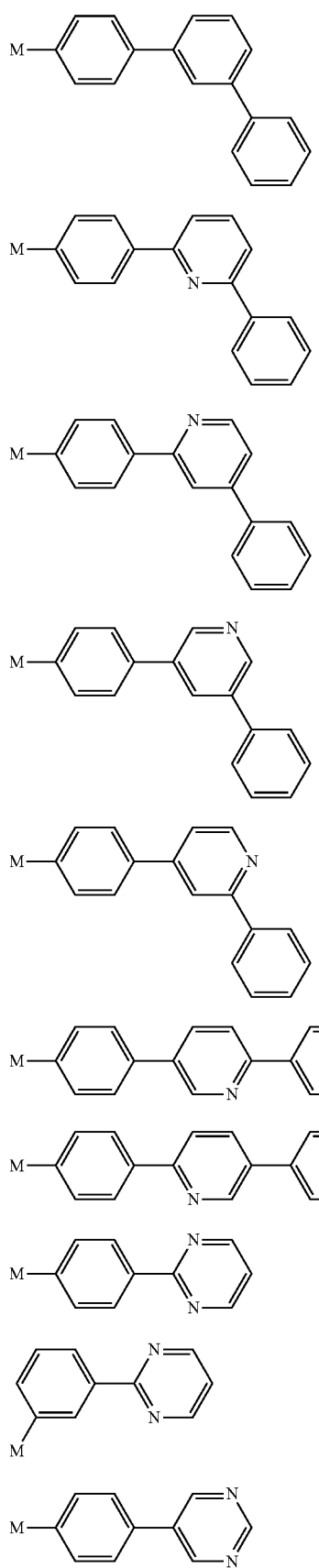
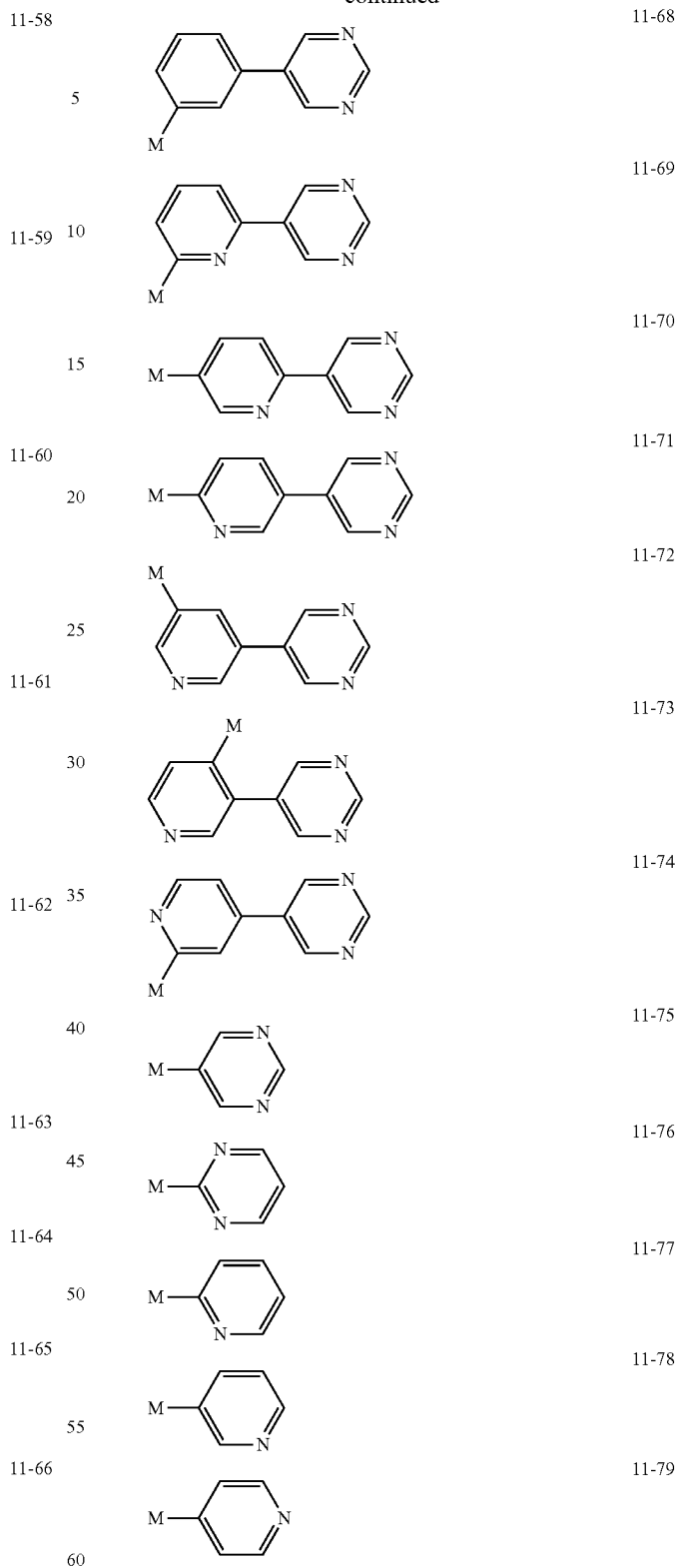
A representative category of the azine compound according to the present invention is a compound represented by the above-mentioned general formula (1c). The compound of the formula (1c) has substituents, represented by the following general formula (13a), on a benzene ring of the compound of the formula (1c).

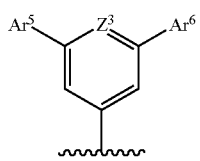
(13a)

wherein $Ar^5$ and $Ar^6$ represent a phenyl group or a pyridyl group, and $Z^3$ represents a carbon or nitrogen atom, provided that, when $Z^3$ represents a carbon atom, $Ar^5$ and $Ar^6$ cannot be simultaneously a phenyl group. As specific examples of the substituents of the formula (13a), the following groups (13a-1) through (13a-19) are mentioned, but the substituents of the formula (13a) used in the present invention should not be limited thereto.

13a-1

13a-2

13a-3

13a-4

13a-5

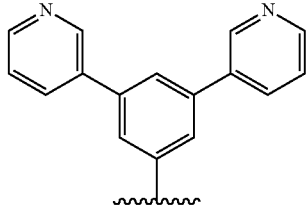
13a-6

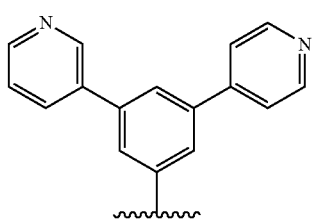
13a-7

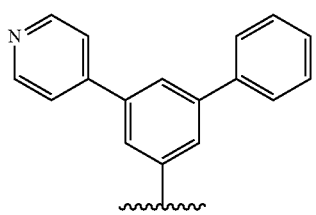
13a-8

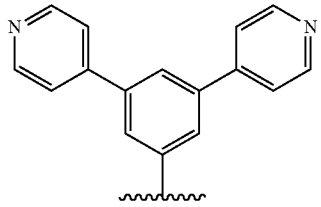
13a-9

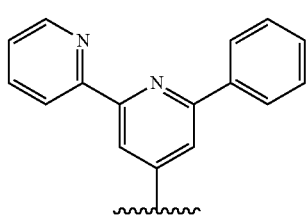
13a-10

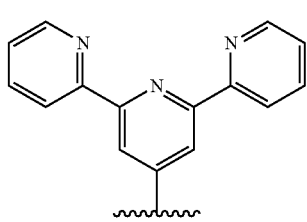
13a-11

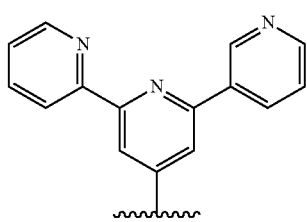
13a-12

-continued 13a-13
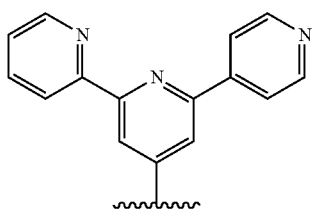

13a-14
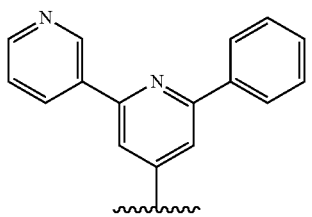

13a-15
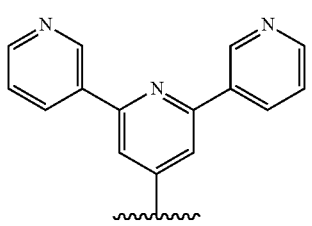

13a-16
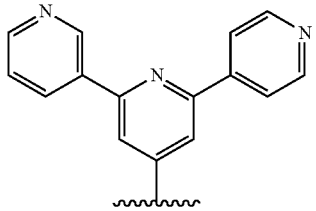

13a-17
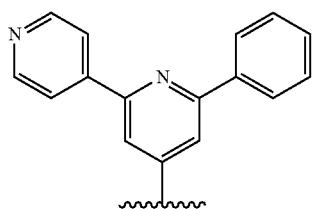

13a-18
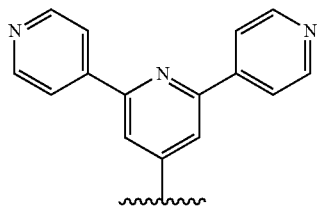

13a-19
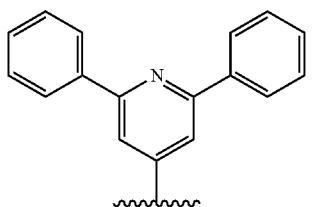

The metal group represented by M in the formulae (7) and (11) is not particularly limited, and those which are conventionally used in the general coupling reaction can be used. The metal group includes, for example, Li, Na, MgCl, MgBr, MgI, CuCl, CuBr, CuI, AlCl$_2$, AlBr$_2$, Al(Me)$_2$, Al(Et)$_2$, Al($^i$Bu)$_2$, Sn(Me)$_3$, Sn(Bu)$_3$, ZnR$^2$ where ZnR$^2$ includes, for example, ZnCl, ZnBr and ZnI.

Of these metal groups, ZnCl is preferable in view of high reaction yield. ZnCl coordinated with tetramethylethylenediamine (TMADA) is especially preferable.

The hetero atom group represented by M includes, for example, Si(Ph)$_3$, SnF$_3$, and B(OR$^2$)$_2$ where B(OR$^1$)$_2$ includes, for example, B(OMe)$_2$, B(O$^i$Pr)$_2$, B(OBu)$_2$ and B(OPh)$_2$. The two R$^1$s in B(OR$^1$)$_2$ may form a ring together with the oxygen atom and the boron atom, thus, B(OR$^1$)$_2$ forms the following groups (I) to (VI), for example. Of these groups (I) to (VI), group (II) is preferable in view of high reaction yield.

(I)

(II)
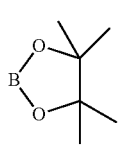

(III)
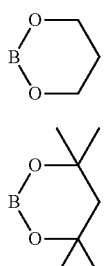

(IV)
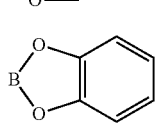

(V)
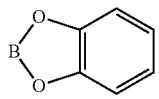

(VI)
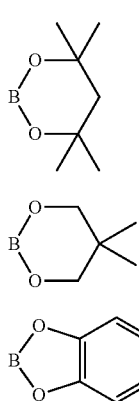

The azine derivative of the formula (1a) according to the present invention can be prepared by a process comprising a step 1 involving the following reaction scheme.

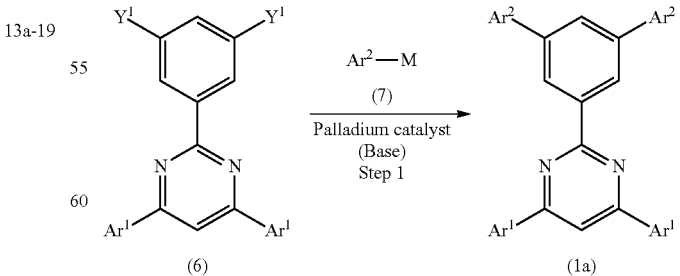

In the reaction scheme of step 1, each Ar$^1$ represents an aromatic group, which is unsubstituted or substituted by an alkyl group having 1 to 4 carbon atoms, a phenyl group or a pyridyl group; and each Ar² represents a substituted phenyl group or a condensed aromatic hydrocarbon group not having a 16 group element, provided that a 1,3,5-trimethylphenyl group is excluded from Ar². Each Y¹ represents a chlorine, bromine or iodine atom. M represents a metal group or a hetero atom group.

The step 1 is a step of reacting the compound of formula (6) with the compound of formula (7) in the presence of a palladium catalyst and in the presence or absence of a base to prepare the cyclic azine derivative (1a) according to the present invention. This coupling reaction can be effected by adopting conventional reaction conditions, which are adopted in the conventional coupling reactions such as, for example, Suzuki-Miyaura reaction, Negishi reaction, Tamao-Kumada reaction and Stille reaction. The target compound can be obtained with a high yield by adopting such reaction conditions.

The palladium catalyst used in the step 1 includes, for example, palladium salts such as palladium chloride, palladium acetate, palladium trifluoroacetate and palladium nitrate; and complex compounds such as π-allylpalladium chloride dimmer, palladium acetylacetonate, tris(dibenzylideneacetone)dipalladium, dichlorobis(triphenylphosphine)palladium, tetrakis(triphenylphosphine)palladium and dichloro[1,1'-bis(diphenylphosphino)ferrocene]palladium.

Of these, palladium complex compounds having a tertiary phosphine as a ligand are preferable because of high reaction yield. Palladium complex compounds having a triphenylphosphine as a ligand are especially preferable because they are readily available and give high reaction yield.

The molar ratio of the palladium catalyst to the compound of formula (6) is preferably in the range of 1:200 to 1:2, and more preferably 1:50 to 1:10 because of high reaction yield.

Palladium complex compounds having a tertiary phosphine as a ligand can also be synthesized in a reaction system containing a palladium salt or a palladium complex compound and a tertiary phosphine added therein.

As specific examples of the tertiary phosphine used, there can be mentioned triphenylphosphine, trimethylphosphine, tributylphosphine, tri(tert-butyl)phosphine, tricyclohexylphosphine, tert-butyldiphenylphosphine, 9,9-dimethyl-4,5-bis(diphenylphosphino)xanthene, 2-(diphenylphosphino)-2'-(N,N-dimethylamino)biphenyl, 2-(di-tert-butylphosphino) biphenyl, 2-(dicyclohexylphosphino)-biphenyl, bis(diphenylphosphino)methane, 1,2-bis(diphenylphosphino) ethane, 1,3-bis(diphenylphosphino)-propane, 1,4-bis (diphenylphosphino)butane, 1,1'-bis(diphenylphosphino) ferrocene, tri-(2-furyl)phosphine, tri-(o-tolyl)phosphine, tris (2,5-xylyl)phosphine, (±)-2,2'-bis(diphenylphosphino)-1,1'-binaphthyl and 2-dicyclohexylphosphino-2',4',6'-triisopropylbiphenyl.

Of these, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

The molar ratio of the compound of formula (6) to the compound of formula (7), which are used in the step 1, is preferably in the range of 1:2 to 5:1, and more preferably 1:2 to 2:1 because of high yield.

In the case when the step 1 is carried out according to Suzuki-Miyaura reaction using the compound of the formula (7) wherein M is B(OR¹)₂, the reaction yield can be enhanced by carrying out the reaction in the presence of a base.

The base capable of being used in the step 1 includes, for example, sodium hydroxide, potassium hydroxide, sodium carbonate, potassium carbonate, lithium carbonate, cesium carbonate, potassium phosphate, sodium phosphate, sodium fluoride, potassium fluoride and cesium fluoride. Of these, cesium carbonate is preferable because of high reaction yield. The molar ratio of the base to the compound of formula (7) is preferably in the range of 1:2 to 10:1, and more preferably 1:1 to 3:1 because of high reaction yield.

The reaction in the step 1 can be effected in a reaction medium. The reaction medium used in the step 1 includes, for example, water, dimethylsulfoxide, dimethylformamide, tetrahydrofuran, toluene, benzene, diethyl ether, ethanol, methanol and xylene. These reaction mediums may be used either alone or in combination. Of these, toluene and tetrahydrofuran are preferable because of high reaction yield.

The reaction in the step 1 can be effected at a temperature appropriately chosen in a range of 0° C. to 150° C. A temperature of 40° C. to 110° C. is especially preferable because of high reaction yield.

The cyclic azine compound of formula (1a) according to the present invention can be obtained by conducting the conventional treating procedure after completion of the step 1. If desired, the produced compound is purified by, for example, recrystallization, column chromatography or sublimation.

The cyclic azine compound of formula (1a) according to the present invention can also be prepared by a process comprising a step 2 involving the following reaction scheme.

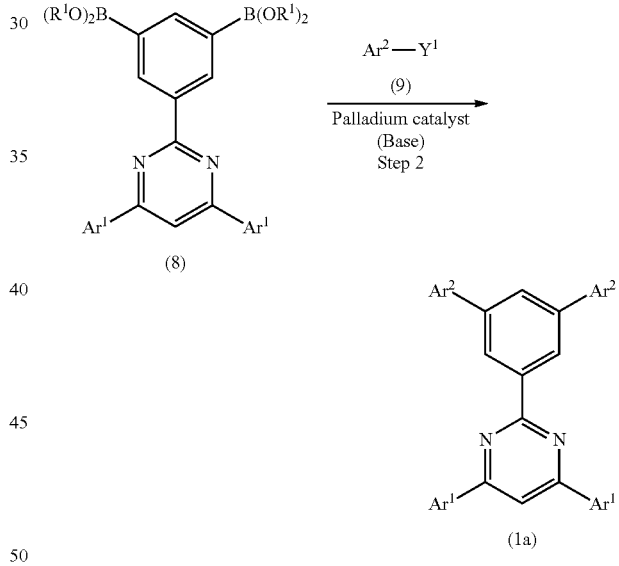

In the reaction scheme of step 2, each Ar¹ represents an aromatic group, which is unsubstituted or substituted by an alkyl group having 1 to 4 carbon atoms, a phenyl group or a pyridyl group; and each Ar² represents a substituted phenyl group or a condensed aromatic hydrocarbon group not having a 16 group element, provided that a 1,3,5-trimethylphenyl group is excluded from Ar². Y¹ represents a chlorine, bromine or iodine atom. Each R¹ represents a hydrogen atom, an alkyl group having 1 to 4 carbon atoms or a phenyl group; and groups R¹ in the two —B(OR¹) groups may be the same or different, and two groups R¹ in each of the two —B(OR¹) groups may form a ring together with the oxygen atoms and the boron atom.

The step 2 is a step of reacting the compound of formula (8) with the compound of formula (9) in the presence of a palladium catalyst and a base to prepare the cyclic azine compound of formula (1a) according to the present invention. This coupling reaction can be effected by adopting conventional reaction conditions adopted in the conventional Suzuki-Miyaura reaction. The target compound can be obtained with a high yield by adopting such reaction conditions.

The palladium catalyst used in the step 2 includes, for example, palladium salts and complex compounds, which are exemplified with regard to the palladium catalyst used in the step 1. Of these catalysts, palladium complex compounds having a tertiary phosphine as a ligand are preferable because of high reaction yield. Palladium complex compounds having a triphenylphosphine as a ligand are especially preferable in view of ease in availability and high reaction yield.

The molar ratio of the palladium catalyst to the compound of formula (8) is preferably in the range of 1:200 to 1:2, and more preferably 1:50 to 1:10 because of high reaction yield.

Palladium complex compounds having a tertiary phosphine as a ligand can also be synthesized in a reaction system containing a palladium salt or a palladium complex compound and a tertiary phosphine added therein.

As specific examples of the tertiary phosphine used, those which are exemplified with regard to the step 1 can be mentioned. Of these tertiary phosphines, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

It is essential to carry out the step 2 in the presence of a base. The base used in the step 2 includes, for example, sodium hydroxide, potassium hydroxide, sodium carbonate, potassium carbonate, lithium carbonate, cesium carbonate, potassium phosphate, sodium phosphate, sodium fluoride, potassium fluoride and cesium fluoride. Of these, cesium carbonate is preferable because of high reaction yield. The molar ratio of the base to the compound of formula (8) is preferably in the range of 1:2 to 10:1, and more preferably 1:1 to 4:1 because of high reaction yield.

The molar ratio of the compound of formula (8) to the compound of formula (9), which are used in the step 2, is preferably in the range of 1:10 to 2:1, and more preferably 1:2 to 1:4 because of high yield.

The reaction in the step 2 can be effected in a reaction medium. The reaction medium used in the step 2 includes, for example, water, dimethylsulfoxide, dimethylformamide, tetrahydrofuran, toluene, benzene, diethyl ether, ethanol, methanol and xylene. These reaction mediums may be used either alone or in combination. Of these, a mixed medium of toluene with water is preferable because of high reaction yield.

The reaction in the step 2 can be effected at a temperature appropriately chosen in a range of 0° C. to 150° C. A temperature of 40° C. to 110° C. is especially preferable because of high reaction yield.

The cyclic azine compound of formula (1a) according to the present invention can be obtained by conducting the conventional treating procedure after completion of the step 2. If desired, the produced compound is purified by, for example, recrystallization, column chromatography or sublimation.

The compound of formula (8), which is a raw material for preparing the cyclic azine compound of formula (1a) according to the present invention by the step 2, can be prepared, for example, by a process comprising a step 3 involving the following reaction scheme.

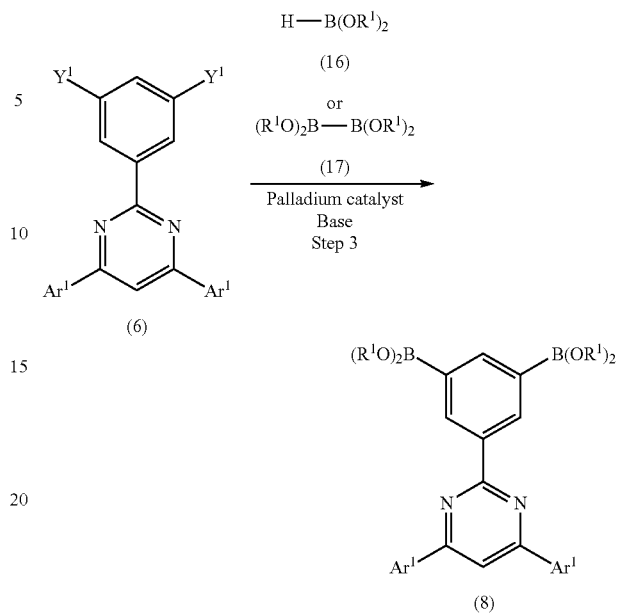

In the reaction scheme of step 3, each $Ar^1$ represents an aromatic group, which is unsubstituted or substituted by an alkyl group having 1 to 4 carbon atoms, a phenyl group or a pyridyl group; each $R^1$ represents a hydrogen atom, an alkyl group having 1 to 4 carbon atoms or a phenyl group; and groups $R^1$ in the two —$B(OR^1)$ groups may be the same or different, and two groups $R^1$ in each of the two —$B(OR^1)$ groups may form a ring together with the oxygen atoms and the boron atom. $Y^1$ represents a chlorine, bromine or iodine atom.

The step 3 is a step of reacting a compound of the formula (6) with a borane compound of the general formula (16) or a diborane compound of the general formula (17) in the presence of a palladium catalyst and a base to give the compound of the formula (8) used in the step 2. This reaction can be effected with a high reaction yield of the target compound by adopting reaction conditions, which are described in The Journal of Organic Chemistry, vol. 60, 7508-7510, 1995, or The Journal of Organic Chemistry, vol. 65, 164-168, 2000.

The palladium catalyst used in the step 3 includes, for example, palladium salts and complex compounds, which are exemplified with regard to the palladium catalyst used in the step 1. Of these catalysts, palladium complex compounds having a tertiary phosphine as a ligand are preferable because of high reaction yield. Palladium complex compounds having a triphenylphosphine as a ligand are especially preferable in view of ease in availability and high reaction yield.

The molar ratio of the palladium catalyst to the compound of formula (6) is preferably in the range of 1:200 to 1:2, and more preferably 1:50 to 1:10 because of high reaction yield.

Palladium complex compounds having a tertiary phosphine as a ligand can also be synthesized in a reaction system containing a palladium salt or a palladium complex compound and a tertiary phosphine added therein.

As specific examples of the tertiary phosphine used, those which are exemplified with regard to the step 1 can be mentioned. Of these tertiary phosphines, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

It is essential to carry out the step 3 in the presence of a base. The base used in the step 3 includes, for example, sodium hydroxide, potassium hydroxide, sodium carbonate, potassium carbonate, lithium carbonate, cesium carbonate, potassium phosphate, sodium phosphate, sodium fluoride, potassium fluoride and cesium fluoride. Of these, cesium carbonate is preferable because of high reaction yield. The molar ratio of the base to the compound of formula (6) is preferably in the range of 1:2 to 10:1, and more preferably 2:1 to 4:1 because of high reaction yield.

The molar ratio of the borane compound of formula (16) or the diborane compound of formula (17) to the compound of formula (6), which are used in the step 3, is preferably in the range of 1:1 to 5:1, and more preferably 2:1 to 3:1 because of high yield.

The reaction in the step 3 can be effected in a reaction medium. The reaction medium used in the step 3 includes, for example, water, dimethylsulfoxide, dimethylformamide, tetrahydrofuran, toluene, benzene, diethyl ether, ethanol, methanol and xylene. These reaction mediums may be used either alone or in combination. Of these, tetrahydrofuran is preferable because of high reaction yield.

The reaction in the step 3 can be effected at a temperature appropriately chosen in a range of 0° C. to 150° C. A temperature of 40° C. to 80° C. is especially preferable because of high reaction yield.

The compound of formula (8) obtained in the step 3 may be isolated after completion of the reaction. Alternatively the compound of formula (8) may be used as a raw material in the step (2).

The cyclic azine compound of the formula (1b) according to the present invention can also be prepared by a process comprising a step 4 involving the following reaction scheme.

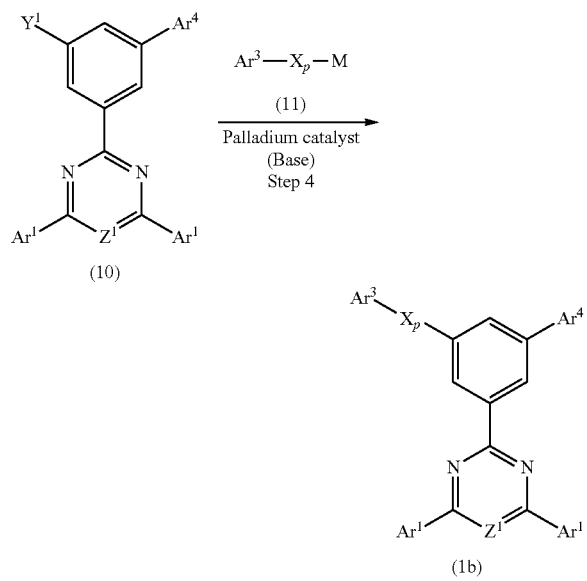

In the reaction scheme in the step 4, each $Ar^1$ represents an aromatic group, which is unsubstituted or substituted by an alkyl group having 1 to 4 carbon atoms, a phenyl group or a pyridyl group; and $Ar^4$ represents a substituted or unsubstituted aromatic hydrocarbon group having 2 to 4 rings. $Z^1$ represents a carbon or nitrogen atom; and $Y^1$ represents a chlorine, bromine or iodine atom. $Ar^3$ represents a phenyl group, a pyridyl group or a pyrimidinyl group. X represents a phenylene group or a pyridylene group. p represents an integer of 0 to 2 provided that, when p is 2, the two Xs may be the same or different. M represents a metal group or a hetero atomic group.

The step 4 is a step of reacting the compound of formula (10) with the compound of formula (11) in the presence of a palladium catalyst and in the presence or absence of a base to prepare the cyclic azine compound of formula (1b) according to the present invention. This reaction can be effected by adopting conventional reaction conditions, which are adopted in the conventional coupling reactions such as, for example, Suzuki-Miyaura reaction, Negishi reaction, Tamao-Kumada reaction and Stille reaction. The target compound can be obtained with a high yield by adopting such reaction conditions.

The palladium catalyst used in the step 4 includes, for example, palladium salts and complex compounds, which are exemplified with regard to the palladium catalyst used in the step 1. Of these catalysts, palladium complex compounds having a tertiary phosphine as a ligand are preferable because of high reaction yield. Palladium complex compounds having a triphenylphosphine as a ligand are especially preferable in view of ease in availability and high reaction yield.

Palladium complex compounds having a tertiary phosphine as a ligand can also be synthesized in a reaction system containing a palladium salt or a palladium complex compound and a tertiary phosphine added therein.

As specific examples of the tertiary phosphine used, those which are exemplified with regard to the step 1 can be mentioned. Of these tertiary phosphines, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

The base capable of being used in the step 2 includes, for example, sodium hydroxide, potassium hydroxide, sodium carbonate, potassium carbonate, lithium carbonate, cesium carbonate, potassium phosphate, sodium phosphate, sodium fluoride, potassium fluoride and cesium fluoride. Of these, cesium carbonate is preferable because of high reaction yield. The molar ratio of the base to the compound of formula (11) is preferably in the range of 1:2 to 10:1, and more preferably 1:1 to 3:1 because of high reaction yield.

The molar ratio of the compound of formula (10) to the compound of formula (11), which are used in the step 4, is preferably in the range of 1:2 to 5:1, and more preferably 1:2 to 2:1 because of high yield.

The reaction medium used in the step 4 includes, for example, water, dimethylsulfoxide, dimethylformamide, tetrahydrofuran, toluene, benzene, diethyl ether, ethanol, methanol and xylene. These reaction mediums may be used either alone or in combination. Of these, a mixed medium of toluene with ethanol is preferable because of high reaction yield.

The reaction in the step 4 can be effected at a temperature appropriately chosen in a range of 0° C. to 150° C. A temperature of 40° C. to 80° C. is especially preferable because of high reaction yield.

The cyclic azine compound of formula (1b) according to the present invention can be obtained by conducting the conventional treating procedure after completion of the step 4. If desired, the produced compound is purified by, for example, recrystallization, column chromatography or sublimation.

The compound of formula (10) used for the preparation of the cyclic azine compound of formula (1b) according to the present invention can be prepared by a process comprising a step 5 involving the following reaction scheme.

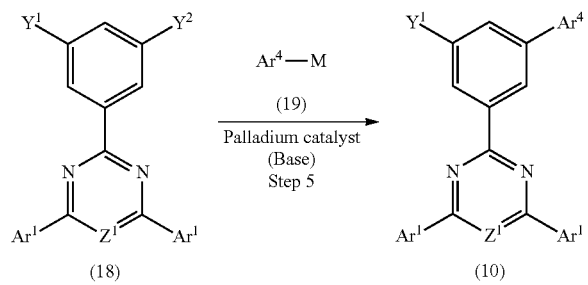

In the reaction scheme in the step 5, each $Ar^1$ represents an aromatic group, which is unsubstituted or substituted by an alkyl group having 1 to 4 carbon atoms, a phenyl group or a pyridyl group; and $Ar^4$ represents a substituted or unsubstituted aromatic hydrocarbon group having 2 to 4 rings. $Z^1$ represents a carbon or nitrogen atom; and $Y^1$ and $Y^2$ represent a chlorine, bromine or iodine atom. M represents a metal group or a hetero atomic group.

The step 5 is a step of reacting the compound of formula (18) with the compound of formula (19) in the presence of a palladium catalyst and in the presence or absence of a base to prepare the compound of formula (10) used for the preparation of the cyclic azine compound of formula (1b) according to the present invention. This reaction can be effected by adopting conventional reaction conditions, which are adopted in the conventional coupling reactions such as, for example, Suzuki-Miyaura reaction, Negishi reaction, Tamao-Kumada reaction and Stille reaction. The target compound can be obtained with a high yield by adopting such reaction conditions.

The palladium catalyst used in the step 5 includes, for example, palladium salts and complex compounds, which are exemplified with regard to the palladium catalyst used in the step 1. Of these catalysts, palladium complex compounds having a tertiary phosphine as a ligand are preferable because of high reaction yield. Palladium complex compounds having a triphenylphosphine as a ligand are especially preferable in view of ease in availability and high reaction yield.

Palladium complex compounds having a tertiary phosphine as a ligand can also be synthesized in a reaction system containing a palladium salt or a palladium complex compound and a tertiary phosphine added therein.

As specific examples of the tertiary phosphine used, those which are exemplified with regard to the step 1 can be mentioned. Of these tertiary phosphines, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

The base capable of being used in the step 5 includes, for example, those which are exemplified with regard to the step 1. Of these, potassium carbonate is preferable because of high reaction yield. The molar ratio of the base to the compound of formula (19) is preferably in the range of 1:1 to 10:1, and more preferably 2:1 to 3:1 because of high reaction yield.

The molar ratio of the compound of formula (18) to the compound of formula (19), which are used in the step 5, is preferably in the range of 1:2 to 5:1, and more preferably 1:2 to 2:1 because of high yield.

The reaction medium used in the step 5 includes, for example, water, dimethylsulfoxide, dimethylformamide, tetrahydrofuran, toluene, benzene, diethyl ether, ethanol, methanol and xylene. These reaction mediums may be used either alone or in combination. Of these, a mixed medium of toluene with ethanol is preferable because of high reaction yield.

The reaction in the step 5 can be effected at a temperature appropriately chosen in a range of 0° C. to 150° C. A temperature of 40° C. to 80° C. is especially preferable because of high reaction yield.

The compound of formula (10) can be obtained by conducting the conventional treating procedure after completion of the step 5. If desired, the produced compound is purified by, for example, recrystallization, column chromatography or sublimation.

The cyclic azine compound of formula (1c) according to the present invention can be prepared, for example, by a process comprising a step 6 involving the following reaction scheme.

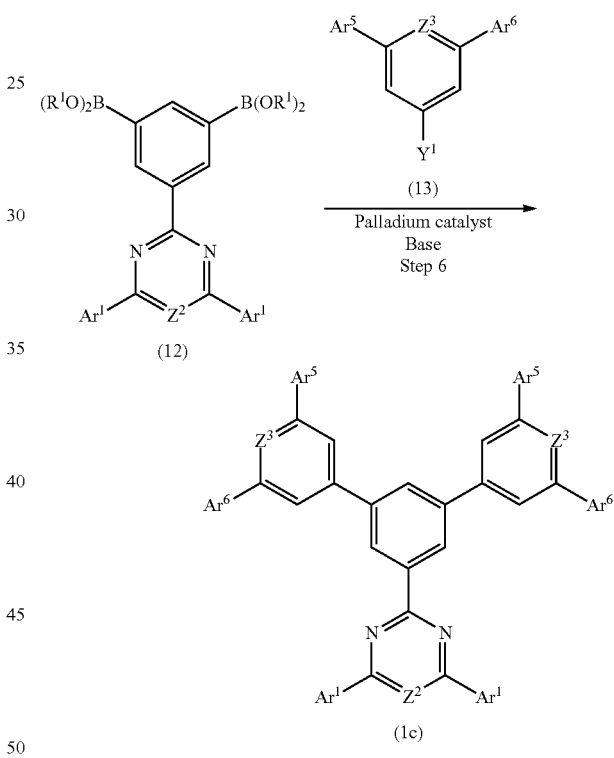

In the reaction scheme of step 6, each $Ar^1$ represents an aromatic group, which is unsubstituted or substituted by an alkyl group having 1 to 4 carbon atoms, a phenyl group or a pyridyl group. $Z^2$ represents a carbon or nitrogen atom. Each $R^1$ represents a hydrogen atom, an alkyl group having 1 to 4 carbon atoms or a phenyl group; and groups $R^1$ in the two —$B(OR^1)_2$ groups may be the same or different, and two groups $R^1$ in each of the two —$B(OR^1)_2$ groups may form a ring together with the oxygen atoms and the boron atom. Each $Ar^5$ and each $Ar^6$ represent a phenyl group or a pyridyl group; and each $Z^3$ represents a carbon or nitrogen atom, provided that, when each $Z^3$ represents a carbon atom, each $Ar^5$ and each $Ar^6$ cannot be simultaneously a phenyl group. $Y^1$ represents a chlorine, bromine or iodine atom.

The compound of formula (13) can be prepared by a process described in, for example, Dalton Trans., 4659-4665, 2007; JP 2002-363161A; or the process in Experiment Examples 42 and 43, described below.

As specific examples of the compound of formula (13), the following compounds 13-1 through 13-19 are mentioned, but the compound of formula (13) used in the present invention is not limited thereto. In the following chemical formulae of the compounds 13-1 through 13-19, $Y^1$ represents a chlorine, bromine or iodine atom.

13-14
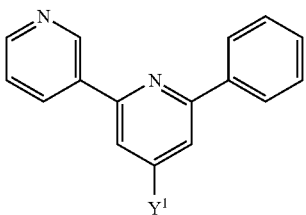

13-15
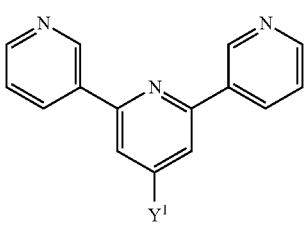

13-16
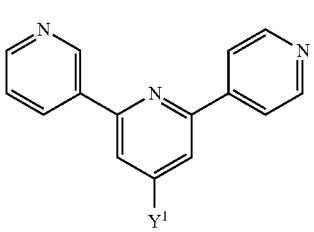

13-17
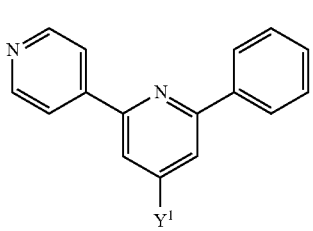

13-18
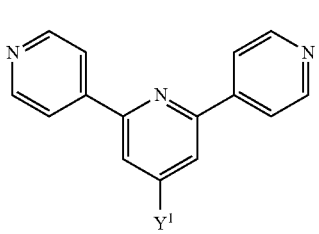

13-19
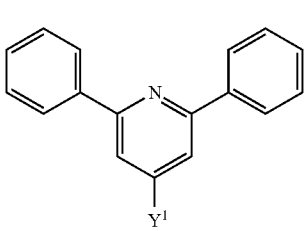

The step 6 is a step of reacting a compound of the formula (13) with a compound of the formula (12) in the presence of a palladium catalyst and a base to give the cyclic azine compound of formula (1c) according to the present invention. This reaction can be effected with a high reaction yield of the target compound by adopting reaction conditions, adopted in the conventional Suzuki-Miyaura reaction. The target compound can be obtained with a high yield by adopting such reaction conditions.

The palladium catalyst used in the step 6 includes, for example, palladium salts and complex compounds, which are exemplified with regard to the palladium catalyst used in the step 1. Of these catalysts, palladium complex compounds having a tertiary phosphine as a ligand are preferable because of high reaction yield. Palladium complex compounds having a triphenylphosphine as a ligand are especially preferable in view of ease in availability and high reaction yield.

The amount of the palladium catalyst used in the step 6 is not particularly limited, provided that it is a catalytical amount. The molar ratio of the palladium catalyst to the compound of formula (12) is preferably in the range of 1:50 to 1:10.

Palladium complex compounds having a tertiary phosphine as a ligand can also be synthesized in a reaction system containing a palladium salt or a palladium complex compound and a tertiary phosphine added therein.

As specific examples of the tertiary phosphine used, those which are exemplified with regard to the step 1 can be mentioned. Of these tertiary phosphines, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

It is essential to carry out the step 6 in the presence of a base. The base used in the step 6 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, sodium carbonate is preferable because of high reaction yield. The molar ratio of the base to the compound of formula (12) is not particularly limited, but is preferably in the range of 1:2 to 10:1, and more preferably 1:1 to 3:1 because of high reaction yield.

The molar ratio of the compound of formula (13) to the compound of formula (12), which are used in the step 6, is not particularly limited, but is preferably in the range of 1:1 to 5:1, and more preferably 2:1 to 3:1 because of high yield.

The reaction in the step 6 can be effected in a reaction medium. The reaction medium used includes, for example, water, dimethylsulfoxide, dimethylformamide, tetrahydrofuran, toluene, benzene, diethyl ether, ethanol, methanol and xylene. These reaction mediums may be used either alone or in combination. Of these, a mixed medium comprised of toluene and water is preferable because of high reaction yield.

The cyclic azine compound of formula (1c) according to the present invention can be obtained by conducting the conventional treating procedure after completion of the step 6. If desired, the produced compound is purified by, for example, recrystallization, column chromatography or sublimation.

The compound of formula (12) used as a raw material for the preparation of the cyclic azine derivative of formula (1c) of the present invention in the step 6 can be prepared by a process comprising a step 7 involving the following reaction scheme. Specific examples of the step 7 are shown, for example, in Experiment Examples 34 to 36.

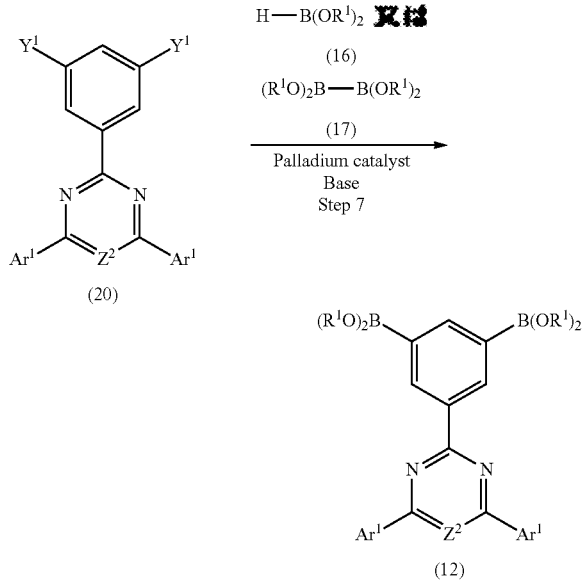

In the reaction scheme of step 7, each $Ar^1$ represents an aromatic group, which is unsubstituted or substituted by an alkyl group having 1 to 4 carbon atoms, a phenyl group or a pyridyl group. $Z^2$ represents a carbon or nitrogen atom. Each $R^1$ represents a hydrogen atom, an alkyl group having 1 to 4 carbon atoms or a phenyl group; and groups $R^1$ in the two $-B(OR^1)_2$ groups may be the same or different, and two groups $R^1$ in each of the two $-B(OR^1)_2$ groups may form a ring together with the oxygen atoms and the boron atom. $Y^1$ represents a chlorine, bromine or iodine atom.

The compound of formula (20) can be prepared by a process specifically described in, for example, Experiment Examples 37 to 42.

The step 7 is a step of reacting a compound of the formula (20) with a borane compound of the general formula (16) or a diborane compound of the general formula (17) in the presence of a palladium catalyst and a base to give the compound of the formula (12) used in the step 6. This reaction can be effected with a high reaction yield of the target compound by adopting reaction conditions, which are described in The Journal of Organic Chemistry, vol. 60, 7508-7510, 1995, or The Journal of Organic Chemistry, vol. 65, 164-168, 2000.

The palladium catalyst used in the step 7 includes, for example, palladium salts and complex compounds, which are exemplified with regard to the palladium catalyst used in the step 1. Of these catalysts, palladium complex compounds having a tertiary phosphine as a ligand are preferable because of high reaction yield. Palladium complex compounds having a triphenylphosphine as a ligand are especially preferable in view of ease in availability and high reaction yield.

The amount of the palladium catalyst used in the step 7 is not particularly limited, provided that it is a catalytical amount. The molar ratio of the palladium catalyst to the compound of formula (20) is preferably in the range of 1:50 to 1:10.

Palladium complex compounds having a tertiary phosphine as a ligand can also be synthesized in a reaction system containing a palladium salt or a palladium complex compound and a tertiary phosphine added therein.

As specific examples of the tertiary phosphine used, those which are exemplified with regard to the step 1 can be mentioned. Of these tertiary phosphines, triphenylphosphine is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

It is essential to carry out the step 7 in the presence of a base. The base used in the step 7 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, potassium acetate is preferable because of high reaction yield. The molar ratio of the base to the compound of formula (20) is not particularly limited, but is preferably in the range of 1:2 to 10:1, and more preferably 1:1 to 3:1 because of high reaction yield.

The molar ratio of the borane compound of formula (16) or the diborane compound of formula (17) to the compound of formula (20), which are used in the step 2, is not particularly limited, but is preferably in the range of 1:1 to 5:1, and more preferably 2:1 to 3:1 because of high yield.

The reaction in the step 7 can be effected in a reaction medium. The reaction medium used in the step 7 includes, for example, water, dimethylsulfoxide, dimethylformamide, tetrahydrofuran, 1,4-dioxane, toluene, benzene, diethyl ether, ethanol, methanol and xylene. These reaction mediums may be used either alone or in combination. Of these, tetrahydrofuran and 1,4-dioxane are preferable because of high reaction yield.

The compound of formula (12) obtained in the step 7 may be isolated after completion of the reaction. Alternatively the compound of formula (12) may be used as a raw material in the step (6).

The cyclic azine compound of formula (1d) according to the present invention can be prepared, for example, by a process comprising a step 8 involving the following reaction scheme.

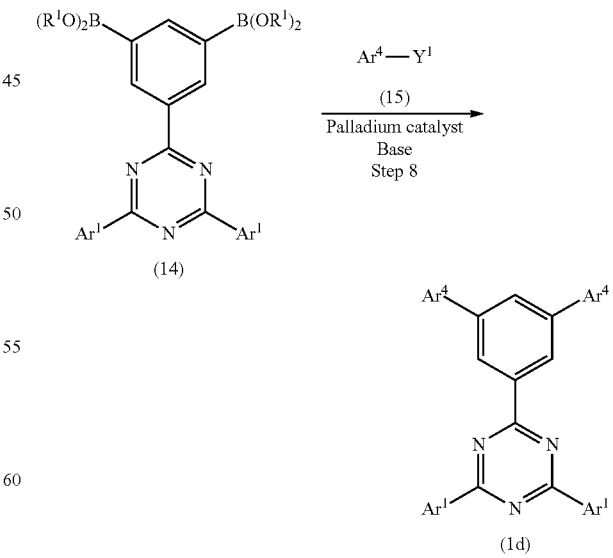

In the reaction scheme of step 8, each $Ar^1$ represents an aromatic group, which is unsubstituted or substituted by an alkyl group having 1 to 4 carbon atoms, a phenyl group or a pyridyl group. Each $R^1$ represents a hydrogen atom, an alkyl group having 1 to 4 carbon atoms or a phenyl group; and groups $R^1$ in the two $-B(OR^1)_2$ groups may be the same or different, and two groups $R^1$ in each of the two $-B(OR^1)_2$ groups may form a ring together with the oxygen atoms and the boron atom. Each $Ar^4$ represents an unsubstituted or substituted aromatic hydrocarbon group comprised of 2 to 4 rings. $Y^1$ represents a chlorine, bromine or iodine atom.

As preferable specific examples of the compound of formula (15), those which have the following skeletals 15-1 through 15-5 are mentioned, but the compound of formula (15) used in the present invention is not limited thereto.

15-1
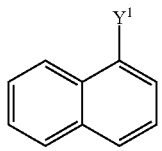

15-2
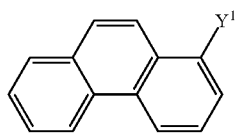

15-3
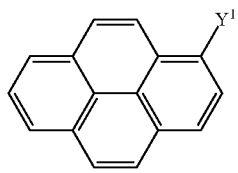

15-4
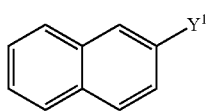

15-5
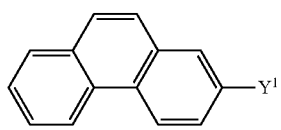

15-6
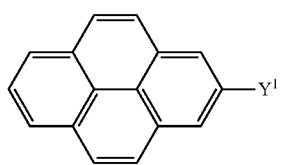

15-7
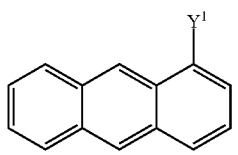

15-8
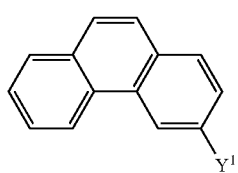

-continued 15-9
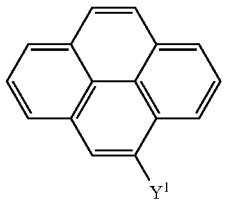

15-10
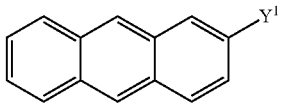

15-11
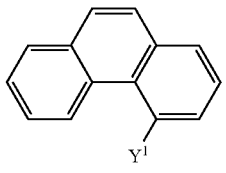

15-12
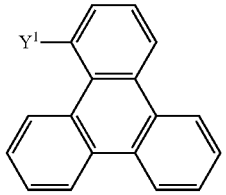

15-13
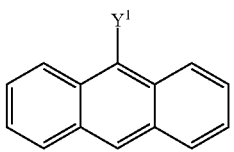

15-14
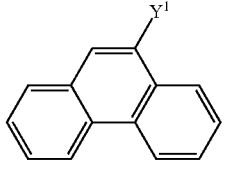

15-15
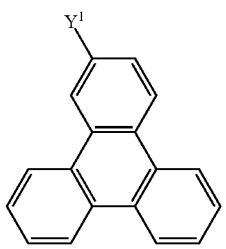

The step 8 is a step of reacting a compound of the formula (14) with a compound of the formula (15) in the presence of a palladium catalyst and a base to give the cyclic azine compound of formula (1d) according to the present invention. This reaction can be effected with a high reaction yield of the target compound by reaction conditions, which are adopted in the conventional Suzuki-Miyaura reaction. The target compound can be obtained with a high yield by adopting such reaction conditions.

The palladium catalyst used in the step 8 includes, for example, palladium catalysts, which are exemplified with regard to the palladium catalysts used in the step 1. Palladium chloride, palladium acetate, tris(dibenzylideneacetone)dipalladium, dichlorobis(triphenylphosphine)palladium, tetrakis(triphenylphosphine)palladium are preferable in view of ease in availability and good reaction yield.

These palladium catalysts can also be synthesized in a reaction system containing a palladium salt or a palladium complex compound and a tertiary phosphine added therein.

As specific examples of the tertiary phosphine added to a palladium salt or a palladium complex compound, those which are mentioned with regard to the step 1 are mentioned. Of these, triphenylphosphine, tri(tert-butyl)phosphine, 2-di(tert-butylphosphino)biphenyl, 2-dicylohexylphosphino-2',4',6'-triisopropylbiphenyl are preferable in view of ease in availability and good reaction yield.

The molar ratio of the palladium catalyst to the compound of formula (6) is preferably in the range of 1:200 to 1:2, and more preferably 1:100 to 1:10 in view of good reaction yield.

The molar ratio of the tertiary phosphine to the palladium catalyst is preferably in the range of 1/10 to 10/1, and more preferably 1/2 to 5/1 in view of good reaction yield.

The base used in the step 8 includes, for example, those which are exemplified with regard to the step 1. Of these, sodium hydroxide is especially preferable because of high reaction yield. The molar ratio of the base to the compound of formula (6) is preferably in the range of 1:2 to 10:1, and more preferably 1:1 to 3:1 because of high reaction yield.

The molar ratio of the compound of formula (15) to the compound of formula (14), which are used in the step 8, is preferably in the range of 2:1 to 5:1, and more preferably 2:1 to 3:1 because of high yield.

The reaction medium used in the step 8 includes, for example, water, dimethylsulfoxide, dimethylformamide, tetrahydrofuran, toluene, benzene, diethyl ether and xylene. These reaction mediums may be used either alone or in combination. Of these, tetrahydrofuran is preferable because of high reaction yield.

The reaction in the step 8 can be effected at a temperature appropriately chosen in a range of 0° C. to 150° C. A temperature of 50° C. to 80° C. is especially preferable because of high reaction yield.

The cyclic azine compound of formula (1d) of the present invention can be obtained by conducting the conventional treating procedure after completion of the step 8. If desired, the produced compound is purified by, for example, recrystallization, column chromatography or sublimation.

The compound of formula (14) used as a raw material for the preparation of the cyclic azine compound of formula (1d) of the present invention in the step 8 can be synthesized by the process of the step (7).

The process for producing a thin film of the cyclic azine compound of formula (1) according to the present invention for an organic EL device is not particularly limited. For example, vacuum deposition, spin coating, ink-jetting, casting and dipping can be adopted for the formation of the thin film. The vacuum deposition can be conducted using a conventional vacuum deposition apparatus. However, in consideration of the tact time and cost for the production of the organic EL device, the degree of vacuum at the vacuum deposition is preferably in the range of approximately $1\times10^{-2}$ Pa to $1\times10^{-5}$ Pa, which can be achieved, for example, by the conventionally used diffusion pump, turbo-molecular pump or cryopump. The rate of vacuum deposition varies depending upon the thickness of thin film, but the deposition rate is preferably in the range of 0.005 nm/sec to 1.0 nm/sec.

The solubility of the cyclic azine compound of formula (1) of the present invention in a solvent such as chloroform, dichloromethane, 1,2-dichloroethane, chlorobenzene, toluene, ethyl acetate and tetrahydrofuran is high. Therefore, the thin film can also be formed from a solution thereof by, for example, spin coating, ink jetting, casting or dipping using the conventional apparatus.

EXAMPLES

The invention will now be described more specifically by the following experiment examples and test examples, but the scope of the invention is by no means limited thereto.

Experiment Example 1

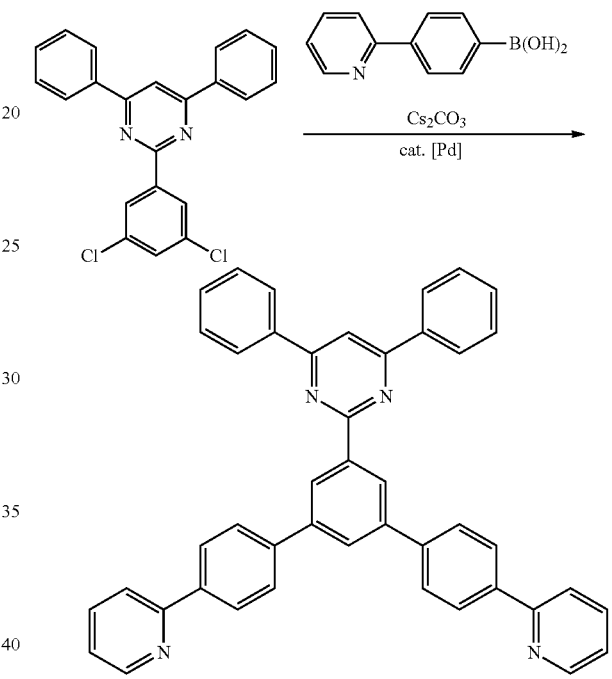

In a stream of argon, 1.50 g (3.98 mmol) of 2-(3,5-dichlorophenyl)-4,6-diphenylpyrimidine, 1.74 g (8.75 mmol) of 4-(2-pyridyl)phenylboronic acid, 2.85 g (8.75 mmol) of cesium carbonate, 36 mg (0.159 mmol) of palladium acetate and 152 mg (0.318 mmol) of 2-dicyclohexylphosphino-2',4',6'-triisopropylbiphenyl were suspended in 80 mL of 1,4-dioxane, and the obtained suspension was heated under reflux for 17 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using chloroform as an eluent to give 2.19 g of the target 2-[4,4''-di(2-pyridyl)-1,1':3',1''-terphenyl-5'-yl]-4,6-diphenylpyrimidine as a white solid (yield: 90%).

$^1$H-NMR (CDCl$_3$): δ7.19-7.23 (m, 2H), 7.53-7.50 (m, 6H), 7.70-7.79 (m, 4H), 7.88 (d, J=8.5 Hz, 4H), 8.01-8.02 (m, 2H), 8.11 (d, J=8.3 Hz, 4H), 8.25-8.29 (m, 4H), 8.68 (d, J=4.5 Hz, 2H), 8.95 (d, J=1.8 Hz, 2H).

$^{13}$C-NMR (CDCl$_3$): δ110.7 (CH), 120.5 (CH×2), 122.2 (CH×2), 126.6 (CH×2), 127.4 (CH×4), 127.5 (CH×4), 127.9 (CH×4), 128.2 (CH), 129.0 (CH×4), 130.9 (CH×2), 136.8

(CH×2), 137.5 (quart.×2), 138.7 (quart.×2), 139.5 (quart.), 141.6 (quart.), 141.8 (quart.), 149.9 (CH×2), 157.1 (quart.), 164.4 (CH), 165.0 (CH×2).

Experiment Example 2

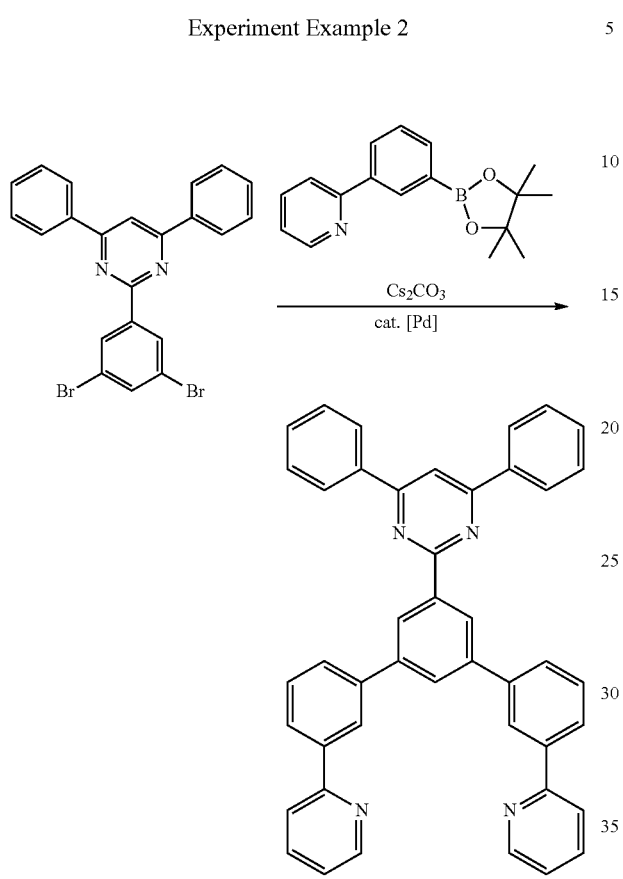

In a stream of argon, 1.59 g (3.43 mmol) of 2-(3,5-dibromophenyl)-4,6-diphenylpyrimidine, 2.02 g (7.20 mmol) of 2-[3-(4,4,5,5-tetramethyl-1,3,2-dioxabororan-2-yl)phenyl]pyridine, 2.34 g (7.20 mmol) of cesium carbonate, 31 mg (0.1372 mmol) of palladium acetate and 131 mg (0.274 mmol) of 2-dicyclohexylphosphino-2',4',6'-triisopropylbiphenyl were suspended in 60 mL of tetrahydrofuran, and the obtained suspension was heated under reflux for 55 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using a hexane/chloroform (1:1) mixed solvent as an eluent to give 1.69 g of the target 2-[3,3''-di(2-pyridyl)-1,1':3',1''-terphenyl-5'-yl]-4,6-diphenylpyrimidine as a white solid (yield: 80%).

$^1$H-NMR (CDCl$_3$): δ7.17-7.23 (m, 2H), 7.49-7.61 (m, 8H), 7.68-7.83 (m, 6H), 7.98 (t, J=0.9 Hz, 1H), 8.02 (s, 1H), 8.04 (t, J=1.8 Hz, 2H), 8.24-8.28 (m, 4H), 8.33 (t, J=1.8 Hz, 2H), 8.65-8.68 (m, 2H), 8.93 (d, J=1.8 Hz, 2H).

$^{13}$C-NMR (CDCl$_3$): δ111.0 (CH), 121.2 (CH×2), 122.7 (CH×2), 126.56 (CH×2), 126.59 (CH×2), 127.0 (CH×2), 127.8 (CH×4), 128.7 (CH×2), 129.1 (CH), 129.4 (CH×4), 129.7 (CH×2), 131.2 (CH×2), 137.2 (CH×2), 137.9 (quart.×2), 140.0 (quart.), 140.4 (quart.×2), 142.3 (quart.×2), 142.5 (quart.×2), 150.1 (CH×2), 157.8 (quart.×2), 164.9 (quart.), 165.3 (quart.×2).

Experiment Example 3

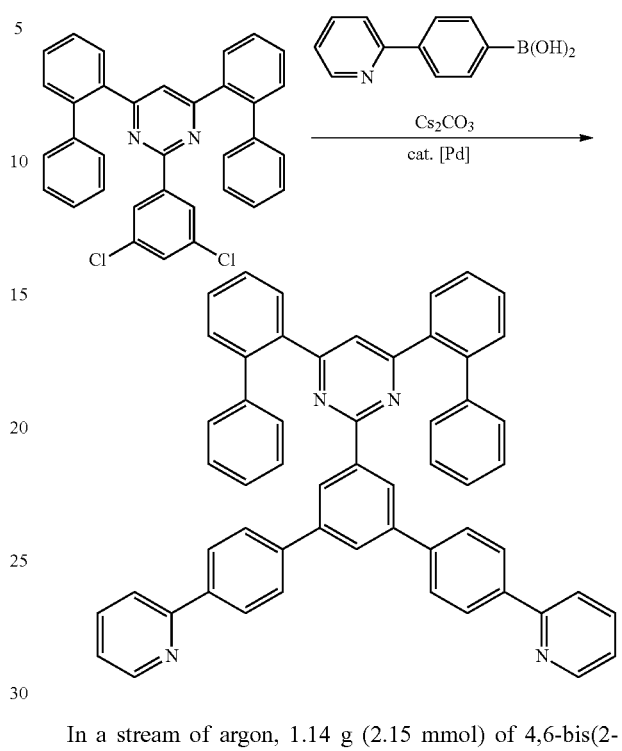

In a stream of argon, 1.14 g (2.15 mmol) of 4,6-bis(2-biphenylyl)-2-(3,5-dichlorophenyl)pyrimidine, 0.90 g (4.52 mmol) of 4-(2-pyridyl)phenylboronic acid, 1.47 g (4.52 mmol) of cesium carbonate, 19 mg (0.086 mmol) of palladium acetate and 82 mg (0.172 mmol) of 2-dicyclohexylphosphino-2',4',6'-triisopropylbiphenyl were suspended in 40 mL of tetrahydrofuran, and the obtained suspension was heated under reflux for 18 hours. The reaction mixture was cooled to room temperature, and was then distilled under a reduced pressure to remove all volatile materials. The thus-deposited solid was collected by filtration. The thus-obtained crude product was purified by silica gel chromatography using a hexane/chloroform (1:1) mixed solvent as an eluent to give 0.60 g of the target 4,6-bis(2-biphenylyl)-2-[4,4''-di(2-pyridyl)-1,1':3',1''-terphenyl-5'-yl]pyrimidine as a white solid (yield: 37%).

$^1$H-NMR (CDCl$_3$): δ7.04 (s, 1H), 7.22-7.36 (m, 10H), 7.45-7.59 (m, 8H), 7.80-7.89 (m, 8H), 7.96 (t, J=1.8 Hz, 1H), 8.18 (d, J=8.3 Hz, 4H), 8.25 (d, J=1.8 Hz, 2H), 8.78 (bd, J=4.8 Hz, 2H).

Experiment Example 4

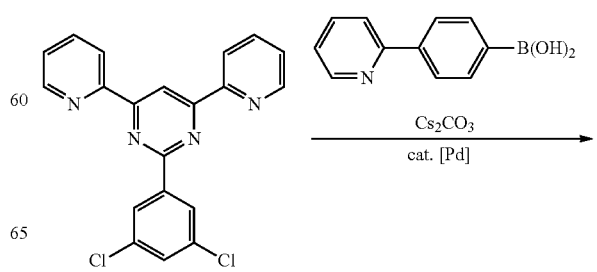

-continued

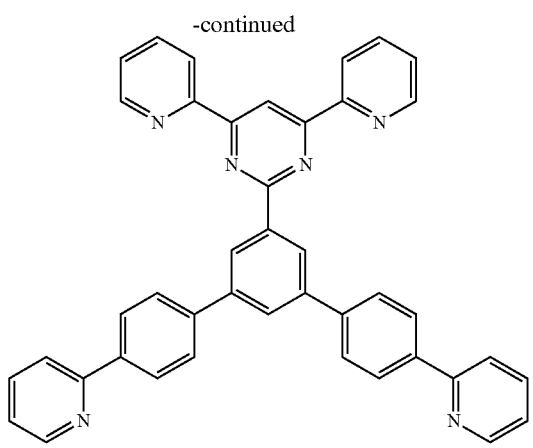

In a stream of argon, 0.50 g (1.32 mmol) of 2-(3,5-dichlorophenyl)-4,6-di(2-pyridyl)pyrimidine, 0.55 g (2.76 mmol) of 4-(2-pyridyl)phenylboronic acid, 0.90 g (2.77 mmol) of cesium carbonate, 24 mg (0.106 mmol) of palladium acetate and 101 mg (0.211 mmol) of 2-dicyclohexylphosphino-2',4', 6'-triisopropylbiphenyl were suspended in 30 mL of tetrahydrofuran, and the obtained suspension was heated under reflux for 17 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using chloroform as an eluent to give 0.46 g of the target 2-[4,4''-di(2-pyridyl)-1,1':3',1''-terphenyl-5'-yl]-4,6-di(2-pyridyl)pyrimidine as a white solid (yield: 56%).

$^1$H-NMR (CDCl$_3$): δ7.17-7.26 (m, 2H), 7.40 (ddd, J=7.5, 4.8, 1.0 Hz, 2H), 7.69-7.78 (m, 4H), 7.83-7.89 (m, 6H), 8.00 (t, J=1.6 Hz, 1H), 8.12 (d, J=8.3 Hz, 4H), 8.67-8.70 (m, 4H), 8.74 (d, J=4.0 Hz, 2H), 8.94 (d, J=1.8 Hz, 2H), 9.31 (s, 1H).

$^{13}$C-NMR (CDCl$_3$): δ112.0 (CH), 120.6 (CH×2, CH×2), 122.0 (CH×2), 122.3 (CH×2), 125.4 (CH×2), 126.5 (CH×4), 127.5 (CH×4), 127.9 (CH), 136.9 (CH×2), 137.1 (CH×2), 138.7 (quart.×2), 139.2 (quart.), 141.7 (quart.×2), 141.8 (quart.×2), 149.7 (CH×2), 149.8 (CH×2), 154.7 (quart.×2), 157.1 (quart.×2), 163.9 (quart.), 164.5 (quart.×2).

Experiment Example 5

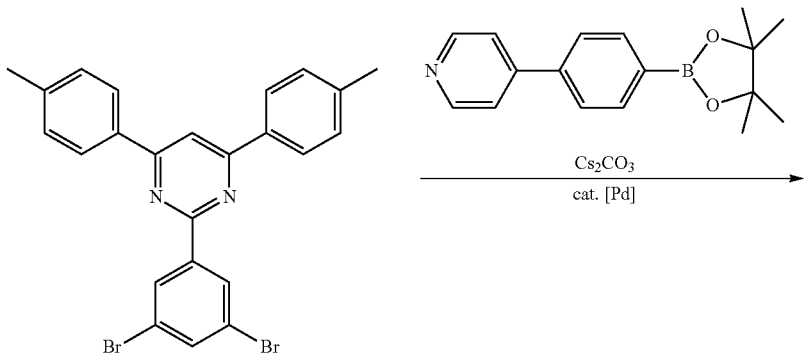

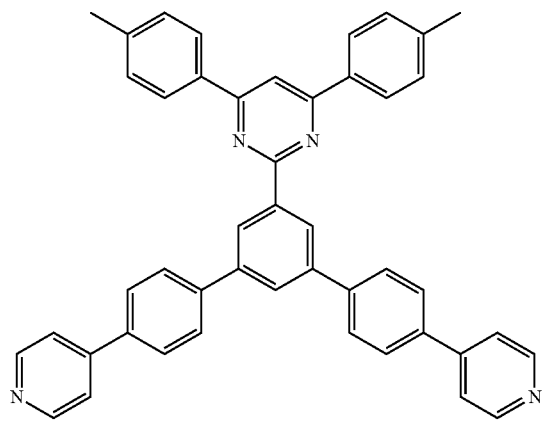

In a stream of argon, 0.40 g (0.81 mmol) of 2-(3,5-dibromophenyl)-4,6-di-p-tolylpyrimidine, 0.48 g (1.70 mmol) of 4-[4-(4,4,5,5-tetramethyl-1,3,2-dioxaboroan-2-yl)phenyl]-pyridine, 0.55 g (1.70 mmol) of cesium carbonate, 7 mg (0.032 mmol) of palladium acetate and 31 mg (0.065 mmol) of 2-dicyclohexylphosphino-2',4',6'-triisopropylbiphenyl were suspended in 20 mL of tetrahydrofuran, and the obtained suspension was heated under reflux for 87 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using a chloroform/methanol (100:1) mixed solvent as an eluent to give 0.30 g of the target 2-[4,4"-di(4-pyridyl)-1,1':3',1"-terphenyl-5'-yl]-4,6-di-p-tolylpyrimidine as a white solid (yield: 58%).

$^1$H-NMR (CDCl$_3$): δ2.50 (s, 6H), 7.41 (d, J=8.0 Hz, 4H), 7.63 (dd, J=4.5, 1.5 Hz, 4H), 7.84 (d, J=8.3 Hz, 4H), 7.95 (d, J=8.3 Hz, 4H), 8.03 (t, J=1.8 Hz, 1H), 8.05 (s, 1H), 8.24 (d, J=8.0 Hz, 4H), 8.73 (dd, J=4.5, 1.5 Hz, 4H), 9.02 (d, J=1.8 Hz, 2H).

$^{13}$C-NMR (CDCl$_3$): δ21.6 (CH3), 31.0 (CH3), 110.1 (CH), 121.5 (CH×4), 126.7 (CH×2), 127.3 (CH×4), 127.5 (CH×4), 128.2 (CH×4), 129.7 (CH×4), 134.7 (quart.×2), 137.3 (quart.×2), 139.9 (quart.), 141.2 (quart.×2), 141.3 (quart.×2), 142.0 (quart.×2), 147.9 (quart.×2), 150.4 (CH×4), 164.0 (quart.), 164.7 (quart.×2).

Experiment Example 6

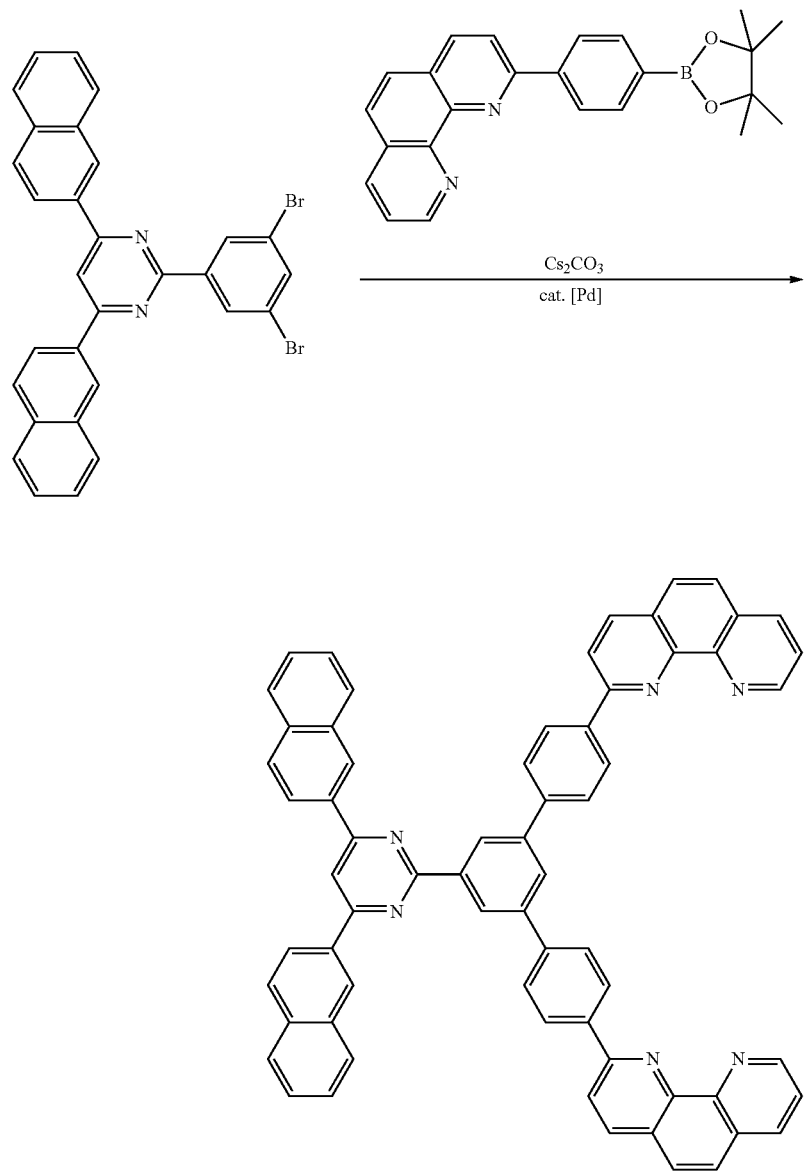

In a stream of argon, 0.50 g (0.88 mmol) of 2-(3,5-dibromophenyl)-4,6-di(2-naphthyl)pyrimidine, 0.95 g (2.82 mmol) of 2-[4-(4,4,5,5-tetramethyl-1,3,2-dioxabororan-2-yl)-phenyl]-1,10-phenanthroline, 0.63 g (1.94 mmol) of cesium carbonate, 8 mg (0.035 mmol) of palladium acetate and 34 mg (0.070 mmol) of 2-dicyclohexylphosphino-2',4',6'-triisopropylbiphenyl were suspended in 40 mL of toluene, and the obtained suspension was heated under reflux for 14 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using chloroform as an eluent to give 0.25 g of the target 2-[4,4''-bis(1,10-phenanthrorin-2-yl)-1,1':3',1''-terphenyl-5'-yl]-4,6-di(2-naphthyl)pyrimidine as a yellow solid (yield: 31%).

$^1$H-NMR (CDCl$_3$): δ7.52-7.55 (m, 4H), 7.61 (dd, J=4.4, 0.3 Hz, 2H), 7.73-7.82 (m, 4H), 7.88-7.92 (m, 2H), 8.00-8.09 (m, 8H), 8.13 (bs, 1H), 8.12-8.24 (m, 4H), 8.31 (d, J=8.5 Hz, 2H), 8.34 (s, 1H), 8.46 (d, J=8.3 Hz, 2H), 8.53 (d, J=8.0 Hz, 4H), 8.85 (bs, 2H), 9.10 (bs, 2H), 9.23 (d, J=4.3 Hz, 2H).

Experiment Example 7

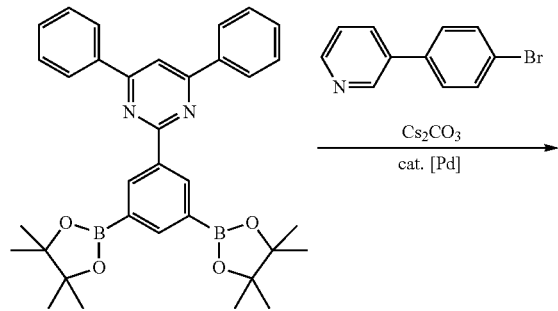

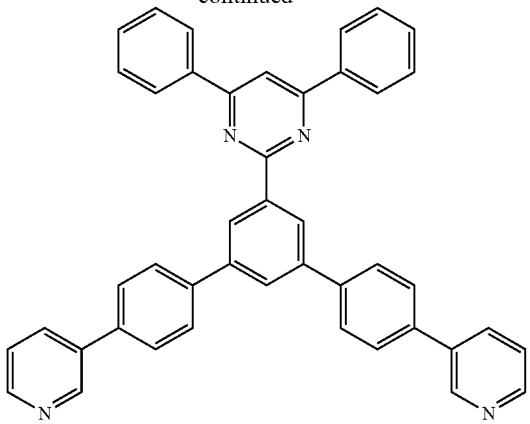

In a stream of argon, 0.18 g (0.32 mmol) of 2-[3,5-bis(4,4,5,5-tetarmethyl-1,3,2-dioxabororan-2-yl)phenyl]-4,6-diphenylpyrimidine, 0.19 g (0.82 mmol) of 3-(4-bromophenyl)-pyridine, 0.25 g (0.76 mmol) of cesium carbonate and 23 mg (0.033 mmol) of dichlorobis(triphenylphosphine)palladium were suspended in 10 mL of tetrahydrofuran, and the obtained suspension was heated under reflux for 12 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using a hexane/chloroform (1:1) mixed solvent as an eluent to give 77 mg of the target 2-[4,4''-di(3-pyridyl)-1,1':3',1''-terphenyl-5'-yl]-4,6-diphenylpyrimidine as a white solid (yield: 390).

$^1$H-NMR (CDCl$_3$): δ7.30-7.35 (m, 2H), 7.39-7.50 (m, 6H), 7.67 (d, J=7.8 Hz, 4H), 7.84 (d, J=7.8 Hz, 4H), 7.86-7.93 (m, 2H), 7.98 (s, 1H), 8.22-8.24 (m, 5H), 8.55 (d, J=4.3 Hz, 2H), 8.88 (bs, 2H), 8.91 (bs, 2H).

Experiment Example 8

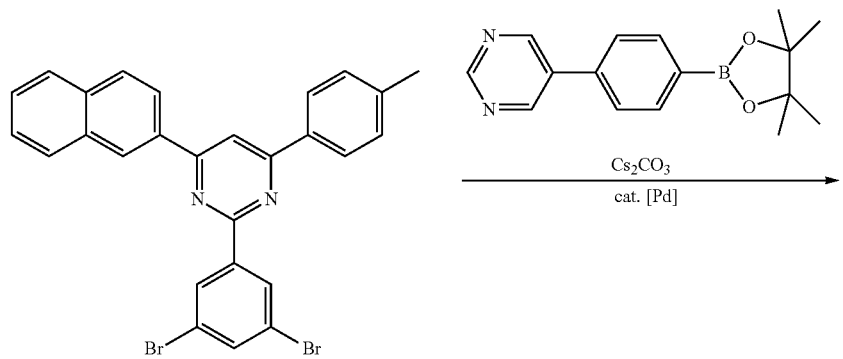

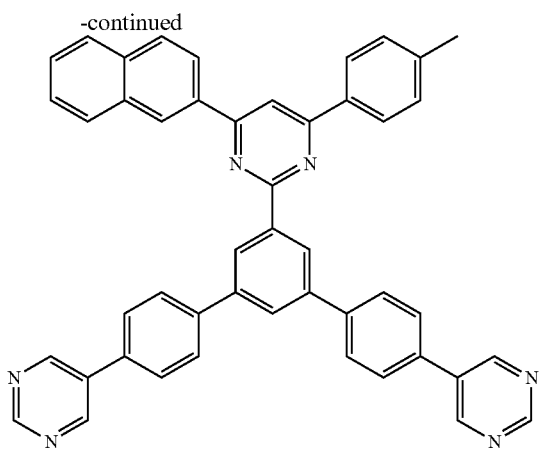

In a stream of argon, 0.40 g (0.75 mmol) of 2-(3,5-dibromophenyl)-4-(2-naphthyl)-6-p-tolylpyrimidine, 0.47 g (1.66 mmol) of 5-[4-(4,4,5,5-tetramethyl-1,3,2-dioxabororan-2-yl)phenyl]pyrimidine, 0.54 g (1.66 mmol) of cesium carbonate, 7 mg (0.030 mmol) of palladium acetate and 29 mg (0.060 mmol) of 2-dicyclohexylphosphino-2',4',6'-triisopropylbiphenyl were suspended in 15 ml of tetrahydrofuran, and the obtained suspension was heated under reflux for 15 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using a hexane/chloroform (1:1) mixed solvent as an eluent to give 0.28 mg of the target 2-[4,4''-di(5-pyrimidyl)-1,1':3',1''-terphenyl-5'-yl]-4-(2-naphthyl)-6-p-tolylpyrimidine as a yellowish white solid (yield: 54%).

$^1$H-NMR (CDCl$_3$): δ2.40 (s, 3H), 7.32 (d, J=8.0 Hz, 2H), 7.46-7.54 (m, 2H), 7.68 (d, J=8.3 Hz, 4H), 7.83-7.97 (m, 8H), 8.08 (s, 1H), 8.17 (d, J=8.0 Hz, 2H), 8.33 (dd, J=8.8, 0.1 Hz, 1H), 8.68 (bs, 1H), 8.94 (d, J=1.5 Hz, 2H), 8.98 (bs, 4H), 9.12 (bs, 2H).

$^{13}$C-NMR (CDCl$_3$): δ21.5 (CH3), 110.7 (CH), 124.3 (CH), 126.7 (CH), 126.8 (CH), 127.3 (CH×2, CH×2), 127.5 (CH× 4), 127.9 (CH), 128.0 (CH), 128.5 (CH×4), 128.8 (CH), 129.1 (CH), 129.8 (CH×2), 133.3 (quart.), 133.5 (quart.×2), 134.0 (quart.×2), 134.6 (quart.), 134.7 (quart.), 134.9 (quart.), 139.9 (quart.), 141.1 (quart.×2), 141.5 (quart.), 141.9 (quart.×2), 154.9 (CH×4) 157.7 (CH), 164.1 (quart.), 154.8 (quart.), 164.9 (quart.).

Experiment Example 9

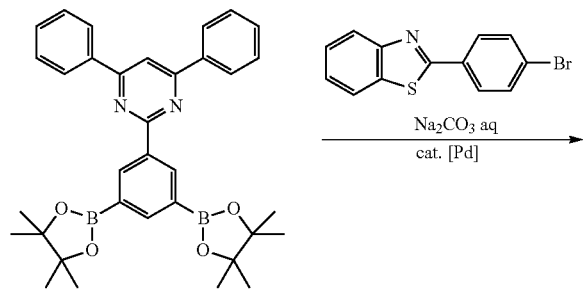

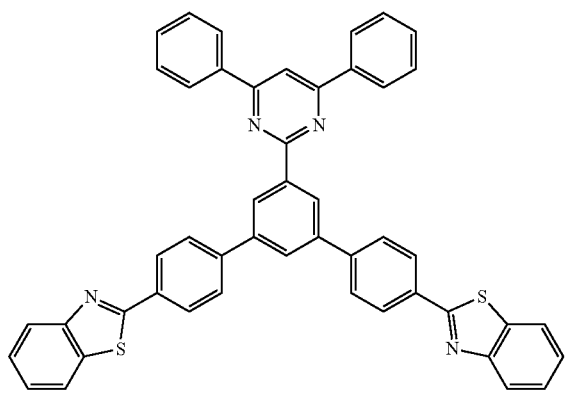

In a stream of argon, 0.15 g (0.26 mmol) of 2-[3,5-bis(4,4,5,5-tetramethyl-1,3,2-dioxabororan-2-yl)phenyl]-4,6-diphenylpyrimidine and 0.19 g (0.66 mmol) of 2-(4-bromophenyl)-1,3-benzothiazol, 77 mg (0.066 mmol) of tetrakis(triphenylphosphine)palladium were suspended in a mixture of 3 mL of an aqueous 2M sodium carbonate solution and 6 mL of toluene, and the obtained suspension was heated under reflux for 24 hours. The reaction mixture was cooled to room temperature, and was then distilled under a reduced pressure to remove all volatile materials. Methanol was added to the concentrate and the thus-deposited solid was collected by filtration. The thus-obtained crude product was purified by silica gel chromatography using a chloroform/methanol (100:1) mixed solvent as an eluent to give 0.12 g of the target 2-[4,4''-di(2-benzothiazolyl)-1,1':3',1''-terphenyl-5'-yl]-4,6-diphenylpyrimidine as a white solid (yield: 650).

¹H-NMR (CDCl₃): δ7.30-7.36 (m, 2H), 7.42-7.56 (m, 8H), 7.78-7.87 (m, 6H), 7.95-7.97 (m, 1H), 7.99 (s, 1H), 8.04 (d, J=7.8 Hz, 2H), 8.18 (d, J=8.3 Hz, 4H), 8.22-8.26 (m, 4H), 8.94 (d, J=1.8 Hz, 2H).

Experiment Example 10

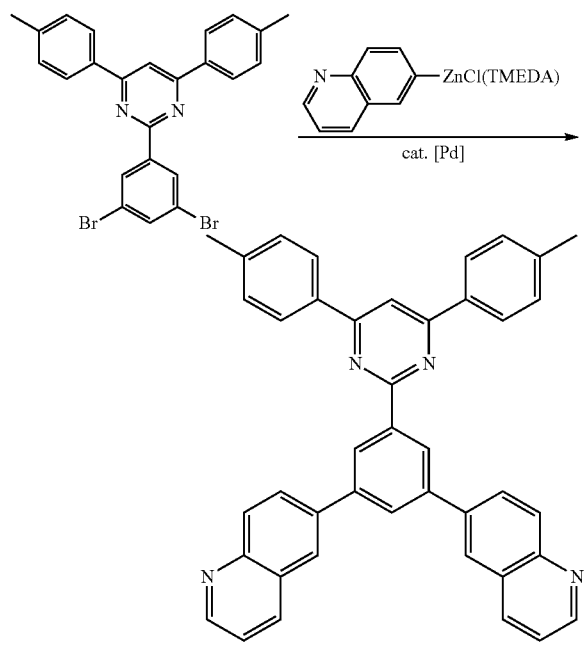

In a stream of argon, 0.34 g (1.62 mmol) of 6-bromoquinoline was dissolved in 7 mL of tetrahydrofuran, and then 1.03 mL of a solution of butyllithium 1.63 mmol in hexane was added dropwise at −78° C. The resultant mixture was stirred at −78° C. for 30 minutes, and then 0.41 g (1.63 mmol) of dichloro(tetramethylethylenediamine)zinc was added. The mixture was heated to room temperature and maintained at that temperature for 1 hour while being stirred. To the resultant mixture, 0.20 g (0.41 mmol) of 2-(3,5-dibromophenyl)-4,6-di-p-tolylpyrimidine, 19 mg (0.016 mmol) of tetrakis(triphenylphosphine)palladium and 3 mL of tetrahydrofuran were added, and the obtained suspension was heated under reflux for 17 hours. The reaction mixture was cooled to room temperature, and was then distilled under a reduced pressure to remove all volatile materials. The thus-deposited solid was collected by filtration. The thus-obtained crude product was purified by silica gel chromatography using a hexane/chloroform (1:1) mixed solvent as an eluent to give 0.16 g of the target 2-[3,5-di(6-quinolyl)phenyl-4,6-di-p-tolylpyrimidine as a white solid (yield: 65%).

¹H-NMR (CDCl₃): δ2.49 (s, 6H), 7.33-7.38 (m, 2H), 7.41 (d, J=8.0 Hz, 4H), 8.03 (t, J=1.8 Hz, 1H), 8.05 (s, 1H), 8.09-8.34 (m, 8H), 8.24 (d, J=8.0 Hz, 4H), 8.92 (dd, J=4.3, 1.5 Hz, 2H), 9.02 (d, J=1.8 Hz, 2H).

Experiment Example 11

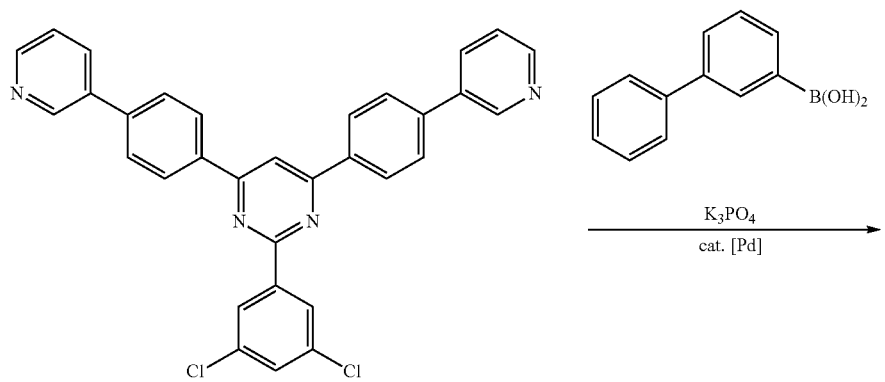

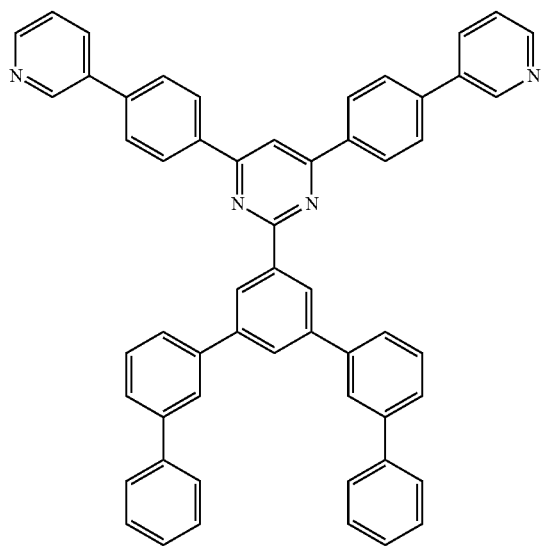

In a stream of argon, 0.45 g (0.85 mmol) of 2-(3,5-dichlorophenyl)-4,6-bis[4-(3-pyridyl)phenyl]pyrimidine, 0.37 g (1.87 mmol) of m-biphenylboronic acid, 0.39 g (1.86 mmol) of potassium phosphate, 8 mg (0.034 mmol) of palladium acetate and 32 mg (0.068 mmol) of 2-dicyclohexylphosphino-2',4',6'-triisipropylbiphenyl were suspended in 20 mL of tetrahydrofuran, and the obtained suspension was heated under reflux for 66 hours. The reaction mixture was cooled to room temperature, and was then distilled under a reduced pressure to remove all volatile materials. Methanol was added to the concentrate, and the thus-deposited solid was collected by filtration. The thus-obtained crude product was purified by silica gel chromatography using chloroform as an eluent to give 0.42 g of the target 4,6-bis[4-(3-pyridyl)phenyl]-2-(1,1': 3',1":3",1'":3"',1""-quinquephenyl-5"-yl)pyrimidine as a white solid (yield: 640).

$^1$H-NMR (CDCl$_3$): δ7.28-7.44 (m, 8H), 7.51-7.66 (m, 8H), 7.71-7.75 (m, 6H), 7.89 (t, J=1.9 Hz, 2H), 7.91-7.94 (m, 2H), 7.98 (t, J=1.6 Hz, 1H), 8.08 (s, 1H), 8.38 (d, J=8.3 Hz, 4H), 8.58 (dd, J=4.8, 1.5 Hz, 2H), 8.88 (d, J=2.3 Hz, 2H), 8.93 (d, J=1.8 Hz, 2H).

Experiment Example 12

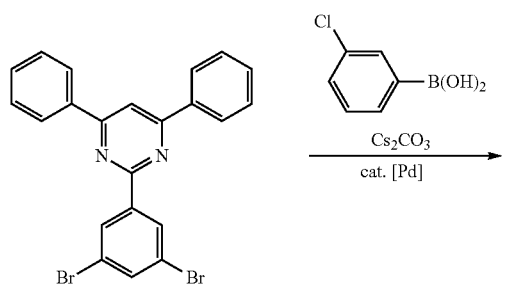

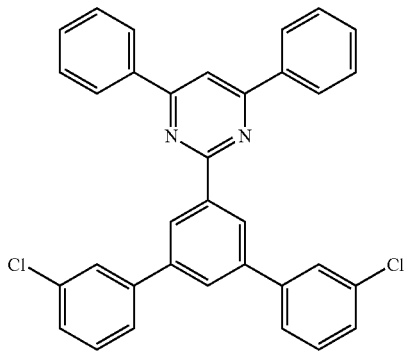

In a stream of argon, 5.00 g (10.7 mmol) of 2-(3,5-dibromophenyl)-4,6-diphenylpyrimidine, 3.70 g (23.6 mmol) of 3-chlorophenylboronic acid, 7.69 g (23.6 mmol) of cesium carbonate and 300 mg (0.43 mmol) of dichlorobis(triphenylphosphine)palladium were suspended in 100 mL of tetrahydrofuran, and the obtained suspension was heated under reflux for 15 hours. The reaction mixture was cooled to room temperature, and was then distilled under a reduced pressure to remove all volatile materials. The thus-deposited solid was collected by filtration. The thus-obtained crude product was purified by silica gel chromatography using a hexane/chloroform (1:1) mixed solvent as an eluent to give 3.58 g of the target 2-(3,3"-dichloro-(1,1':3',1"-terphenyl-5'-yl)-4,6-diphenylpyrimidine as a white solid (yield: 63%).

$^1$H-NMR (CDCl$_3$): δ7.32-7.43 (m, 4H), 7.51-7.55 (m, 6H), 7.60 (dt, J=7.3, 1.5 Hz, 2H), 7.69 (t, J=1.5 Hz, 2H), 7.79 (t, J=1.8 Hz, 1H), 8.01 (s, 1H), 8.22-8.26 (m, 4H), 8.84 (d, J=1.8 Hz, 2H).

Experiment Example 13

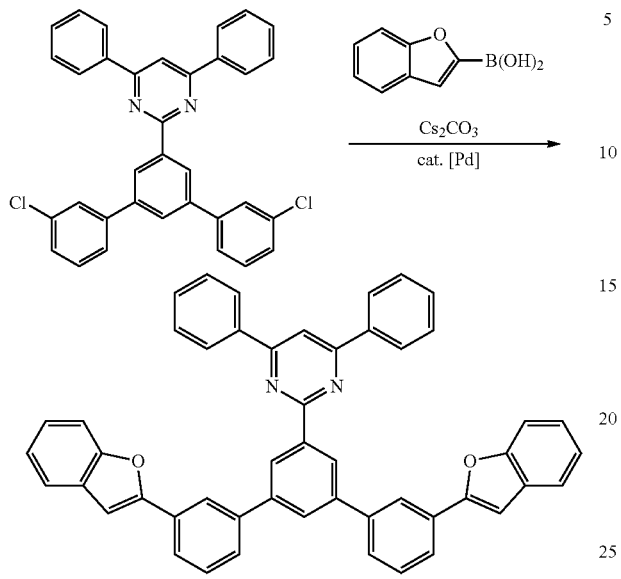

In a stream of argon, 0.50 g (0.94 mmol) of 2-(3,3''-dichloro-(1,1':3',1''-terphenyl-5'-yl)-4,6-diphenylpyrimidine, 0.67 g (4.16 mmol) of benzofurylboronic acid, 1.35 g (4.16 mmol) of cesium carbonate, 8 mg (0.038 mmol) of palladium acetate and 36 mg (0.075 mmol) of 2-dicyclohexylphosphino-2',4',6'-triisopropylbiphenyl were suspended in 20 mL of 1,4-dioxane, and the obtained suspension was heated under reflux for 14 hours. The reaction mixture was cooled to room temperature, and was then distilled under a reduced pressure to remove all volatile materials. Methanol was added to the concentrate, and the thus-deposited solid was collected by filtration. The thus-obtained crude product was purified by silica gel chromatography using a hexane/chloroform (1/1) mixed solvent as an eluent to give 0.16 g of the target 2-[3,3''-di(2-benzofuryl)-1,1':3',1''-terphenyl-5'-yl]-4,6-diphenylpyrimidine as a white solid (yield: 25%).

$^1$H-NMR (CDCl$_3$): δ7.09 (s, 2H), 7.15-7.27 (m, 4H), 7.48-7.59 (m, 12H), 7.74 (bd, J=7.7 Hz, 2H), 7.87 (bd, J=7.8 Hz, 2H), 8.01 (t, J=1.8 Hz, 1H), 8.03 (s, 1H), 8.23-8.30 (m, 6H), 8.96 (d, J=1.8 Hz, 2H).

$^{13}$C-NMR (CDCl$_3$): δ101.9 (CH×2), 110.8 (CH), 111.3 (CH×2), 121.0 (CH×2), 123.0 (CH×2), 124.1 (CH×2), 124.2 (CH×2), 124.5 (CH×2), 126.8 (CH×2), 127.4 (CH×4), 127.9 (CH×2), 128.6 (CH), 129.1 (CH×4), 129.3 (quart.×2), 129.4 (CH×2), 131.0 (CH×2), 131.2 (quart.×2), 137.5 (quart.×2), 139.6 (quart.), 141.9 (quart.×2), 142.0 (quart.×2), 155.1 (quart.×2), 155.9 (quart.×2), 164.4 (quart.), 165.0 (quart.×2).

Experiment Example 14

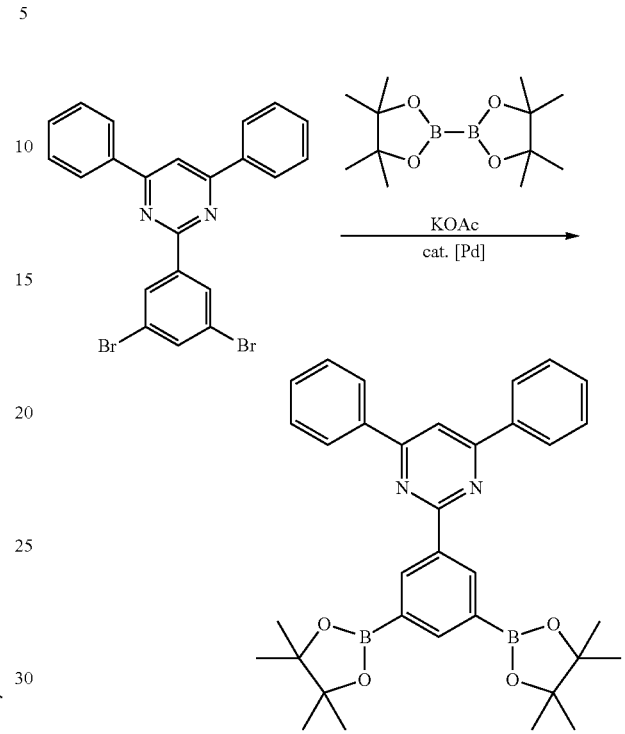

In a stream of argon, 1.00 g (2.15 mmol) of 2-(3,5-dibromophenyl)-4,6-diphenylpyrimidine, 1.20 g (4.73 mmol) of bispinacolatediborane, 0.70 g (7.09 mmol) of potassium acetate and 91 mg (0.129 mmol) of dichlorobis(triphenylphosphine)palladium were suspended in 20 mL of tetrahydrofuran, and the obtained suspension was heated under reflux for 77 hours. The reaction mixture was cooled to room temperature, and was then distilled under a reduced pressure to remove all volatile materials. The thus-deposited solid was collected by filtration. The obtained crude product was purified by silica gel chromatography using a hexane/chloroform (1:1) mixed solvent as an eluent to give 0.68 g of the target 2-[3,5-bis(4,4,5,5-tetramethyl-1,3,2-dioxabororan-2-yl)phenyl]-4,6-diphenylpyrimidine as a white solid (yield: 56%).

$^1$H-NMR (CDCl$_3$): δ1.32 (s, 24H), 7.49-7.52 (m, 6H), 7.94 (s, 1H), 8.23-8.27 (m, 4H), 8.34 (bs, 1H), 9.09 (d, J=1.3 Hz, 2H).

Experiment Example 15

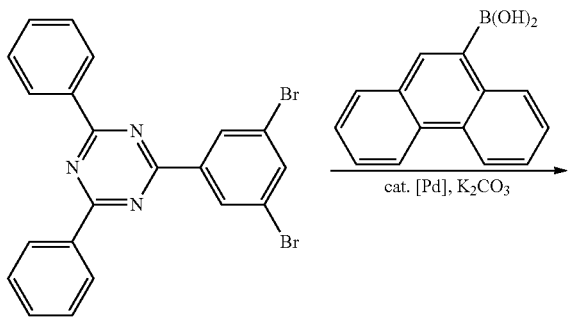

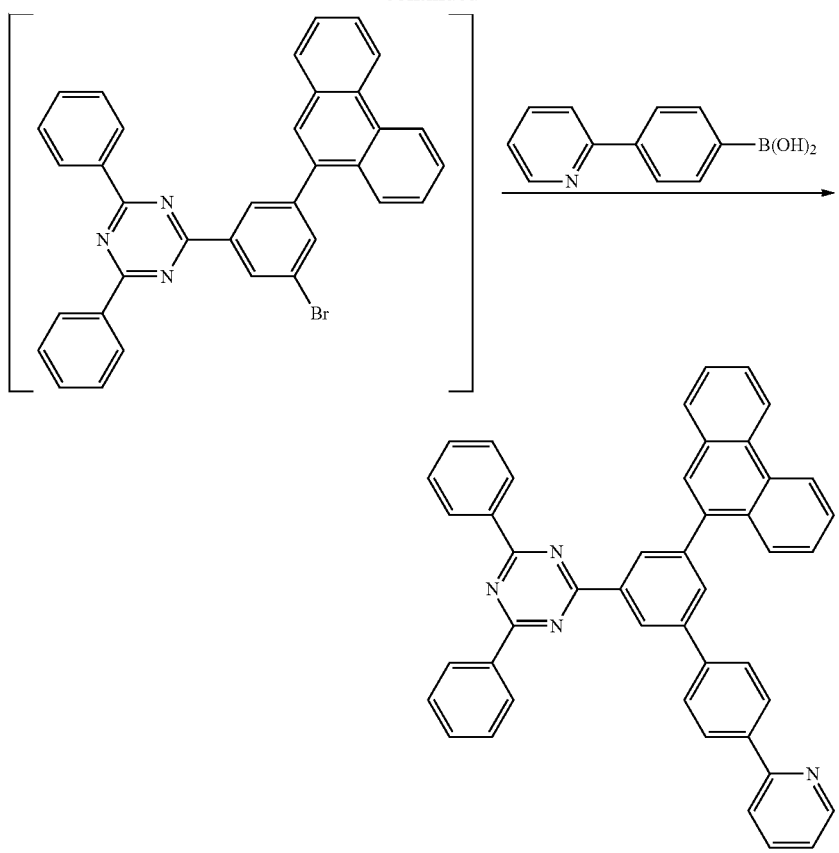

In a stream of argon, 1.91 g (8.56 mmol) of 9-phenanthreneboronic acid, 4.00 g (8.56 mmol) of 2-(3,5-dibromophenyl)-4,6-diphenyl-1,3,5-triazine and 98.9 mg (0.086 mmol) of tetrakis(triphenylphosphine)palladium were suspended in a mixed solvent composed of 320 mL of toluene and 40 mL of ethanol, and the resultant suspension was heated to 60° C. To the suspension, 25.7 mL (25.7 mmol) of an aqueous 1M $K_2CO_3$ solution was gradually added dropwise, and the mixture was stirred for 4 hours. Then the mixture was cooled to room temperature, and 2.56 g (12.8 mmol) of 4-(2-pyridyl)phenylboronic acid and 25.7 mL (25.7 mmol) of an aqueous 1M $K_2CO_3$ solution were added. Then the mixture was heated to 70° C. and maintained at that temperature for 12 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 3.91 g of the target 4,6-diphenyl-2-[5-(9-phenanthryl)-4'-(2-pyridyl)biphenyl-3-yl]-1,3,5-triazine as a white solid (yield: 64%).

$^1$H-NMR (CDCl$_3$): δ.7.31 (d, J=7.00 Hz, 1H), 7.58-7.65 (m, 8H), 7.70 (t, J=7.0 Hz, 1H), 7.76 (t, J=7.0 Hz, 2H), 7.82-7.87 (m, 2H), 7.93 (s, 1H), 7.99 (d, J=8.5 Hz, 2H), 8.02 (d, J=8.2 Hz, 1H), 8.06 (d, J=8.0 Hz, 1H), 8.12 (s, 1H), 8.23 (d, J=8.4 Hz, 2H), 8.78 (d, J=8.2 Hz, 1H), 8.82 (d, J=8.1 Hz, 4H), 8.89 (d, J=8.2 Hz, 1H), 8.98 (s, 1H), 9.21 (s, 1H).

The obtained triazine compound exhibited a Tg of 133° C.

Experiment Example 16

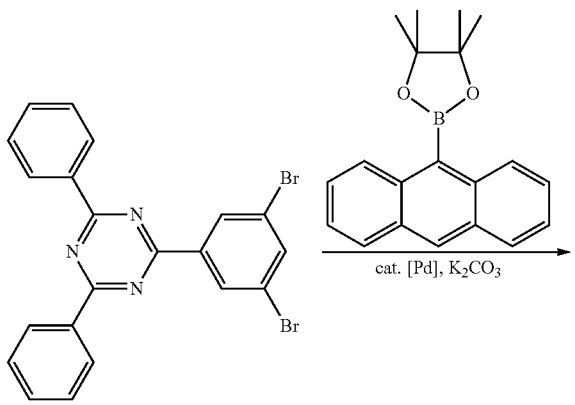

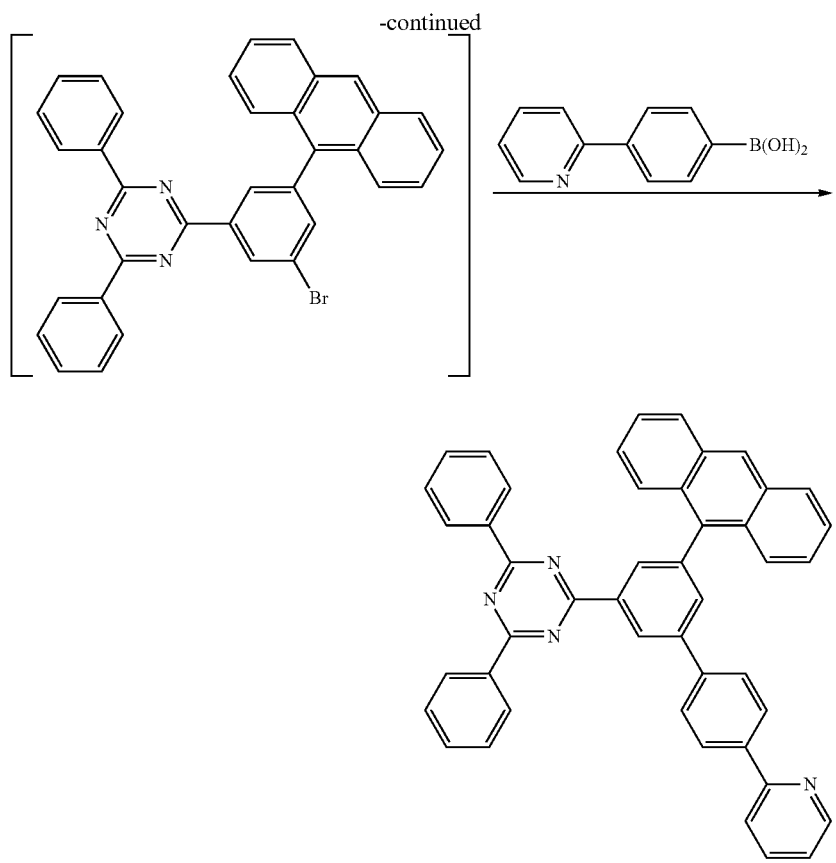

In a stream of argon, 0.98 g (3.21 mmol) of 9-(4,4,5,5-tetramethyl-1,3,2-dioxabororan-2-yl)anthracene, 1.50 g (3.21 mmol) of 2-(3,5-dibromophenyl)-4,6-diphenyl-1,3,5-triazine and 37.1 mg (0.032 mmol) of tetrakis(triphenylphosphine)palladium were suspended in a mixed solvent composed of 100 mL of toluene and 20 mL of ethanol, and the resultant suspension was heated to 60° C. To the suspension, 9.63 mL (9.63 mmol) of an aqueous 1M $K_2CO_3$ solution was gradually added dropwise, and the mixture was stirred for 3 hours. Then the mixture was cooled to room temperature, and 0.96 g (4.82 mmol) of 4-(2-pyridyl)phenylboronic acid and 6.42 mL (6.42 mmol) of an aqueous 1M $K_2CO_3$ solution were added. Then the mixture was heated to 60° C. and maintained at that temperature for 17 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.68 g of the target 2-[5-(9-anthryl)-4'-(2-pyridyl)biphenyl-3-yl]-4,6-diphenyl-1,3,5-triazine as a white solid (yield: 330).

$^1$H-NMR (CDCl$_3$): δ.7.34 (brs, 1H), 7.44 (t, J=7.6 Hz, 2H), 7.53-7.64 (m, 9H), 7.85-7.88 (m, 4H), 8.01 (d, J=7.6 Hz, 2H), 8.03 (s, 1H), 8.16 (d, J=8.5 Hz, 2H) 8.23 (d, J=8.3 Hz, 2H), 8.64 (s, 1H), 8.79 (d, J=5.6 Hz, 4H), 8.89 (s, 1H), 9.31 (s, 1H).

Experiment Example 17

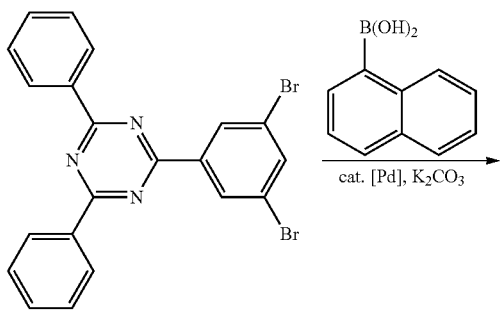

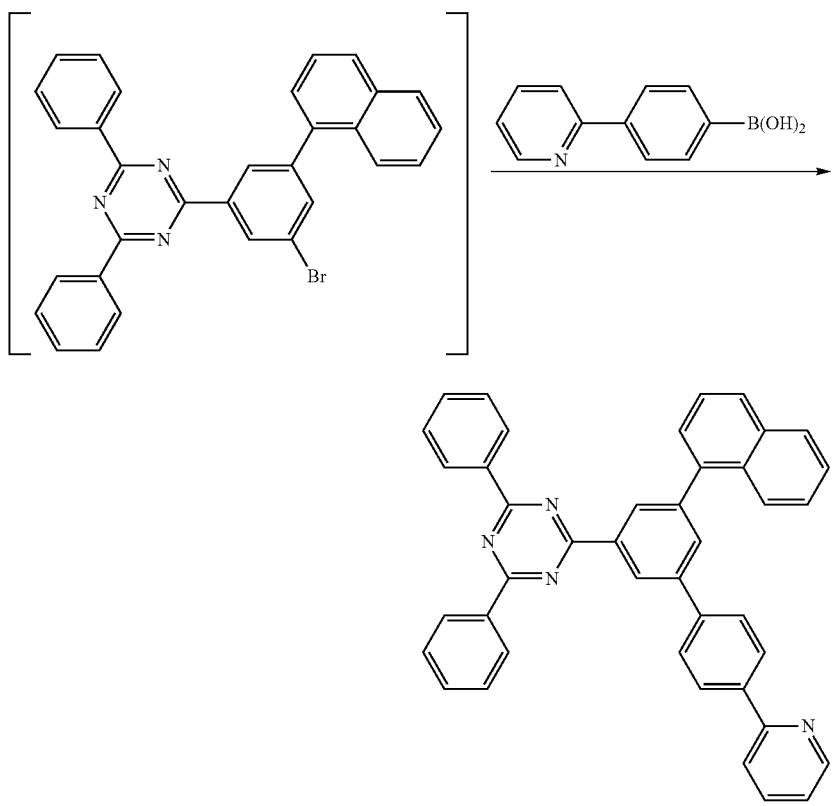

In a stream of argon, 0.37 g (2.14 mmol) of 1-naphthaleneboronic acid, 1.00 g (2.14 mmol) of 2-(3,5-dibromophenyl)-4,6-diphenyl-1,3,5-triazine and 24.7 mg (0.021 mmol) of tetrakis(triphenylphosphine)palladium were suspended in a mixed solvent composed of 80 mL of toluene and 10 mL of ethanol, and the resultant suspension was heated to 60° C. To the suspension, 8.56 mL (8.56 mmol) of an aqueous 1M $K_2CO_3$ solution was gradually added dropwise, and the mixture was stirred for 3 hours. Then the mixture was cooled to room temperature, and 0.64 g (3.21 mmol) of 4-(2-pyridyl)phenylboronic acid wad added. Then the mixture was heated to 70° C. and maintained at that temperature for 3 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.61 g of the target 4,6-diphenyl-2-[5-(1-naphthyl)-4'-(2-pyridyl)biphenyl-3-yl]-1,3,5-triazine as a white solid (yield: 49%).

$^1$H-NMR ($CDCl_3$): δ.7.32 (t, J=6.5 Hz, 1H), 7.53 (t, J=6.9 Hz, 1H), 7.57-7.68 (m, 10H), 7.83-7.87 (m, 2H), 7.98 (d, J=8.4 Hz, 2H), 8.00-8.05 (m, 2H), 8.07 (s, 1H), 8.23 (d, J=6.7 Hz, 2H), 7.79 (d, J=6.5 Hz, 1H), 8.82 (d, J=8.5 Hz, 4H), 8.93 (s, 1H), 9.18 (s, 1H).

The obtained triazine compound exhibited a Tg of 107° C.

Experiment Example 18

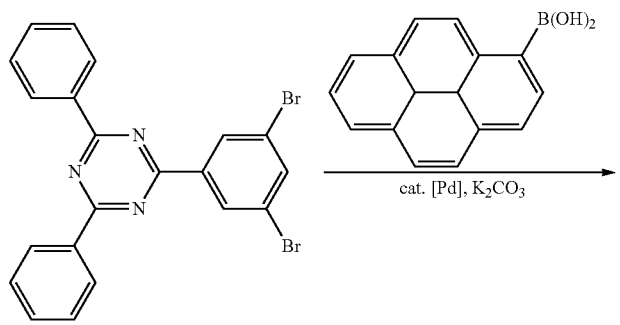

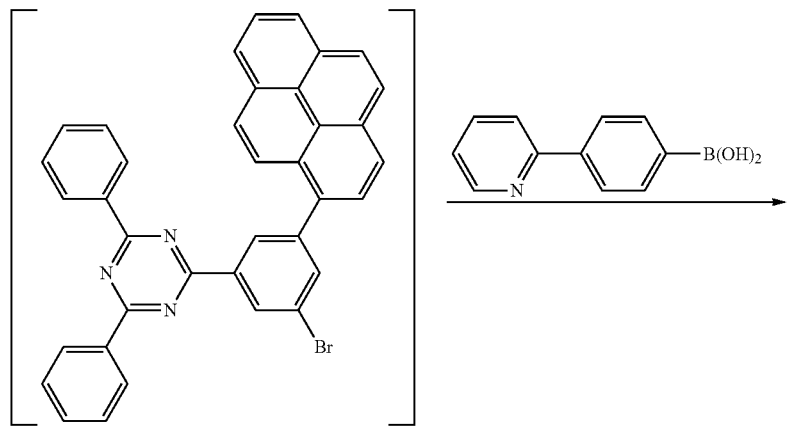

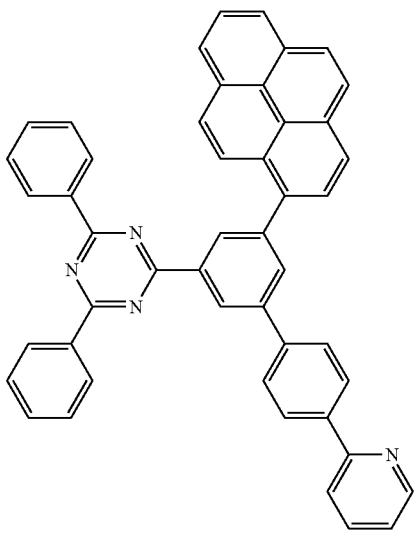

In a stream of argon, 0.53 g (2.14 mmol) of 1-pyreneboronic acid, 1.00 g (2.14 mmol) of 2-(3,5-dibromophenyl)-4,6-diphenyl-1,3,5-triazine and 24.7 mg (0.0214 mmol) of tetrakis(triphenylphosphine)palladium were suspended in a mixed solvent composed of 80 mL of toluene and 10 mL of ethanol, and the resultant suspension was heated to 60° C. To the suspension, 8.56 mL (8.56 mmol) of an aqueous 1M $K_2CO_3$ solution was gradually added dropwise, and the mixture was stirred for 3 hours. Then the mixture was cooled to room temperature, and 0.64 g (3.21 mmol) of 4-(2-pyridyl)phenylboronic acid wad added. Then the mixture was heated to 70° C. and maintained at that temperature for 3 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.37 g of the target 4,6-diphenyl-2-[5-(1-pyrenyl)-4'-(2-pyridyl)biphenyl-3-yl]-1,3,5-triazine as a white solid (yield: 26%).

$^1$H-NMR ($CDCl_3$): δ.7.35 (brs, 1H), 7.57-7.65 (m, 6H), 7.86-7.91 (m, 2H), 8.03 (d, J=8.4 Hz, 2H), 8.08 (t, J=7.6 Hz, 1H), 8.13 (d, J=9.3 Hz, 1H), 8.18-8.29 (m, 8H), 8.33 (d, J=9.3 Hz, 1H), 8.37 (d, J=7.8 Hz, 1H), 8.80 (d, J=4.8 Hz, 1H), 8.83 (d, J=7.9 Hz, 4H), 9.07 (s, 1H), 9.23 (s, 1H).

Experiment Example 19

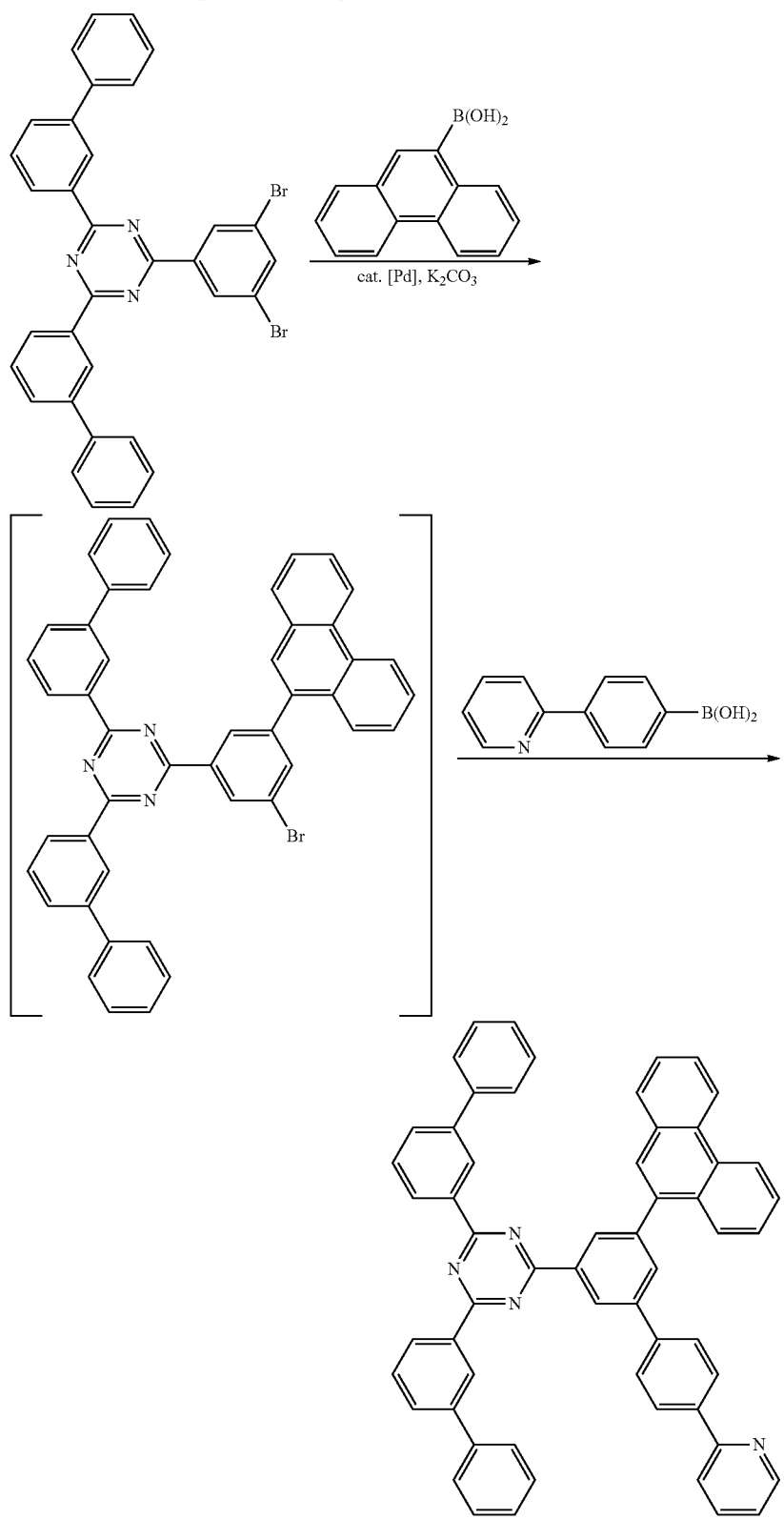

In a stream of argon, 0.54 g (2.42 mmol) of 9-phenanthreneboronic acid, 1.50 g (2.42 mmol) of 4,6-bis(biphenyl-3-yl)-2-(3,5-dibromophenyl)-1,3,5-triazine and 56.0 mg (0.048 mmol) of tetrakis(triphenylphosphine)palladium were suspended in a mixed solvent composed of 150 mL of toluene and 20 mL of ethanol, and the resultant suspension was heated to 60° C. To the suspension, 7.26 mL (7.26 mmol) of an aqueous 1M K$_2$CO$_3$ solution was gradually added dropwise, and the mixture was stirred for 3 hours. Then the mixture was cooled to room temperature, and 0.72 g (3.63 mmol) of 4-(2-pyridyl)phenylboronic acid and 7.26 mL (7.26 mmol) of an aqueous 1M K$_2$CO$_3$ solution were added. Then the mixture was heated to 60° C. and maintained at that temperature for 4 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 1.1 g of the target 4,6-bis(biphenyl-3-yl)-2-[5-(9-phenathryl)-4'-(2-pyridyl)biphenyl-3-yl]-1,3,5-triazine as a white solid (yield: 58%).

$^1$H-NMR (CDCl$_3$): δ.7.34 (brs, 1H), 7.43 (t, J=7.4 Hz, 2H), 7.52 (t, J=7.4 Hz, 4H), 7.66 (t, J=8.1 Hz, 1H), 7.68 (t, J=7.7 Hz, 2H), 7.70 (t, J=7.7 Hz, 1H), 7.74-7.78 (m, 2H), 7.76 (d, J=8.4 Hz, 4H), 7.87 (d, J=7.6 Hz, 4H), 7.94 (s, 1H), 8.00 (d, J=8.4 Hz, 2H), 8.01 (d, J=7.7 Hz, 1H), 8.12 (t, J=7.4 Hz, 1H), 8.14 (s, 1H), 8.23 (d, J=8.3 Hz, 2H), 8.80 (d, J=7.8 Hz, 1H), 8.80 (d, J=7.8 Hz, 2H), 8.82 (d, J=8.3 Hz, 1H), 8.88 (d, J=8.3 Hz, 1H), 9.01 (s, 1H), 9.05 (s, 2H), 9.21 (s, 1H).

The obtained triazine compound exhibited a Tg of 119° C.

Experiment Example 20

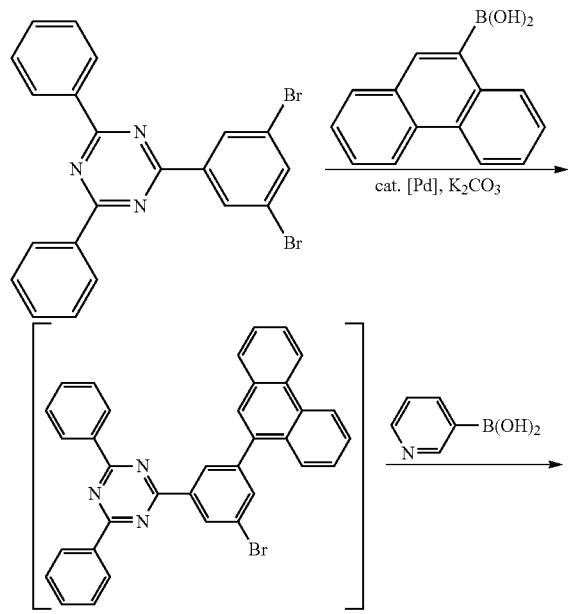

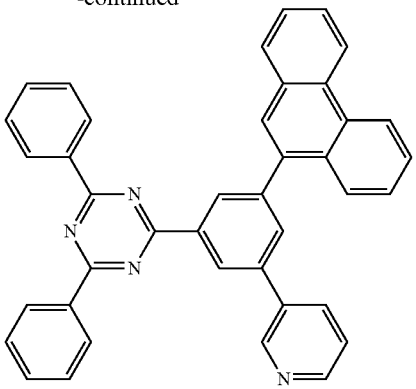

In a stream of argon, 0.71 g (3.21 mmol) of 9-phenanthreneboronic acid, 1.50 g (3.21 mmol) of 2-(3,5-dibromophenyl)-4,6-diphenyl-1,3,5-triazine and 37.0 mg (0.0321 mmol) of tetrakis(triphenylphosphine)palladium were suspended in a mixed solvent composed of 120 mL of toluene and 15 mL of ethanol, and the resultant suspension was heated to 60° C. To the suspension, 9.63 mL (9.63 mmol) of an aqueous 1M K$_2$CO$_3$ solution was gradually added dropwise, and the mixture was stirred for 6 hours. Then the mixture was cooled to room temperature, and 0.59 g (4.82 mmol) of 3-pyridineboronic acid and 9.63 mL (9.63 mmol) of an aqueous 1M K$_2$CO$_3$ solution were added. Then the mixture was heated to 60° C. and maintained at that temperature for 18 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.87 g of the target 4,6-diphenyl-2-[5-(9-phenanthryl)-3-(3-pyridyl)phenyl]-1,3,5-triazine as a white solid (yield: 48%).

$^1$H-NMR (CDCl$_3$): δ.7.59-7.67 (m, 8H), 7.72 (t, J=7.0 Hz, 1H), 7.76-7.80 (m, 2H), 7.90 (s, 1H), 7.90 (brt, J=6.5 Hz, 1H), 7.96 (d, J=8.1 Hz, 1H), 8.02 (d, J=7.1 Hz, 1H), 8.05 (s, 1H), 8.60 (d, J=8.0 Hz, 1H), 8.80 (d, J=7.0 Hz, 4H), 8.83 (d, J=8.4 Hz, 1H), 8.89 (d, J=8.3 Hz, 1H), 9.13 (d, J=5.4 Hz, 1H), 9.14 (s, 1H), 9.22 (s, 1H).

Experiment Example 21

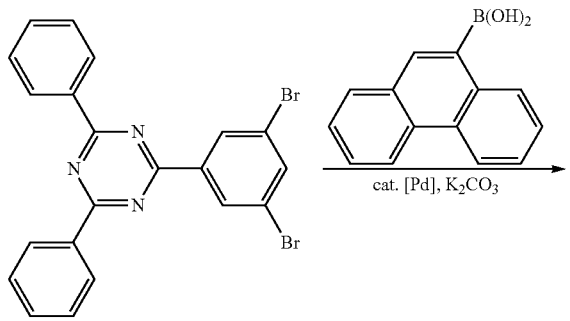

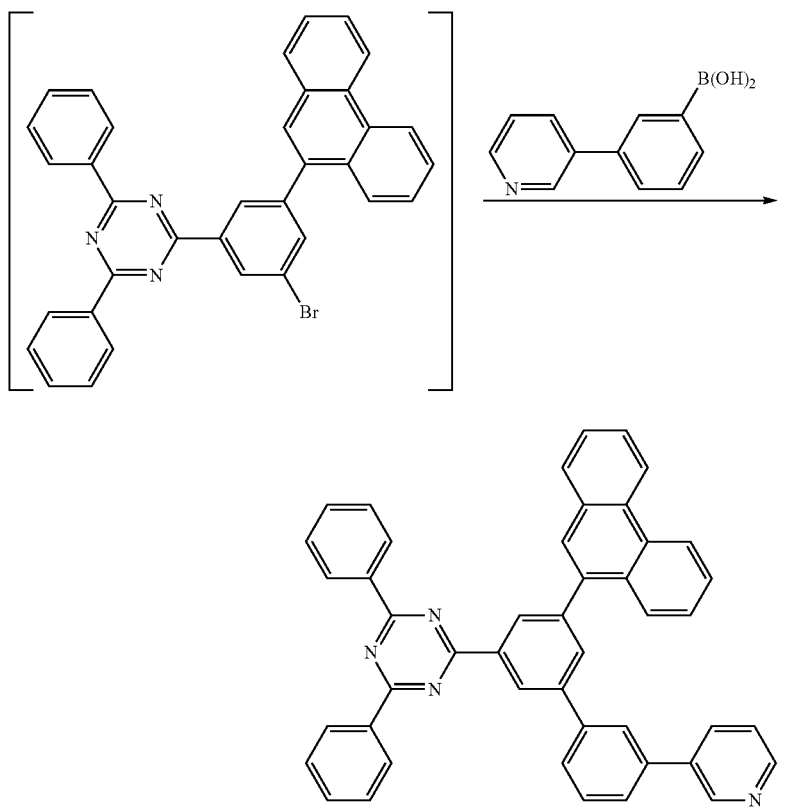

In a stream of argon, 0.71 g (3.21 mmol) of 9-phenanthreneboronic acid, 1.50 g (3.21 mmol) of 2-(3,5-dibromophenyl)-4,6-diphenyl-1,3,5-triazine and 37.0 mg (0.0321 mmol) of tetrakis(triphenylphosphine)palladium were suspended in a mixed solvent composed of 120 mL of toluene and 15 mL of ethanol, and the resultant suspension was heated to 60° C. To the suspension, 9.63 mL (9.63 mmol) of an aqueous 1M $K_2CO_3$ solution was gradually added dropwise, and the mixture was stirred for 8 hours. Then the mixture was cooled to room temperature, and 0.59 g (4.82 mmol) of 3-(3-pyridyl)phenylboronic acid and 9.63 mL (9.63 mmol) of an aqueous 1M $K_2CO_3$ solution were added. Then the mixture was heated to 60° C. and maintained at that temperature for 18 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.86 g of the target 4,6-diphenyl-2-[5-(9-phenanthryl)-3'-(3-pyridyl)biphenyl-3-yl]-1,3,5-triazine as a white solid (yield: 42%).

$^1$H-NMR (CDCl$_3$): δ.7.57-7.66 (m, 7H), 7.69-7.72 (m, 2H), 7.44-7.81 (m, 3H), 7.81 (dd, J=8.0, 5.4 Hz, 1H), 7.92 (s, 1H), 8.02 (t, J=7.80 Hz, 4H), 8.07 (s, 1H), 8.46 (d, J=8.1 Hz, 1H), 8.72 (d, J=5.3 Hz, 1H), 8.81 (d, J=7.0 Hz, 4H), 8.82 (d, J=8.2 Hz, 1H), 8.88 (d, J=8.2 Hz, 1H), 9.02 (s, 1H), 9.06 (s, 1H), 9.14 (s, 1H).

The obtained triazine derivative exhibited a Tg of 112° C.

Experiment Example 22

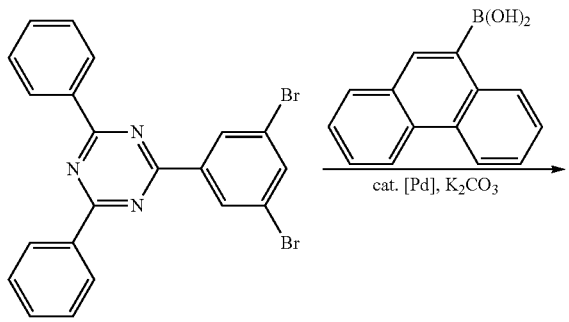

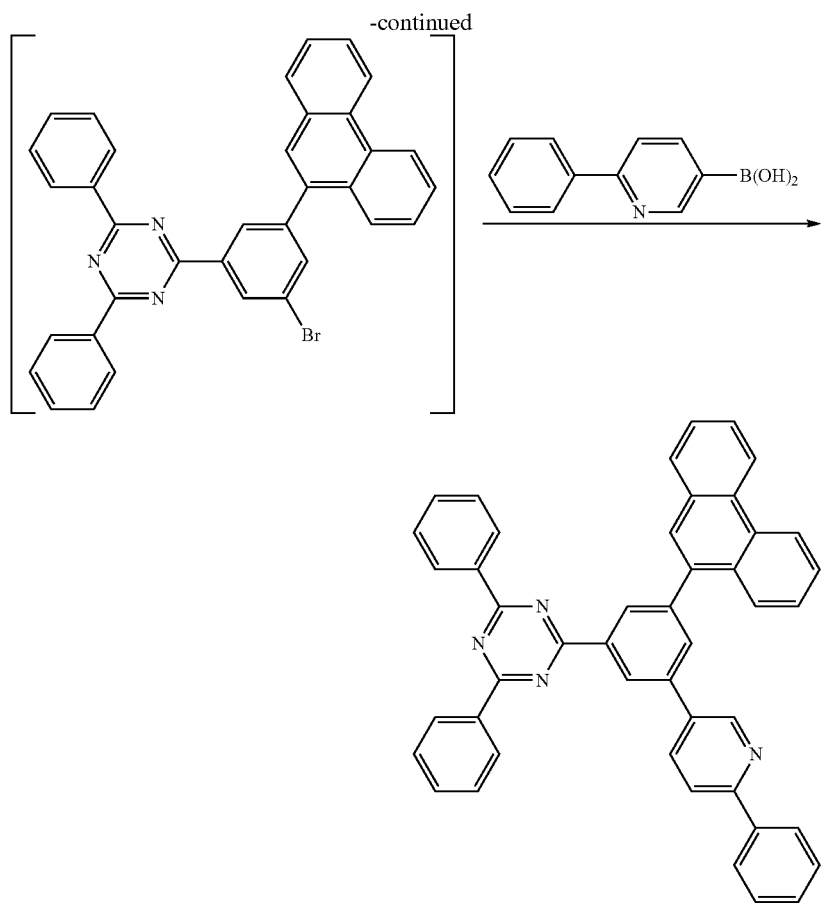

In a stream of argon, 0.43 g (1.93 mmol) of 9-phenanthreneboronic acid, 0.90 g (1.93 mmol) of 2-(3,5-dibromophenyl)-4,6-diphenyl-1,3,5-triazine and 22.3 mg (0.0193 mmol) of tetrakis-(triphenylphosphine)palladium were suspended in a mixed solvent composed of 75 mL of toluene and 10 mL of ethanol, and the resultant suspension was heated to 60° C. To the suspension, 5.78 mL (5.78 mmol) of an aqueous 1M $K_2CO_3$ solution was gradually added dropwise, and the mixture was stirred for 7 hours. Then the mixture was cooled to room temperature, and 0.57 g (2.89 mmol) of 3-(6-phenyl) pyridineboronic acid and 5.78 mL (5.78 mmol) of an aqueous 1M $K_2CO_3$ solution were added. Then the mixture was heated to 70° C. and maintained at that temperature for 14 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.73 g of the target 4,6-diphenyl-2-[5-(9-phenanthryl)-1-(6-phenylpyridin-3-yl) phenyl-3-yl]-1,3,5-triazine as a white solid (yield: 59%).

$^1$H-NMR (CDCl$_3$): δ.7.50 (t, J=6.8 Hz, 1H), 7.55-7.66 (m, 9H), 7.71 (t, J=6.8 Hz, 1H), 7.77 (t, J=7.0 Hz, 2H), 7.93 (s, 1H), 7.95 (d, J=8.2 Hz, 1H), 8.02 (d, J=7.8 Hz, 1H), 8.05 (d, J=8.3 Hz, 1H), 8.10 (s, 1H), 8.14 (d, J=7.2 Hz, 2H), 8.24 (d, J=7.0 Hz, 1H), 8.82 (d, J=6.9 Hz, 4H), 8.85 (d, J=8.2 Hz, 1H), 8.89 (d, J=8.2 Hz, 1H), 9.03 (s, 1H), 9.22 (s, 1H), 9.26 (s, 1H).

The obtained triazine derivative exhibited a Tg of 127° C.

Experiment Example 23

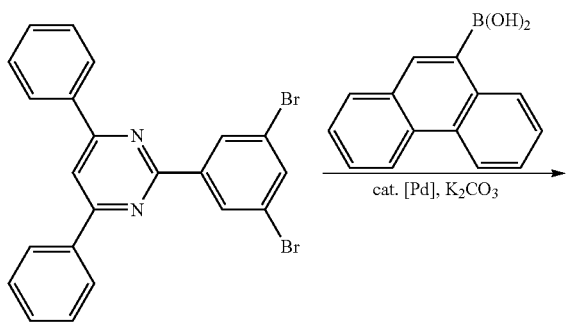

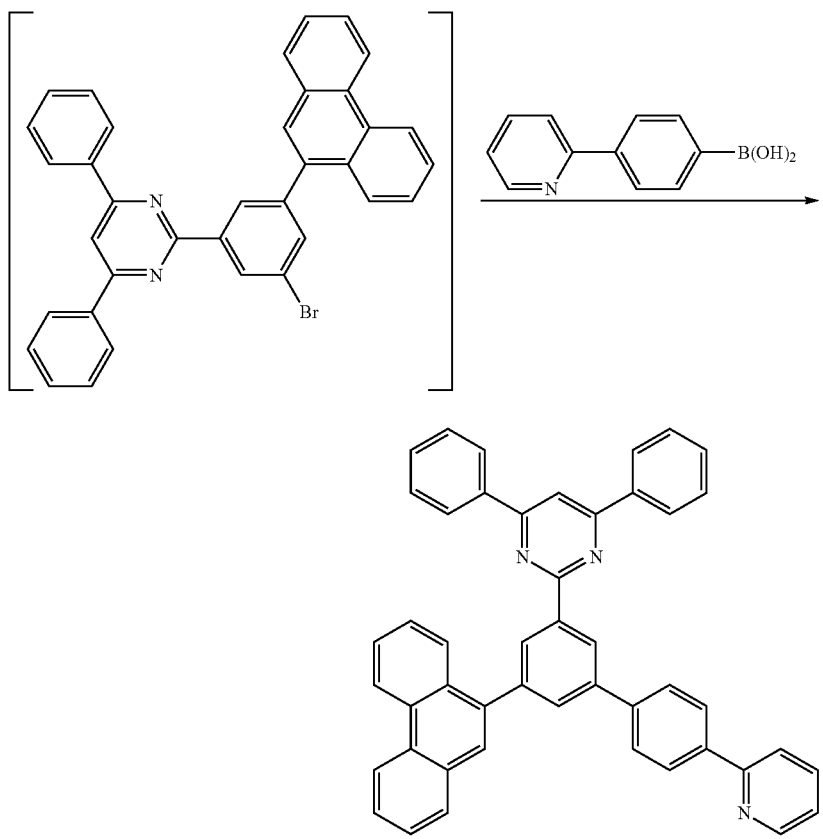

In a stream of argon, 0.714 g (3.22 mmol) of 9-phenanthreneboronic acid, 1.50 g (3.22 mmol) of 2-(3,5-dibromophenyl)-4,6-diphenylpyrimidine and 37.2 mg (0.0322 mmol) of tetrakis(triphenylphosphine)palladium were suspended in a mixed solvent composed of 120 mL of toluene and 15 mL of ethanol, and the resultant suspension was heated to 50° C. To the suspension, 9.66 mL (9.66 mmol) of an aqueous 1M $K_2CO_3$ solution was gradually added dropwise, and the mixture was stirred for 18 hours. Then the mixture was cooled to room temperature, and 0.961 g (4.83 mmol) of 4-(2-pyridyl)phenylboronic acid and 9.66 mL (9.66 mmol) of an aqueous 1M $K_2CO_3$ solution were added. Then the mixture was heated to 60° C. and maintained at that temperature for 4 hours while being stirred. Then the reaction mixture was cooled to room temperature, and was then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 1.28 g of the target 4,6-diphenyl-2-[5-(9-phenanthryl)-4'-(2-pyridyl)biphenyl-3-yl]-pyrimidine as a white solid (yield: 62%).

$^1$H-NMR (CDCl$_3$): δ. 7.25 (t, J=4.9 Hz, 1H), 7.53-7.58 (m, 6H), 7.60 (d, J=7.5 Hz, 1H), 7.66 (t, J=7.0 Hz, 1H), 7.12 (t, J=8.2 Hz, 2H), 7.62-7.83 (m, 2H), 7.90 (s, 1H), 7.95-8.00 (m, 4H), 8.07 (d, J=8.1 Hz, 1H), 8.09 (s, 1H), 8.17 (d, J=8.5 Hz, 1H), 8.30-8.32 (m, 4H), 8.73 (d, J=5.0 Hz, 1H), 8.79 (d, J=8.3 Hz, 1H), 8.84 (d, J=8.2 Hz, 1H), 8.90 (s, 1H), 9.14 (s, 1H).

Experiment Example 24

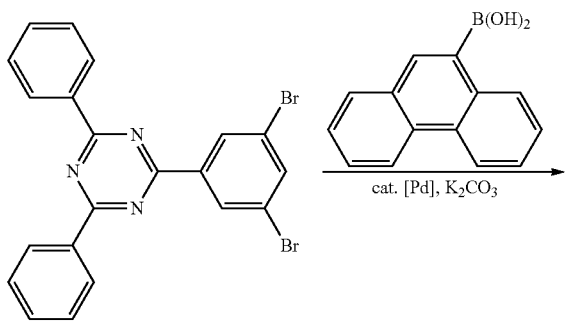

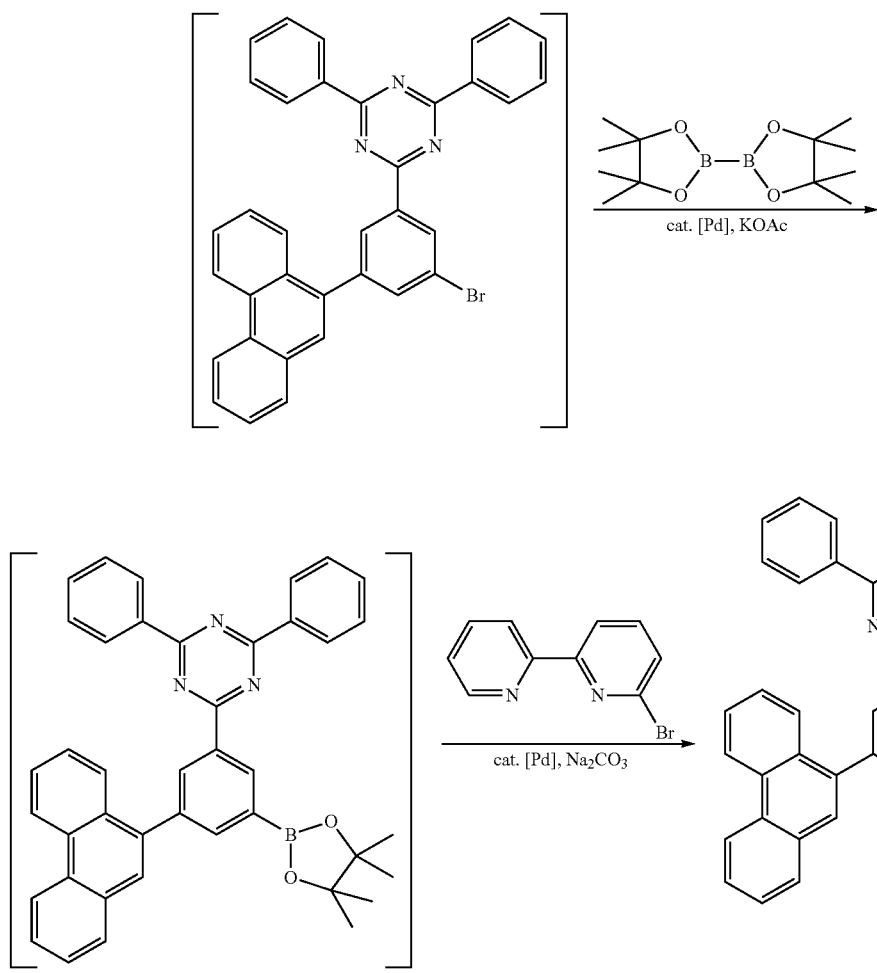

In a stream of argon, 8.00 g (17.1 mmol) of 2-(3,5-dibromophenyl)-4,6-diphenyl-1,3,5-triazine, 3.80 g (17.1 mmol) of 9-phenanthreneboronic acid and 198 mg (0.171 mmol) of tetrakis(triphenylphosphine)palladium were suspended in a mixed solvent composed of 600 mL of toluene and 80 mL of ethanol, and the resultant suspension was heated to 50° C. To the suspension, 51.4 mL (51.4 mmol) of an aqueous 1M $K_2CO_3$ solution was gradually added dropwise, and the mixture was stirred for 15 hours. Then the resultant reaction mixture was cooled to room temperature, and was then distilled under a reduced pressure to remove all volatile materials. The obtained concentrate was purified to remove inorganic ingredients by silica gel chromatography using a hexane/chloroform (1/1) mixed solvent as an eluent to give 9.59 g of a mixture containing 4,6-diphenyl-2-[5-(9-phenanthryl)-3-bromophenyl]-1,3,5-triazine.

In a stream of argon, 2.00 g of the obtained mixture containing 4,6-diphenyl-2-[5-(9-phenanthryl)-3-bromophenyl]-1,3,5-triazine, 1.35 g (5.31 mmol) of bispinacolatediboron, 1.04 g (10.6 mmol) of potassium acetate and 128 mg (0.142 mmol) of dichlorobistriphenylphosphinepalladium were suspended in 70 mL of tetrahydrofuran, and the resultant suspension was stirred at 70° C. for 5 hours. Then the resultant reaction mixture was cooled to room temperature, and was then distilled under a reduced pressure to remove all volatile materials. The obtained concentrate was purified to remove inorganic ingredients by silica gel chromatography using a hexane/chloroform (1:1) mixed solvent as an eluent to give 1.50 g of a mixture containing 4,6-diphenyl-2-[5-(9-phenanthryl)-3-(4,4,5,5-tetramethyl-1,3,2-dioxabororan-2-yl)phenyl]-1,3,5-triazine.

In a stream of argon, 0.50 g of the obtained mixture containing 4,6-diphenyl-2-[5-(9-phenanthryl)-3-(4,4,5,5-tetramethyl-1,3,2-dioxabororan-2-yl)phenyl]-1,3,5-triazine, 288 mg (1.22 mmol) of 6-bromo-2,2'-bipiridine and 47.3 mg (0.0409 mmol) of tetrakis(triphenylphosphine)palladium were suspended in 25 mL of toluene. To the suspension, 10 mL (20 mmol) of an aqueous 2M $Na_2CO_3$ solution was added, and the obtained mixture was stirred at 90° C. for 15 hours. Then the resultant reaction mixture was cooled to room temperature, and was then distilled under a reduced pressure to remove an organic phase. The obtained crude product was purified by silica gel chromatography using a hexane/chloroform (1/2) mixed solvent as an eluent to give 0.46 g of the target 2-[3-(2,2'-bipyridin-6-yl)-5-(9-phenanthryl)phenyl]-4,6-diphenyl-1,3,5-triazine.

$^1$H-NMR (CDCl$_3$): δ.7.38 (brs, 1H), 7.59-7.66 (m, 7H), 7.73 (t, J=7.7 Hz, 1H), 7.75-7.78 (m, 2H), 7.89 (brs, 1H), 7.96 (s, 1H), 8.02-8.11 (m, 5H), 8.55 (brs, 1H), 8.66 (s, 1H), 8.76 (brd, J=7.9 Hz, 2H), 8.84 (d, J=7.7 Hz, 2H), 8.85 (d, J=7.8 Hz, 4H), 8.90 (d, J=8.4 Hz, 1H), 9.04 (s, 1H), 9.71 (s, 1H).

The obtained triazine derivative exhibited a Tg of 122° C.

Experiment Example 25

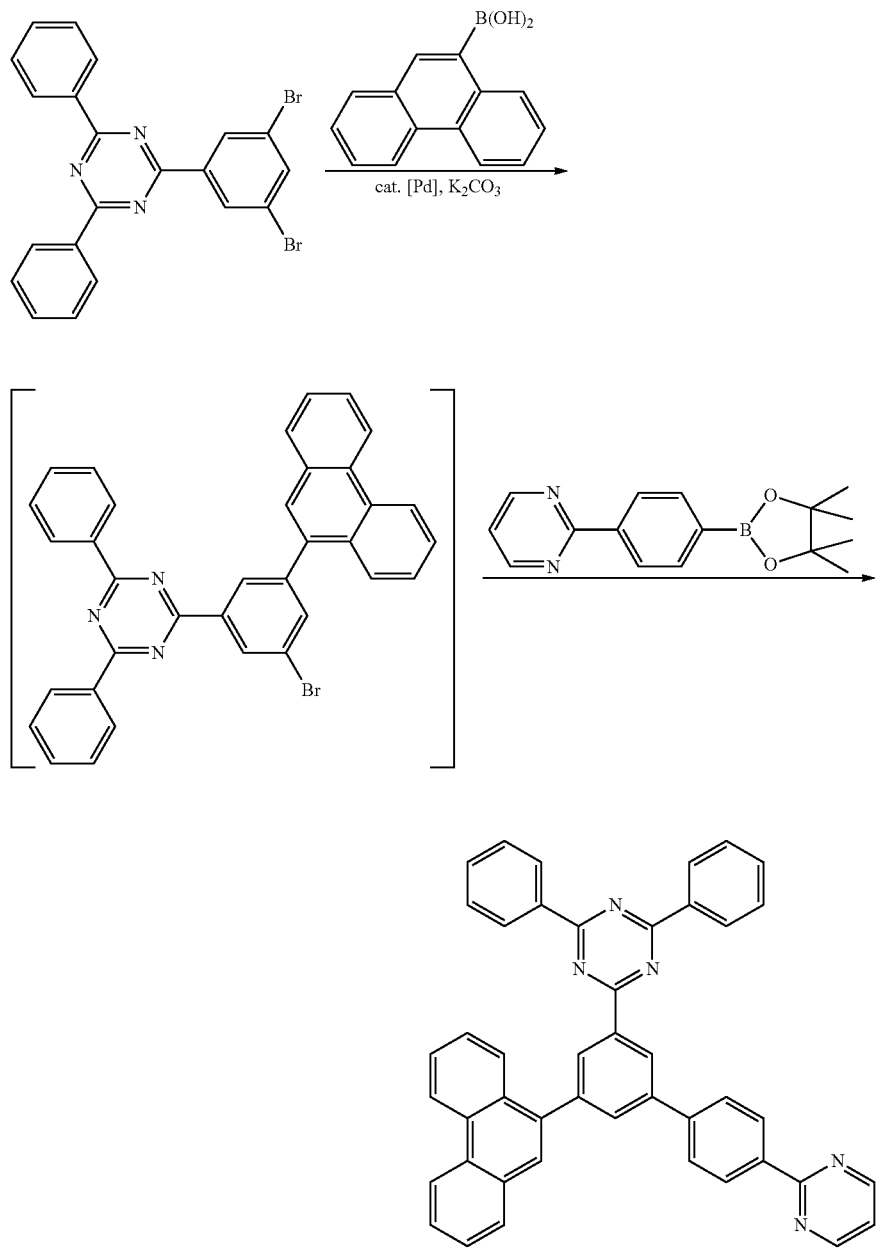

In a stream of argon, 143 mg (0.644 mmol) of 9-phenanthreneboronic acid, 300 mg (0.644 mmol) of 2-(3,5-dibromophenyl)-4,6-diphenyl-1,3,5-triazine and 7.44 mg (0.00644 mmol) of tetrakis(triphenylphosphine)palladium were suspended in a mixed solvent composed of 24 mL of toluene and 3 mL of ethanol, and the resultant suspension was heated to 60° C. To the suspension, 1.93 mL (1.93 mmol) of an aqueous 1M $K_2CO_3$ solution was gradually added dropwise, and the mixture was stirred for 3 hours. The resultant reaction mixture was cooled to room temperature, and then, 0.961 g (4.83 mmol) of 2-[4-(4,4,5,5-tetramethyl-1,3,2-dioxabororan-2-yl)phenyl]-pyrimidine and 9.66 mL (9.66 mmol) of an aqueous 1M $K_2CO_3$ solution were added to the reaction mixture. The resultant mixture was heated to 70° C., and maintained at that temperature for 19 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 214 mg of the target 4,6-diphenyl-2-[5-(9-phenanthryl)-4'-(2-pyrimidyl)biphenyl-3-yl]-1,3,5-triazine as a white solid (yield: 52%).

$^1$H-NMR (CDCl$_3$): δ7.22 (t, J=4.8 Hz, 1H), 7.54-7.63 (m, 7H), 7.67 (t, J=7.4 Hz, 1H), 7.73 (t, J=7.6 Hz, 2H), 7.90 (s, 1H), 7.96-7.99 (m, 3H), 8.03 (d, J=8.4 Hz, 1H), 8.10 (s, 1H), 8.62 (d, J=8.7 Hz, 2H), 8.79 (d, J=8.3 Hz, 2H), 8.79 (d, J=8.0 Hz, 2H), 8.79-8.80 (m, 1H), 8.85 (d, J=4.9 Hz, 2H), 8.84-8.86 (m, 1H) 8.95 (s, 1H), 9.19 (s, 1H).

Experiment Example 26

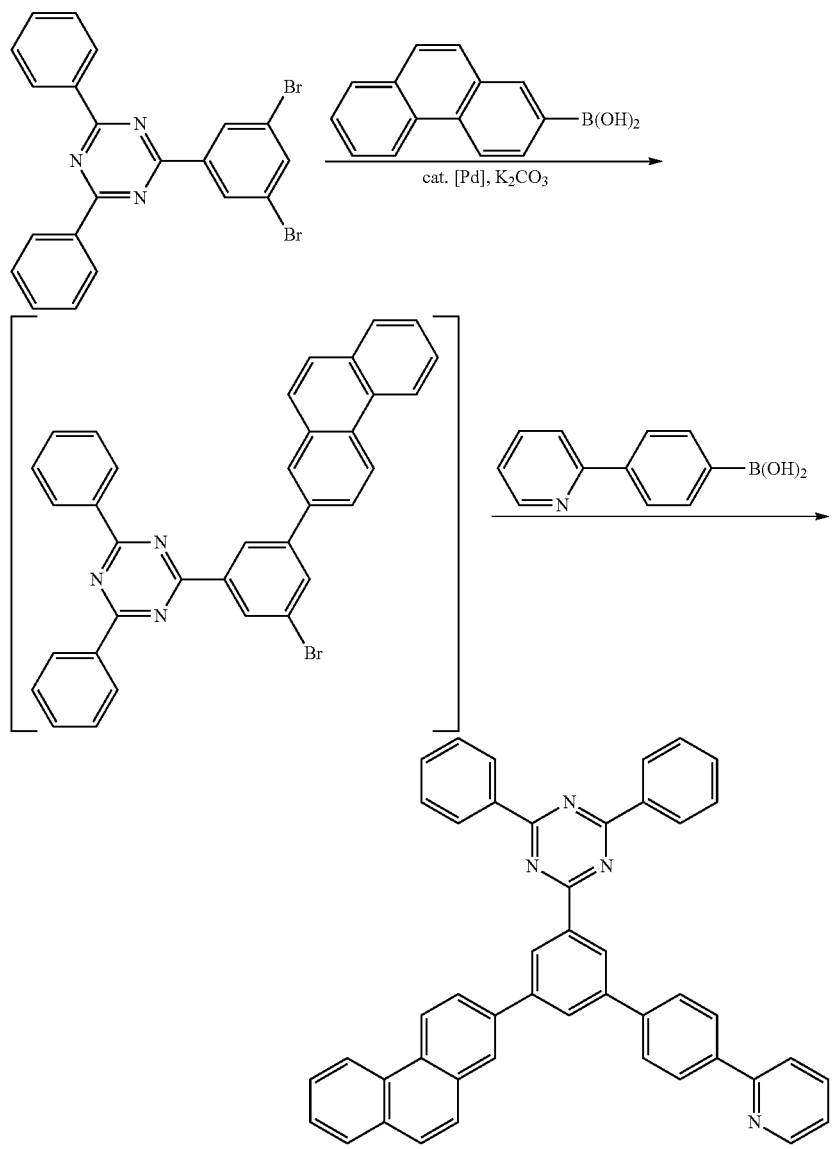

In a stream of argon, 77.6 mg (0.167 mmol) of 2-phenanthreneboronic acid, 37 mg (0.167 mmol) of 2-(3,5-dibromophenyl)-4,6-diphenyl-1,3,5-triazine and 5.78 mg (0.0050 mmol) of tetrakis(triphenylphosphine)palladium were suspended in a mixed solvent composed of 7 mL of toluene and 0.8 mL of ethanol, and the resultant suspension was heated to 50° C. To the suspension, 0.50 mL (0.50 mmol) of an aqueous 1M $K_2CO_3$ solution was gradually added dropwise, and the mixture was stirred for 2 hours. The resultant reaction mixture was cooled to room temperature, and then, 49.8 mg (0.25 mmol) of 4-(2-pyridyl)phenylboronic acid and 0.50 mL (0.50 mmol) of an aqueous 1M $K_2CO_3$ solution were added to the reaction mixture. The resultant mixture was heated to 60° C., and maintained at that temperature for 17 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 30 mg of the target 4,6-diphenyl-2-[5-(2-phenanthryl)-4'-(2-pyrimidyl)biphenyl-3-yl]-1,3,5-triazine as a white solid (yield: 28%).

$^1$H-NMR (CDCl$_3$): δ.7.26-7.30 (m, 1H), 7.52-7.66 (m, 7H), 7.69-7.72 (m, 1H), 7.77-7.85 (m, 3H), 7.89 (d, J=8.9 Hz, 1H), 7.95 (t, J=7.1 Hz, 1H), 7.96 (d, J=8.5 Hz, 2H), 8.11 (d, J=8.5 Hz, 2H), 8.20 (d, J=8.6 Hz, 2H), 8.24 (s, 1H), 8.29 (s, 1H), 8.74-8.76 (m, 2H), 8.81 (d, J=Hz, 2H), 8.82 (d, J=Hz, 2H), 8.84 (d, J=8.8 Hz, 1H), 9.06 (s, 1H), 9.12 (s, 1H).

Experiment Example 27

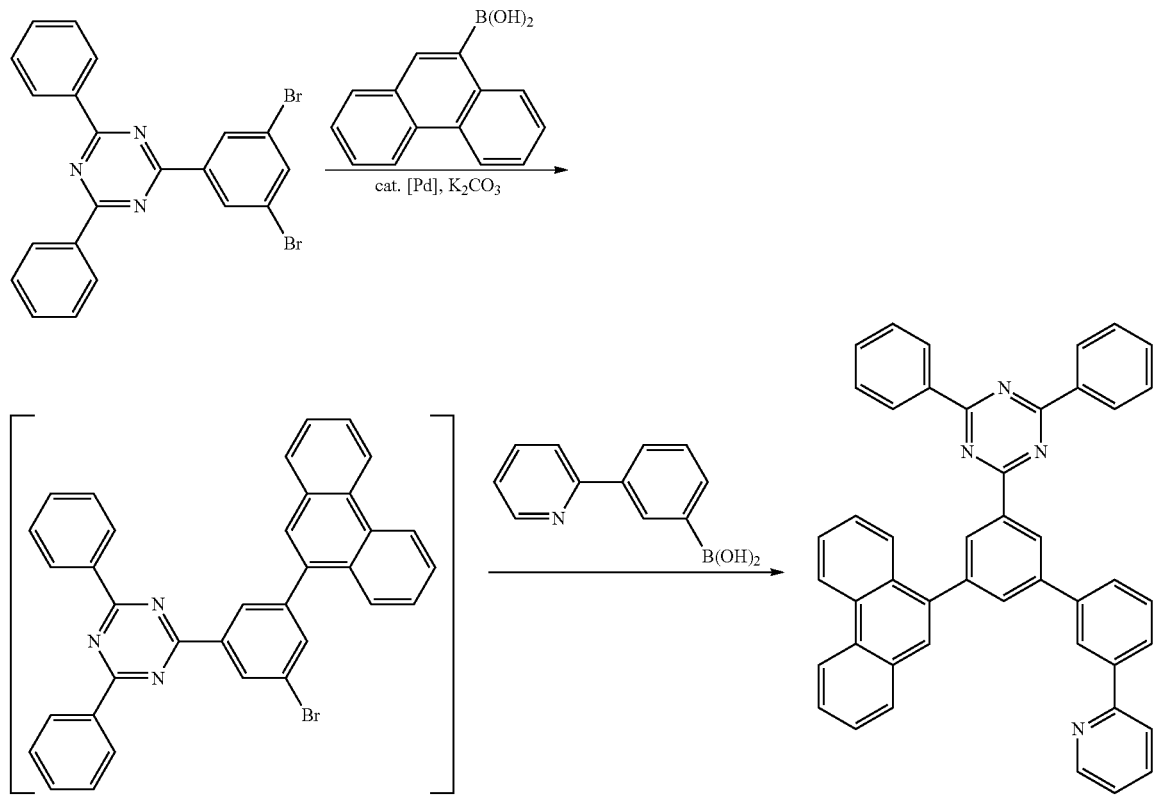

In a stream of argon, 5.00 g (10.7 mmol) of 9-phenanthreneboronic acid, 2.38 g (10.7 mmol) of 2-(3,5-dibromophenyl)-4,6-diphenyl-1,3,5-triazine and 124 mg (0.107 mmol) of tetrakis(triphenylphosphine)palladium were suspended in a mixed solvent composed of 400 mL of toluene and 50 mL of ethanol, and the resultant suspension was heated to 50° C. To the suspension, 32.1 mL (32.1 mmol) of an aqueous 1M $K_2CO_3$ solution was gradually added dropwise, and the mixture was stirred for 3 hours. The resultant reaction mixture was cooled to room temperature, and then, 3.19 g (10.7 mmol) of 3-(2-pyridyl)phenylboronic acid and 32.1 mL (32.1 mmol) of an aqueous 1M $K_2CO_3$ solution were added to the reaction mixture. The resultant mixture was heated to 60° C., and maintained at that temperature for 15 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 2.50 g of the target 4,6-diphenyl-2-[5-(9-phenanthryl)-3'-(2-pyridyl)biphenyl-3-yl]-1,3,5-triazine as a white solid (yield: 37%).

$^1$H-NMR ($CDCl_3$): δ.7.53-7.62 (m, 8H), 7.67 (t, J=7.7 Hz, 2H), 7.23 (t, J=8.2 Hz, 1H), 7.78 (t, J=7.9 Hz, 1H), 7.84 (d, J=7.9 Hz, 1H), 7.90 (s, 1H), 7.90 (d, J=8.4 Hz, 1H), 7.98 (d, J=7.8 Hz, 1H), 8.03 (d, J=8.2 Hz, 1H), 8.06 (d, J=7.8 Hz, 1H), 8.11 (s, 1H), 8.42 (s, 1H), 8.72 (d, J=4.9 Hz, 1H), 8.79 (d, J=8.3 Hz, 2H), 8.79 (d, J=8.2 Hz, 2H), 8.79 (m, 2H), 8.85 (d, J=8.2 Hz, 1H), 8.95 (s, 1H), 9.17 (s, 1H).

The obtained triazine derivative exhibited a Tg of 115° C.

Experiment Example 28

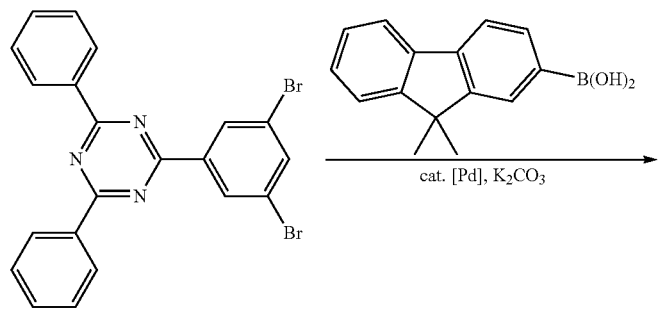

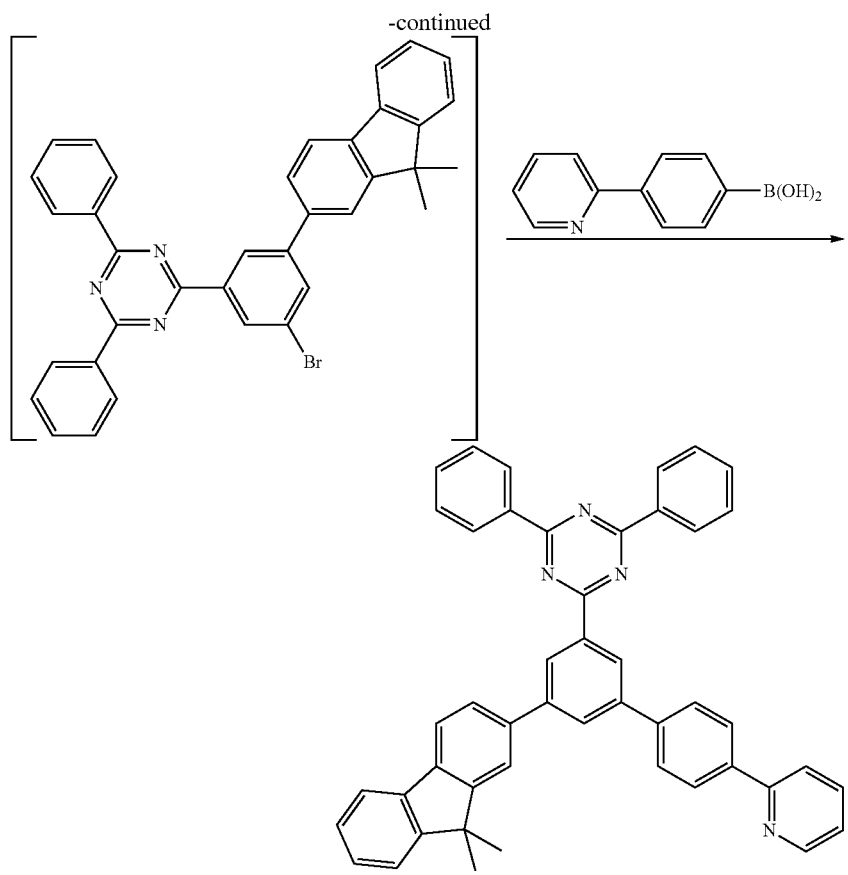

In a stream of argon, 0.95 g (4 mmol) of 9,9-dimethyl-2-fluoreneboronic acid, 1.87 g (4 mmol) of 2-(3,5-dibromophenyl)-4,6-diphenyl-1,3,5-triazine and 46.2 mg (0.04 mmol) of tetrakis(triphenylphosphine)palladium were suspended in a mixed solvent composed of 150 mL of toluene and 20 mL of ethanol, and the resultant suspension was heated to 50° C. To the suspension, 12 mL (12 mmol) of an aqueous 1M $K_2CO_3$ solution was gradually added dropwise, and the mixture was stirred for 18 hours. The resultant reaction mixture was cooled to room temperature, and then, 1.19 g (6 mmol) of 4-(2-pyridyl)phenylboronic acid and 12 mL (12 mmol) of an aqueous 1M $K_2CO_3$ solution were added to the reaction mixture. The resultant mixture was heated to 60° C., and maintained at that temperature for 2 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 1.61 g of the target 2-[5-(9,9-dimethylfluoren-2-yl)-4'-(2-pyridyl)biphenyl-3-yl]-4,6-diphenyl-1,3,5-triazine as a white solid (yield: 61.5%).

$^1$H-NMR (CDCl$_3$): δ.1.63 (s, 6H), 7.31 (dd, J=7.0, 4.8, 1H), 7.38-7.44 (m, 2H), 7.52 (d, J=6.5, H), 7.60-7.68 (m, 6H), 7.81-7.88 (m, 5H), 7.93 (d, J=7.8, 1H), 7.98 (d, J=8.5, 2H), 8.17 (s, H), 8.23 (d, J=8.5, 2H), 8.78 (d, J=4.8, 1H), 8.85 (d, J=8.1, 4H), 9.07 (s, 2H).

The obtained triazine derivative exhibited a Tg of 118° C.

Experiment Example 29

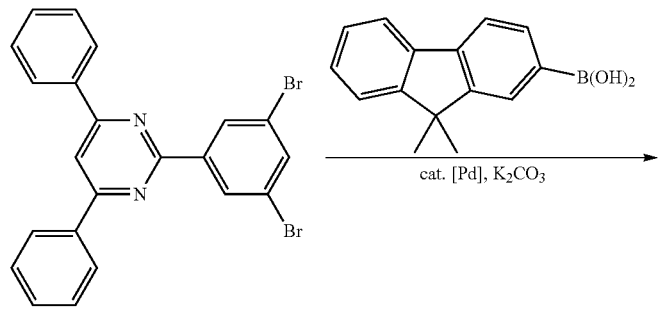

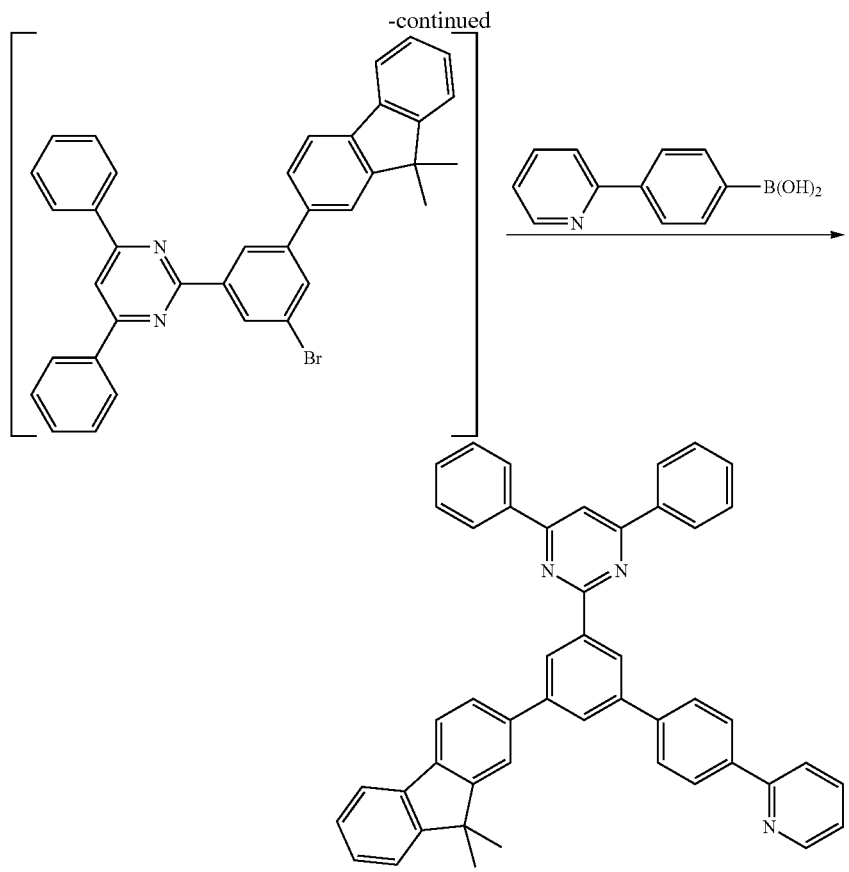

In a stream of argon, 0.71 g (3 mmol) of 9,9-dimethyl-2-fluoreneboronic acid, 1.4 g (3 mmol) of 2-(3,5-dibromophenyl)-4,6-diphenylpyrimidine and 34.7 mg (0.03 mmol) of tetrakis(triphenylphosphine)palladium were suspended in a mixed solvent composed of 115 mL of toluene and 15 mL of ethanol, and the resultant suspension was heated to 50° C. To the suspension, 9 mL (9 mmol) of an aqueous 1M $K_2CO_3$ solution was gradually added dropwise, and the mixture was stirred for 18 hours. The resultant reaction mixture was cooled to room temperature, and then, 0.896 g (4.5 mmol) of 4-(2-pyridyl)phenylboronic acid and 9 mL (9 mmol) of an aqueous 1M $K_2CO_3$ solution were added to the reaction mixture. The resultant mixture was heated to 60° C., and maintained at that temperature for 3.5 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.85 g of the target 2-[5-(9,9-dimethylfluoren-2-yl)-4'-(2-pyridyl)biphenyl-3-yl]-4,6-diphenylpyrimidine as a white solid (yield: 43.3%).

$^1$H-NMR (CDCl$_3$): δ.1.63 (s, 6H), 7.30 (d, J=5.7 Hz, 1H), 7.34-7.42 (m, 2H), 7.52 (d, J=6.6 Hz, 1H), 7.59-7.64 (m, 6H), 7.82-7.92 (m, 6H), 7.98 (d, J=8.4 Hz, 2H), 8.10 (d, J=6.8 Hz, 2H), 8.21 (d, J=8.4 Hz, 2H), 8.37 (d, J=6.3 Hz, 4H), 8.78 (d, J=4.8 Hz, 1H), 9.04 (s, 2H).

Experiment Example 30

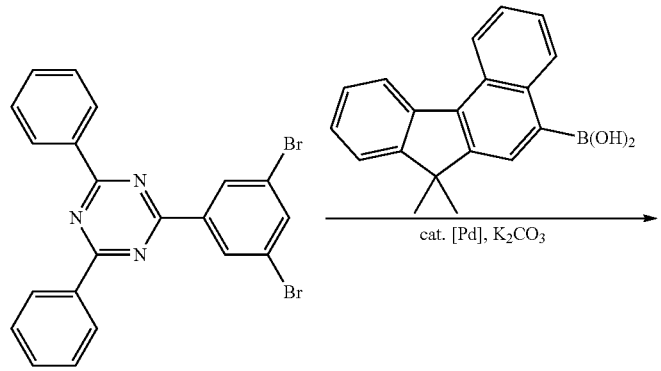

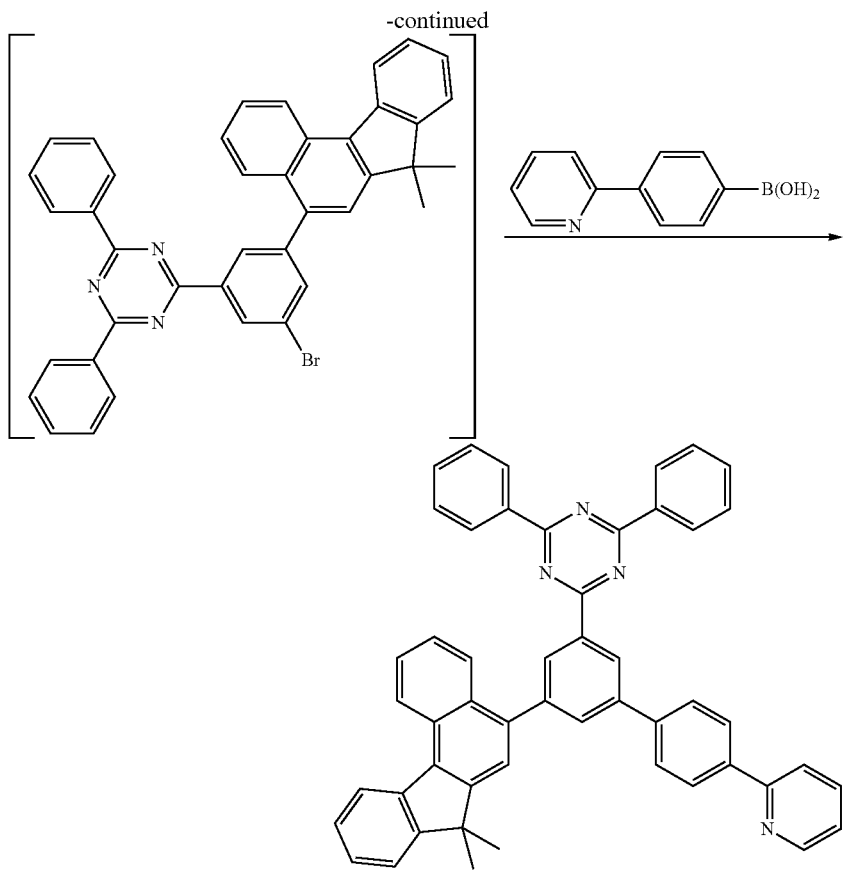

In a stream of argon, 185 mg (0.644 mmol) of 9,9-dimethyl-2-benzo[c]fluoreneboronic acid, 300 mg (0.644 mmol) of 2-(3,5-dibromophenyl)-4,6-diphenyl-1,3,5-triazine and 7.44 mg (0.00644 mmol) of tetrakis(triphenylphosphine)palladium were suspended in a mixed solvent composed of 24 mL of toluene and 3 mL of ethanol, and the resultant suspension was heated to 50° C. To the suspension, 1.93 ml (1.93 mmol) of an aqueous 1M $K_2CO_3$ solution was gradually added dropwise, and the mixture was stirred for 3 hours. The resultant reaction mixture was heated to 80° C. and further stirred for 3 hours. The reaction mixture was cooled to room temperature, and then, 256 mg (1.29 mmol) of 4-(2-pyridyl)phenylboronic acid and 2.90 mL (2.90 mmol) of an aqueous 1M $K_2CO_3$ solution were added to the reaction mixture. The resultant mixture was heated to 80° C., and maintained at that temperature for 24 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 172 mg of the target 2-[5-(9,9-dimethylbenzo[c]fluoren-2-yl)-4'-(2-pyridyl)biphenyl-3-yl]-4,6-diphenyl-1,3,5-triazine as a white solid (yield: 38.0%).

$^1$H-NMR (CDCl$_3$): δ.1.63 (s, 6H), 7.25-7.29 (m, 1H), 7.42 (t, J=7.4 Hz, 1H), 7.49-7.64 (m, 9H), 7.69-7.73 (m, 1H), 7.74 (s, 1H), 7.79 (t, J=8.1 Hz, 1H), 7.83 (d, J=7.7 Hz, 1H), 7.97 (d, J=8.7 Hz, 2H), 8.08 (s, 1H), 8.11 (d, J=7.8 Hz, 1H), 8.20 (d, J=8.6 Hz, 2H), 8.43 (d, J=7.8 Hz, 1H), 8.75 (d, J=4.9 Hz, 1H), 8.79 (d, J=8.3 Hz, 2H), 8.80 (d, J=8.1 Hz, 2H), 8.91 (d, J=8.5 Hz, 1H), 8.94 (s, 1H), 9.18 (s, 1H).

Experiment Example 31

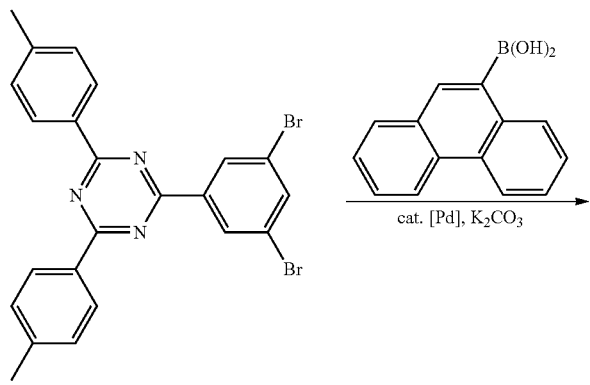

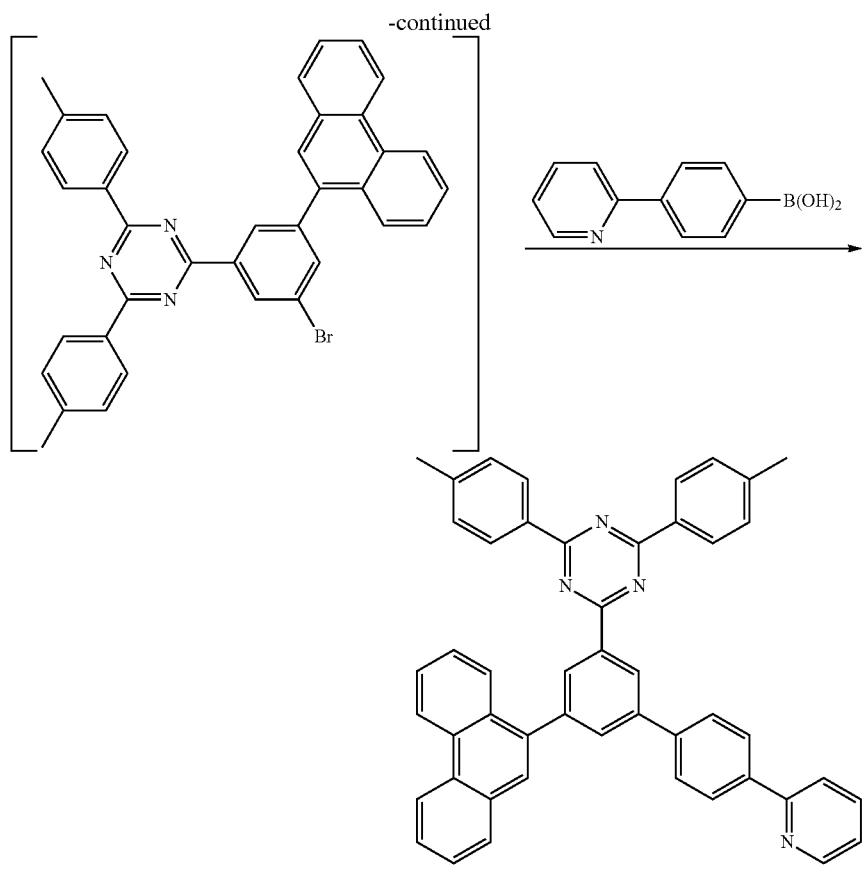

In a stream of argon, 0.538 g (2.42 mmol) of 9-phenanthreneboronic acid, 1.20 g (2.42 mmol) of 2-(3,5-dibromophenyl)-4,6-di-p-tolyl-1,3,5-triazine and 28.0 mg (0.0242 mmol) of tetrakis(triphenylphosphine)palladium were suspended in a mixed solvent composed of 90 mL of toluene and 10 mL of ethanol, and the resultant suspension was heated to 50° C. To the suspension, 7.26 mL (7.26 mmol) of an aqueous 1M $K_2CO_3$ solution was gradually added dropwise, and the mixture was stirred for 3 hours. The resultant reaction mixture was cooled to room temperature, and then, 0.722 g (3.63 mmol) of 4-(2-pyridyl)phenylboronic acid and 7.26 mL (7.26 mmol) of an aqueous 1M $K_2CO_3$ solution were added to the reaction mixture. The resultant mixture was heated to 60° C., and maintained at that temperature for 15 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (1:2) mixed solvent as an eluent to give 0.680 g of the target 4,6-di-p-tolyl-2-[5-(9-phenanthryl)-4'-(2-pyridyl)biphenyl-3-yl]-1,3,5-triazine as a white solid (yield: 42%).

$^1$H-NMR (CDCl$_3$): δ.2.47 (s, 6H), 7.25-7.28 (m, 1H), 7.35 (d, J=8.0 Hz, 4H), 7.60 (t, J=7.7 Hz, 1H), 7.67 (t, J=7.4 Hz, 1H), 7.73 (t, J=7.4 Hz, 1H), 7.73 (t, J=7.4 Hz, 1H), 7.79 (t, J=7.8 Hz, 1H), 7.83 (d, J=7.8 Hz, 1H), 7.90 (s, 1H), 7.95 (d, J=8.4 Hz, 2H), 7.98 (d, J=8.0 Hz, 1H), 8.04 (d, J=7.9 Hz, 1H), 8.07 (s, 1H), 8.18 (d, J=8.5 Hz, 2H), 8.66 (d, J=8.1 Hz, 4H), 8.74 (d, J=5.0 Hz, 1H), 8.79 (d, J=8.4 Hz, 1H), 8.85 (d, J=8.0 Hz, 1H), 8.92 (s, 1H), 9.16 (s, 1H).

Experiment Example 32

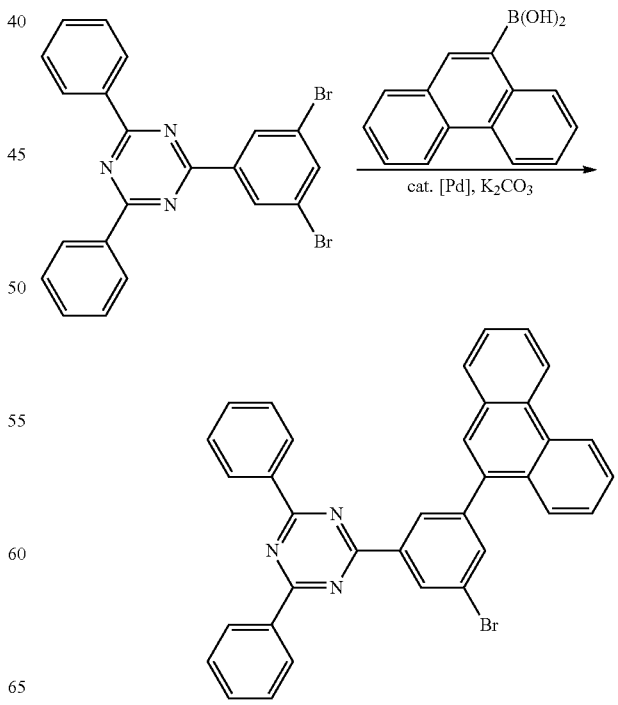

In a stream of argon, 0.71 g (3.21 mmol) of 9-phenanthreneboronic acid, 1.50 g (3.21 mmol) of 2-(3,5-dibromophenyl)-4,6-diphenyl-1,3,5-triazine and 37.0 mg (0.0321 mmol) of tetrakis(triphenylphosphine)palladium were suspended in a mixed solvent composed of 120 mL of toluene and 15 mL of ethanol, and the resultant suspension was heated to 60° C. and maintained at that temperature for 12 hours while being stirred. The obtained reaction mixture was cooled to room temperature, and then distilled under a reduced pressure to remove all volatile materials. Methanol was added to the concentrate, and the thus-deposited solid was collected by filtration. The obtained crude product was purified by silica gel chromatography using a hexane/chloroform (2:1) mixed solvent as an eluent to give 0.54 g of the target 4,6-diphenyl-2-[5-(9-phenanthryl)-3-bromophenyl]-1,3,5-triazine as a white solid (yield: 30%).

$^1$H-NMR (CDCl$_3$): δ.7.57-7.76 (m, 10H), 7.82 (s, 1H), 7.93-7.89 (m, 3H), 8.78 (d, J=8.0 Hz, 4H), 8.80 (d, J=8.2 Hz, 1H), 8.85 (d, J=8.2 Hz, 1H), 8.90 (s, 1H), 9.02 (s, 1H).

Experiment Example 33

Measurement of Tg of 2-{4,4''-di(2-pyridyl)-[1,1':3',1'']-terphenyl-5'-yl}-4,6-di-p-tolyl-1,3,5-triazine

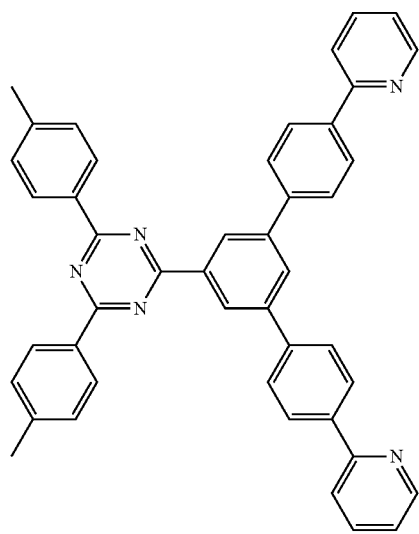 [SMILES: Cc1ccc(-c2nc(-c3ccc(C)cc3)nc(-c3cc(-c4ccc(-c5ccccn5)cc4)cc(-c4ccc(-c5ccccn5)cc4)c3)n2)cc1]

Thermal analysis of 2-{4,4''-di(2-pyridyl)-[1,1':3',1'']-terphenyl-5'-yl}-4,6-di-p-tolyl-1,3,5-triazine, which is described in patent document 1, revealed that its Tg was 108° C.

Experiment Example 34

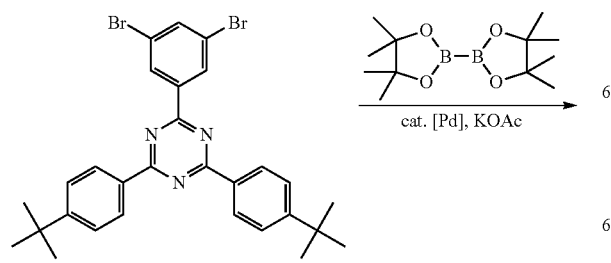

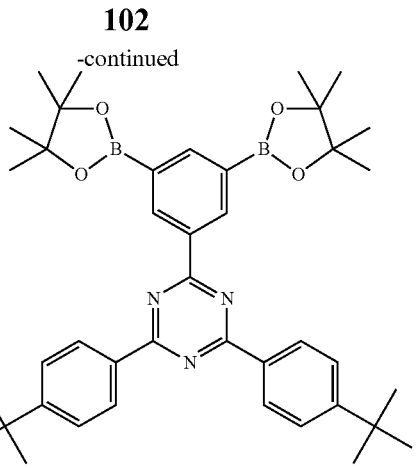

In a stream of argon, 195 mg of 4,6-bis(4-tert-butylphenyl)-2-(3,5-dibromophenyl)-1,3,5-triazine, 188 mg of bispinacolatediboron, 159 mg of potassium acetate and 9.48 mg of dichlorobistriphenylphosphinepalladium were suspended in 10 mL of tetrahydrofuran, and the obtained suspension was heated under reflux for 38 hours. The obtained reaction mixture was cooled to room temperature, and then distilled under a reduced pressure to remove all volatile materials. The obtained crude product was purified by silica gel chromatography using chloroform as an eluent and washed with hexane to give 170 mg of 4,6-bis(4-tert-butylphenyl)-2-[3,5-bis(4,4,5,5-tetramethyl-1,3,2-dioxaboroan-2-yl)phenyl]-1,3,5-triazine as a yellow solid (yield: 75%).

$^1$H-NMR (CDCl$_3$): δ1.43 (s, 18H), 1.44 (s, 24H), 7.64 (d, J=8.6 Hz, 4H), 8.52 (t, J=1.2 Hz, 1H), 8.74 (d, J=8.6 Hz, 4H), 9.23 (d, J=1.2 Hz, 2H).

Experiment Example 35

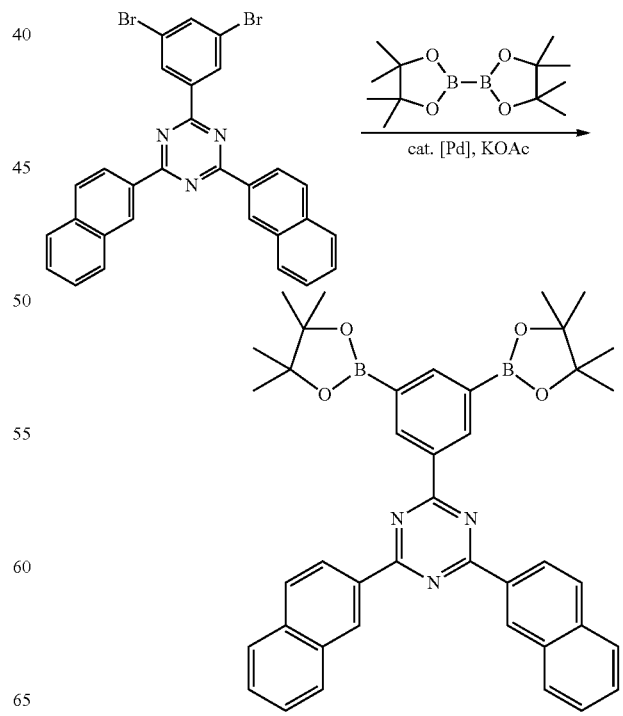

In a stream of argon, 1.00 g of 2-(3,5-dibromophenyl)-4,6-di(2-naphthyl)-1,3,5-triazine, 996 mg of bispinacolatediboron, 830 mg of potassium acetate and 61.8 mg of dichlorobistriphenylphosphinepalladium were suspended in 50 mL of tetrahydrofuran, and the obtained suspension was heated under reflux for 41 hours. The obtained reaction mixture was cooled to room temperature, and then distilled under a reduced pressure to remove all volatile materials. The thus-obtained crude product was purified by silica gel chromatography using chloroform as an eluent to give 1.01 mg of 2-[3,5-bis(4,4,5,5-tetramethyl-1,3,2-dioxabororan-2-yl)phenyl]-4,6-di(2-dinaphthyl)-1,3,5-triazine as a yellow solid (yield: 87%).

$^1$H-NMR (CDCl$_3$): δ1.37 (s, 24H), 7.51-7.57 (m, 4H), 7.89 (brd, J=7.7 Hz, 2H), 8.01 (d, J=8.7 Hz, 2H), 8.09 (brd, J=7.7 Hz, 2H), 8.48 (t, J=1.2 Hz, 1H), 8.85 (dd, J=8.7, 1.7 Hz, 2H), 9.24 (d, J=1.2 Hz, 2H), 9.36 (brs, 2H).

Experiment Example 36

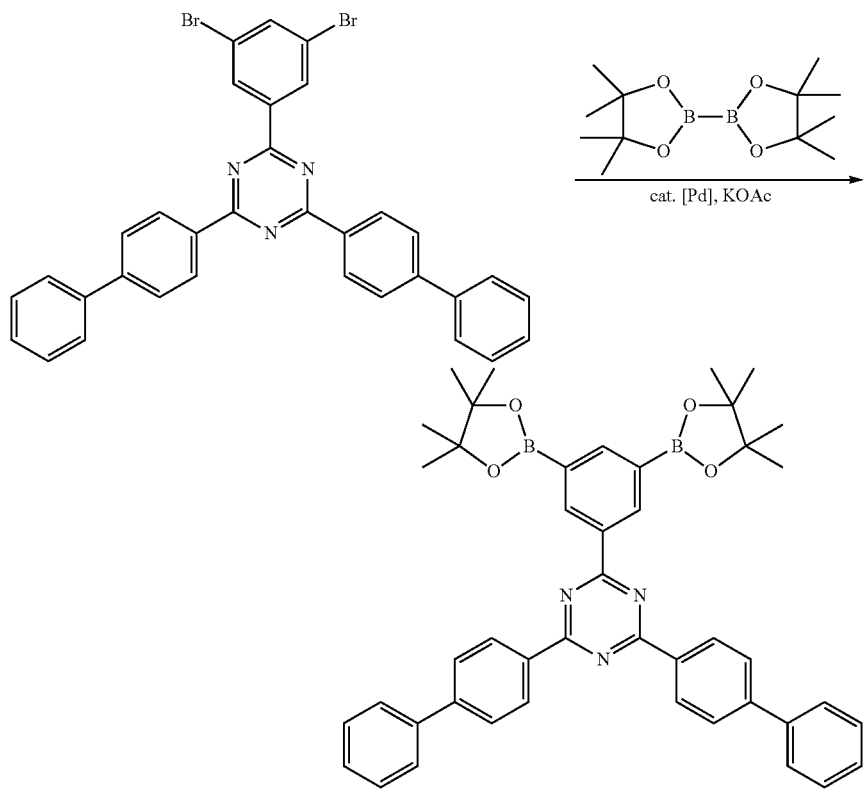

In a stream of argon, 300 mg of 2,4-bis(4-biphenylyl)-6-(3,5-dibromophenyl)-1,3,5-triazine, 270 mg of bispinacolatediboron, 228 mg of potassium acetate and 17.0 mg of dichlorobistriphenylphosphinepalladium were suspended in 20 mL of dioxane, and the obtained suspension was heated under reflux for 24 hours. The obtained reaction mixture was cooled to room temperature, and then distilled under a reduced pressure to remove all volatile materials. The thus-obtained crude product was purified by silica gel chromatography using chloroform as an eluent and then washed with hexane to give 250 mg of 4,6-bis(4-biphenylyl)-2-[3,5-bis(4,4,5,5-tetramethyl-1,3,2-dioxabororan-2-yl)phenyl]-1,3,5-triazine as a yellow solid (yield: 72%).

$^1$H-NMR (CDCl$_3$): δ1.45 (s, 24H), 7.44 (brt, J=7.4 Hz, 2H), 7.54 (t, J=7.4 Hz, 4H), 7.76 (d, J=7.4 Hz, 4H), 7.87 (d, J=8.5 Hz, 4H), 8.56 (t, J=1.2 Hz, 1H), 8.93 (d, J=8.5 Hz, 4H), 9.28 (d, J=1.2 Hz, 2H).

Experiment Example 37

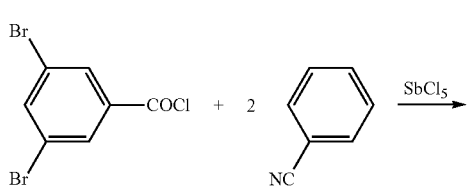

-continued

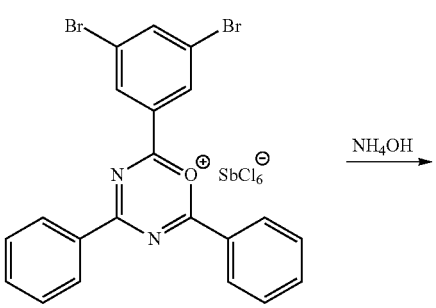

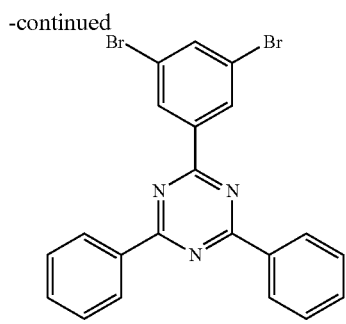

5.97 g of 3,5-dibromobenzoyl chloride and 4.12 g of benzonitrile were dissolved in 50 mL of chloroform, and the obtained solution was cooled to 0° C. 5.98 g of antimony pentachloride was added dropwise to the cooled solution. The obtained mixed liquid was stirred at room temperature for 10 minutes, and then, heated under reflux for 22 hours. The obtained reaction mixture was cooled to room temperature, and then distilled under a reduced pressure to remove chloroform to give a yellow solid.

The yellow solid was added to 300 mL of aqueous 28% ammonia maintained at 0° C. to give a white solid. The aqueous liquid was stirred at room temperature for 1 hour and then filtered. The obtained white solid product was washed with water and then with methanol. The thus-obtained white solid was purified by silica gel chromatography to give 6.32 g of 2-(3,5-dibromophenyl)-4,6-diphenyl-1,3,5-triazine as a white solid (yield: 680).

$^1$H-NMR (CDCl$_3$): δ7.56-7.61 (m, 4H), 7.61-7.67 (m, 2H), 7.90 (t, J=1.8 Hz, 1H), 8.72-8.78 (m, 4H), 8.82 (d, J=1.8 Hz, 2H).

$^{13}$C-NMR (CDCl$_3$): δ123.4, 128.8, 129.1, 130.6, 133.0, 135.7, 137.6, 139.8, 169.3, 172.0.

Experiment Example 38

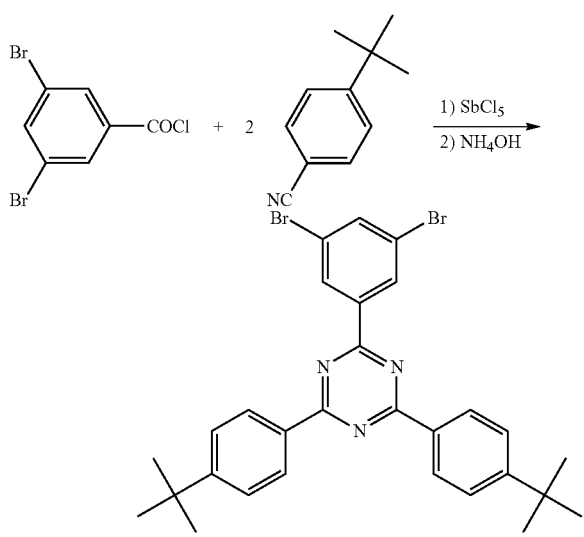

2.98 g of 3,5-dibromobenzoyl chloride and 3.18 g of 4-tert-butylbenzonitrile were dissolved in 30 mL of chloroform. The obtained solution was cooled to 0° C., and 2.99 g of antimony pentachloride was added dropwise to the cooled solution. The obtained mixed liquid was stirred at room temperature for 10 minutes, and then, heated under reflux for 17 hours. The obtained reaction mixture was cooled to room temperature, and then distilled under a reduced pressure to remove chloroform to give a solid product.

The solid product was added to 200 mL of aqueous 28% ammonia maintained at 0° C. to give a white precipitate. The aqueous liquid was stirred at room temperature for 1 hour and then filtered. The obtained white precipitate was washed with water and then with methanol. The thus-obtained white precipitate was purified by silica gel chromatography to give 4.46 g of 4,6-bis(4-tert-butylphenyl)-2-(3,5-dibromophenyl)-1,3,5-triazine as a white solid (yield: 770).

$^1$H-NMR (CDCl$_3$): δ1.41 (s, 18H), 7.61 (d, J=8.5 Hz, 4H), 7.88 (t, J=1.8 Hz, 1H), 8.65 (d, J=8.5 Hz, 4H), 8.80 (d, J=1.8 Hz, 2H).

$^{13}$C-NMR (CDCl$_3$): δ31.2, 35.1, 123.3, 125.7, 128.9, 130.5, 133.1, 137.4, 140.0, 156.5, 169.0, 171.8.

Experiment Example 39

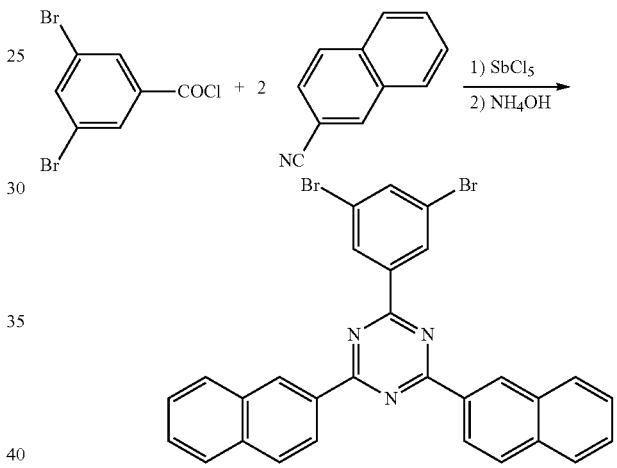

In a stream of argon, a three-necked reaction flask equipped with a reflux condenser and a mechanical stirrer was charged with 19.9 g of 3,5-dibromobenzoyl chloride and 20.4 g of 2-cyanonaphthalene, and then, 180 mL of chlorobenzene was added to the content. The obtained solution was cooled to 0° C., and 19.9 g of antimony pentachloride was added dropwise to the solution. The obtained mixture was stirred at room temperature for 30 minutes, and further stirred at 100° C. for 2 hours. The thus-obtained dark red suspension was cooled to −20° C., and 100 mL of 28% aqueous ammonia was added to the cooled suspension. The obtained milky white suspension was stirred at room temperature for 1 hour, and then heated to 140° C. to remove 70 mL of the organic solvent and 30 mL of water. The reaction mixture was left to stand and filtered.

The obtained solid was suspended in 100 mL of chlorobenzene. The suspension was heated to 130° C. and filtered to remove insolubles. This procedure of suspending in 100 mL of chlorobenzene, followed by heating and filtration to remove insolubles was repeated further 3 times. The filtrates were left to stand, and joined together. 400 mL of methanol was added to the joined filtrate to precipitate. The precipitate was collected by filtration, and washed with 300 mL of methanol two times. The precipitate was dried to give 7.90 g of 4,6-di(2-dinaphthyl)-2-(3,5-dibromophenyl)-1,3,5-triazine as a white powder (yield: 14%).

The insolubles obtained by heating and filtration of the suspension in chloroform were subjected to extraction using a soxhlet extractor and chloroform as extracting solvent to give 5.40 g of 2-(3,5-dibromophenyl)-4,6-di(2-dinaphthyl)-1,3,5-triazine as a white powder (yield: 9.5%).

$^1$H-NMR (CDCl$_3$): δ7.60-7.69 (m, 4H), 7.94 (s, 1H), 7.98 (d, J=7.8 Hz, 2H), 8.06 (d, J=8.6 Hz, 2H), 8.17 (d, J=7.8 Hz, 2H), 8.83 (d, J=8.6 Hz, 2H), 8.90 (s, 2H), 9.34 (s, 2H).

Experiment Example 40

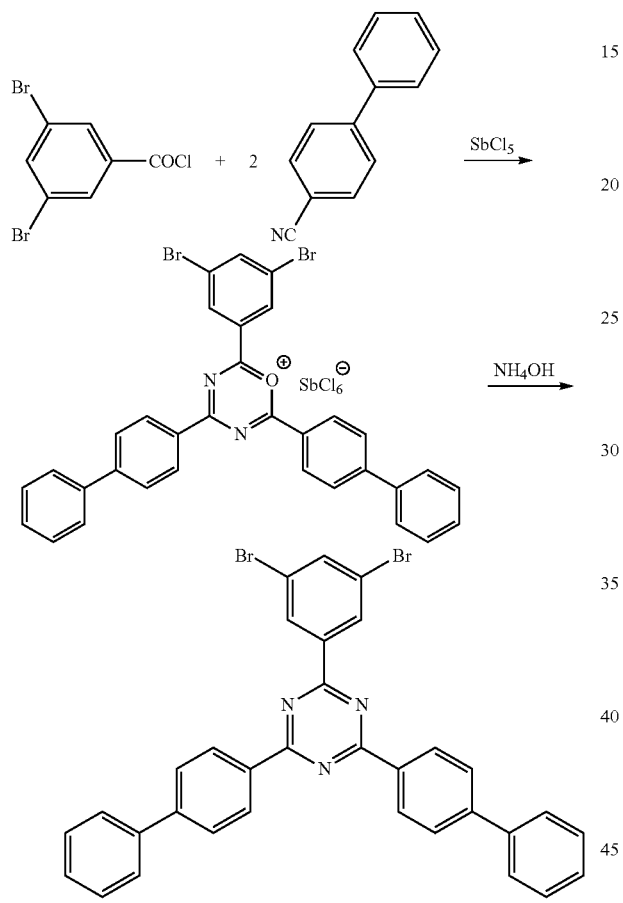

2.98 g of 3,5-dibromobenzoyl chloride and 3.58 g of 4-biphenylcarbonitrile were dissolved in 40 mL of chloroform. The obtained solution was cooled to 0° C., and 2.99 g of antimony pentachloride was added dropwise to the cooled solution. The obtained mixed liquid was stirred at room temperature for 10 minutes, and then, heated under reflux for 14 hours. The obtained reaction mixture was cooled to room temperature, and then distilled under a reduced pressure to remove chloroform to give 4,6-bis(4-biphenylyl)-2-(3,5-dibromophenyl)-1,3,5-oxadiazin-1-ium=hexachloroantimonate as a red solid.

The obtained red solid was added to 150 mL of aqueous 28% ammonia maintained at 0° C. to give a white precipitate. The aqueous liquid was stirred at room temperature for 1 hour and then filtered. The obtained white precipitate was washed with water and then with methanol. The thus-obtained white precipitate was dried, and then suspended in 200 mL of chloroform. The suspension was heated and then filtered. The insolubles collected by filtration were suspended in 150 ml of chloroform and the obtained suspension was filtered. This procedure of suspending in 150 mL of chloroform, followed by heating and filtration was repeated 3 times. All of the filtrates were joined together, and then distilled under reduced pressure to remove chloroform. The thus-obtained solid product was recrystallized from dichloromethane-methanol to give 5.14 g of 4,6-bis(4-biphenylyl)-2-(3,5-dibromophenyl)-1,3,5-triazine as a white solid (yield: 83%).

$^1$H-NMR (CDCl$_3$): δ7.40-7.45 (m, 2H), 7.49-7.54 (m, 4H), 7.70-7.75 (m, 4H), 7.83 (d, J=8.5 Hz, 4H), 7.91 (t, J=1.8 Hz, 1H), 8.83 (d, J=8.5 Hz, 4H), 8.85 (d, J=1.8 Hz, 2H).

$^{13}$C-NMR (CDCl$_3$): δ123.4, 127.3, 127.5, 128.2, 129.0, 129.7, 130.7, 134.7, 137.6, 139.9, 140.3, 145.7, 169.3, 171.8.

Experiment Example 41

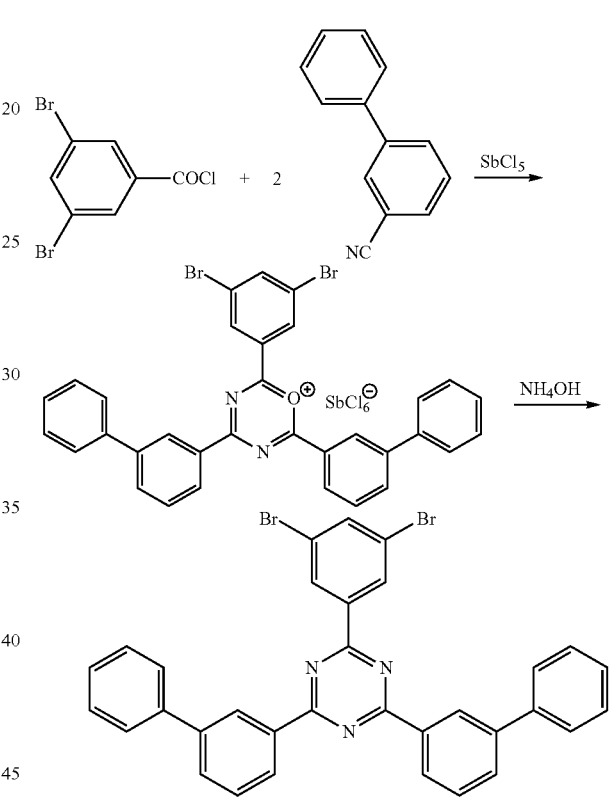

4.10 g of 3,5-dibromobenzoyl chloride and 5.00 g of 3-biphenylcarbonitrile were dissolved in 100 mL of chloroform in a stream of argon. The obtained solution was cooled to 0° C., and 4.20 g of antimony pentachloride was added dropwise to the cooled solution. The obtained mixed liquid was stirred at room temperature for 1 hour, and then, heated under reflux for 12 hours. The obtained reaction mixture was cooled to room temperature, and then distilled under a reduced pressure to remove all volatile materials to give a red solid.

The obtained red solid was pulverized in a stream of argon and added to aqueous 28% ammonia maintained at 0° C. The thus-obtained suspension was further stirred at room temperature for 1 hour and then filtered. The obtained precipitate was washed with water and then with methanol. The thus-obtained precipitate was dried, and then subjected to extraction using a soxhlet extractor and chloroform as extracting solvent. The extracted liquid was left to stand to be thereby cooled, and the deposited solid was collected by filtration. The obtained solid was dried to give 2.80 g of 4,6-bis(3-biphenylyl)-2-(3,5-dibromophenyl)-1,3,5-triazine as a white powder (yield: 32%).

$^1$H-NMR (CDCl$_3$): δ7.46 (brt, J=7.4 Hz, 2H), 7.52-7.58 (m, 4H), 7.67 (dd, J=7.8 Hz, 7.7 Hz, 2H), 7.76 (brd, J=7.7 Hz, 4H), 7.86 (d, J=7.7 Hz, 2H), 7.90 (brd, 1H), 8.72 (d, J=7.8 Hz, 2H), 8.81 (d, J=1.8 Hz, 2H), 8.95 (s, 2H).

$^{13}$C-NMR (CDCl$_3$): δ123.4, 127.4, 127.7, 127.8, 128.1, 130.7, 131.7, 136.2, 137.7, 139.7, 140.7, 141.9, 169.4, 172.0.

Experiment Example 42

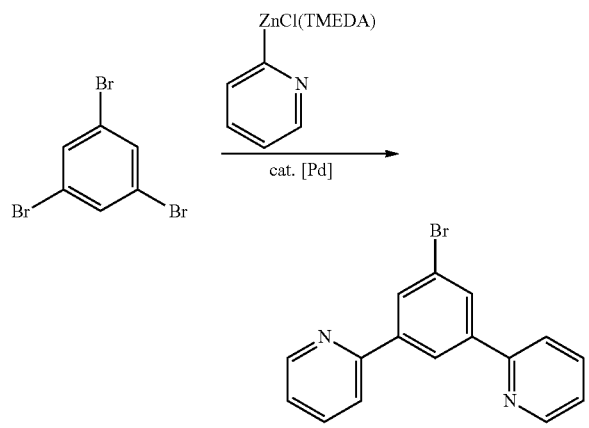

In a stream of argon, 89 mL of a 1.57M tert-butyllithium pentane solution was dissolved in 32 mL of tetrahydrofuran, and the solution was cooled to −78° C. 10.0 g of 2-bromopyridine was added dropwise to the solution, and the mixture was stirred for 1.5 hours. 42.5 g of dichloro(tetramethylethylenediamine)zinc was added to the mixture, and the temperature of the resultant mixture was elevated to room temperature, and the mixture was further stirred for 1 hour. To the resultant mixture, a suspension of 10.0 g of 1,3,5-tribromobenzene and 734 mg of tetrakis(triphenylphosphine)palladium in 64 mL of tetrahydrofuran was added. The obtained mixture was heated under reflux for 17 hours while being stirred. Then the obtained reaction mixture was cooled to room temperature, and was then distilled under a reduced pressure to remove all volatile materials. Water and chloroform were added to the concentrate, and the organic phase was separated and distilled to remove the solvent. The thus-obtained crude product was purified by silica gel chromatography using an ethyl acetate/hexane (2:8-1:1) mixed solvent to give 6.5 g of the target 3,5-di(2-pyridyl)bromobenzene as a yellow solid (yield: 66%).

$^1$H-NMR (CDCl$_3$): δ7.22 (dd, J=8.6, 5.8, 2H), 7.77-7.80 (m, 4H), 8.16 (s, 2H), 8.50 (t, J=1.6 Hz, 1H), 8.66 (d, J=4.8 Hz, 2H).

Experiment Example 43

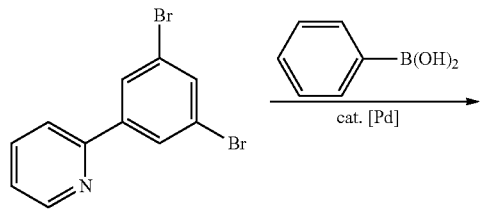

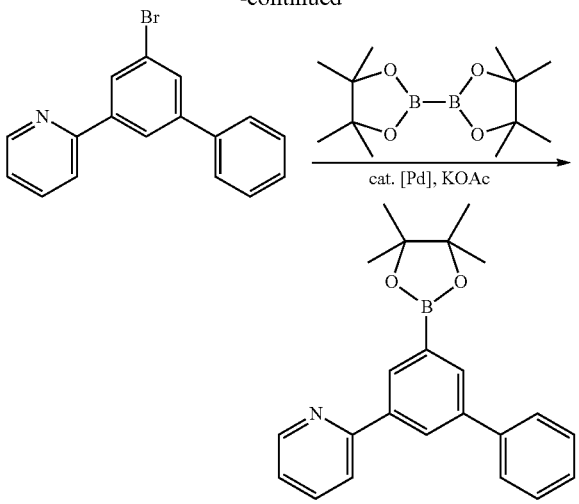

In a stream of argon, 3.80 g of phenylboronic acid, 8.15 g of 2-(3,5-dibromophenyl)pyridine and 1.20 g of tetrakis(triphenylphosphine)palladium were suspended in a mixed solvent comprised of 26 mL of an aqueous 2M sodium carbonate solution, 26 mL of ethanol and 52 mL of toluene, and the obtained mixture was distilled under reflux for 22 hours. The resultant reaction mixture was cooled to room temperature, and then distilled under a reduced pressure to remove all volatile materials. Water and chloroform were added to the concentrate, and the organic phase was separated and distilled to remove the solvent. The thus-obtained crude product was purified by silica gel chromatography using a hexane/chloroform (1:1) mixed solvent as an eluent to give 3.95 g of 2-(3-bromophenyl-5-yl)pyridine as a yellow liquid (yield: 43%).

In a stream of argon, 3.95 g of 2-(3-bromophenyl-5-yl)pyridine, 3.37 g of bispinacolatediboron, 3.26 g of potassium acetate and 0.31 g of dichlorobistriphenylphosphinepalladium were suspended in 60 mL of tetrahydrofuran, and the suspension was heated under reflux for 43 hours. The obtained reaction mixture was cooled to room temperature, and was then distilled under a reduced pressure to remove all volatile materials. The thus-obtained crude product was purified by silica gel chromatography using chloroform as an eluent to give 1.55 g of the target 2-[3-(4,4,5,5-tetramethyl-1,3,2-dioxabororan-2-yl)-biphenyl-5-yl]pyridine as a yellow solid (yield: 99%).

$^1$H-NMR (CDCl$_3$): δ1.31 (s, 12H), 7.16-7.20 (m, 1H), 7.28 (tt, J=7.4, 1.2 Hz, 1H), 7.36-7.39 (m, 1H), 7.65 (dd, J=8.3, 1.2 Hz, 1H), 7.70 (dd, J=7.5, 1.8 Hz, 1H), 7.78 (dt, J=8.0, 1.0 Hz, 1H), 8.03 (dd, J=1.9, 1.0 Hz, 1H), 8.29-8.30 (m, 1H), 8.31 (t, J=1.9 Hz, 1H), 8.65 (ddd, J=4.8, 1.8, 0.9 Hz, 1H).

Experiment Example 44

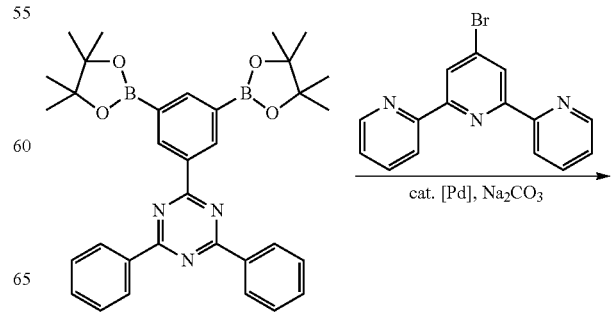

-continued

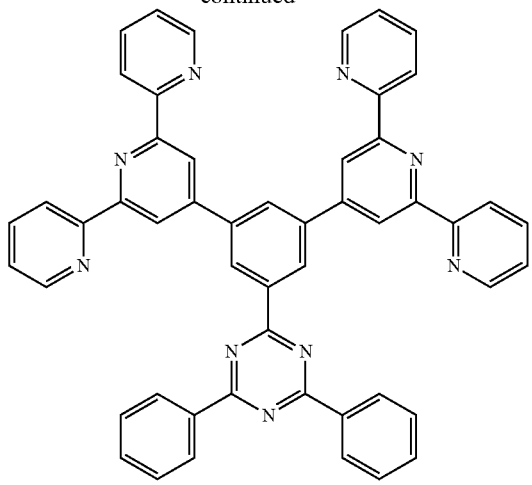

In a stream of argon, 1.00 g of 2-[3,5-bis(4,4,5,5-tetramethyl-1,3,2-dioxabororan-2-yl)phenyl]-4,6-diphenyl-1,3,5-triazine, 1.33 g of 4'-bromo-2,2':6',2"-terpyridine and 165 mg of tetrakis(triphenylphosphine)palladium were suspended in a mixed solvent comprised of 20 mL of an aqueous 2M sodium carbonate solution and 50 mL of toluene, and the obtained mixture was distilled under reflux for 45 hours. The resultant reaction mixture was cooled to room temperature, and then distilled under a reduced pressure to remove all volatile materials. Water was added to the concentrate, and the thus-deposited solid was collected by filtration and washed with methanol. The thus-obtained crude product was purified by alumina chromatography using a hexane/chloroform (1:1-0:1) mixed solvent as an eluent to give 1.20 g of the target 2-[3,5-bis(2,2':6',2"-terpyridin-4'-yl)phenyl]-4,6-diphenyl-1,3,5-triazine as a white solid (yield: 88%).

$^1$H-NMR (CDCl$_3$): δ7.29-7.34 (m, 4H), 7.52-7.55 (m, 6H), 7.85 (ddd, J=7.8, 7.8, 1.8 Hz, 4H), 8.46 (t, J=1.6 Hz, 1H), 8.66-8.69 (m, 8H), 8.77-8.80 (m, 4H), 8.87 (s, 4H), 9.21 (d, J=1.6 Hz, 2H).

Experiment Example 45

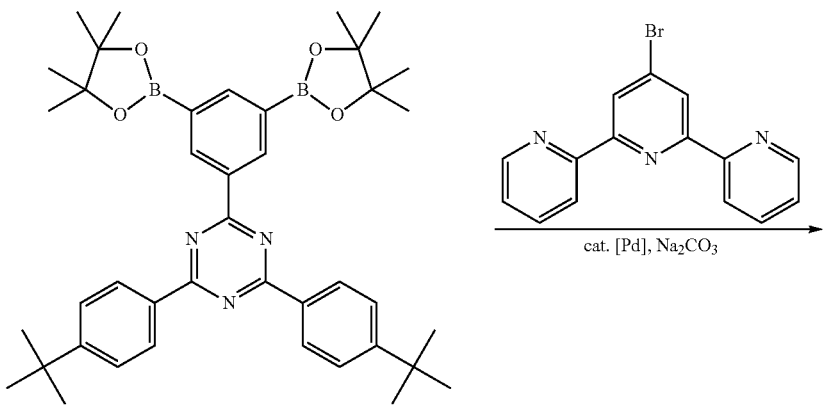

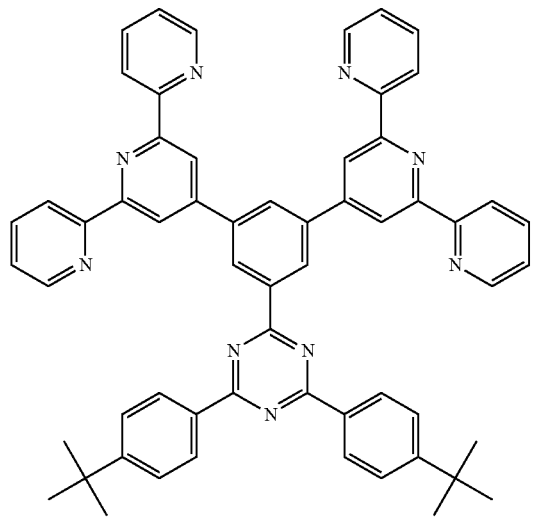

In a stream of argon, 70.0 mg of 4,6-bis(4-tert-butylphenyl)-2-[3,5-bis(4,4,5,5-tetramethyl-1,3,2-dioxaboroan-2-yl)phenyl]-1,3,5-triazine, 78.0 mg of 4'-bromo-2,2':6',2"-terpyridine and 9.6 mg of tetrakis(triphenylphosphine)palladium were suspended in a mixed solvent comprised of 1 mL of an aqueous 2M sodium carbonate solution and 2 mL of toluene, and the obtained mixture was distilled under reflux for 66 hours. The resultant reaction mixture was cooled to room temperature, and then methanol was added to the reaction mixture. The thus-deposited solid was collected by filtration, and the obtained crude product was purified by alumina chromatography using chloroform as an eluent to give 49.0 mg of the target 4,6-bis(4-tert-butylphenyl)-2-[3,5-bis(2,2':6',2"-terpyridin-4'-yl)phenyl]-1,3,5-triazine as a white solid (yield: 53%).

$^1$H-NMR (CDCl$_3$): δ1.30 (s, 18H), 7.26 (ddd, J=7.7, 4.2, 1.1 Hz, 4H), 7.49 (d, J=8.5 Hz, 4H), 7.80 (ddd, J=7.7, 7.7, 1.7 Hz, 4H), 8.37 (t, J=1.7 Hz, 1H), 8.62-8.66 (m, 12H), 8.83 (s, 4H), 9.15 (d, J=1.7 Hz, 2H).

$^{13}$C-NMR (CDCl$_3$): δ31.3 (CH$_3$×6), 35.2 (quart.×2), 119.6 (CH×4), 121.5 (CH×4), 123.9 (CH×4), 125.7 (CH×4), 128.4 (CH×2), 129.1 (CH×4), 130.3 (CH), 133.5 (quart.×2), 136.9 (CH×4), 138.3 (quart.), 140.4 (quart.×2), 149.2 (CH×4), 150.1 (quart.×2), 156.1 (quart.×6), 156.2 (quart.×4), 171.2 (quart.), 171.8 (quart.×2).

Experiment Example 46

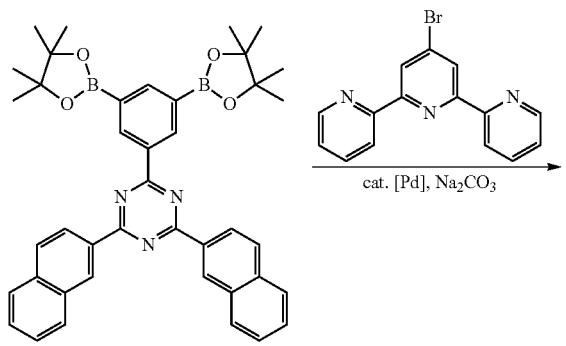

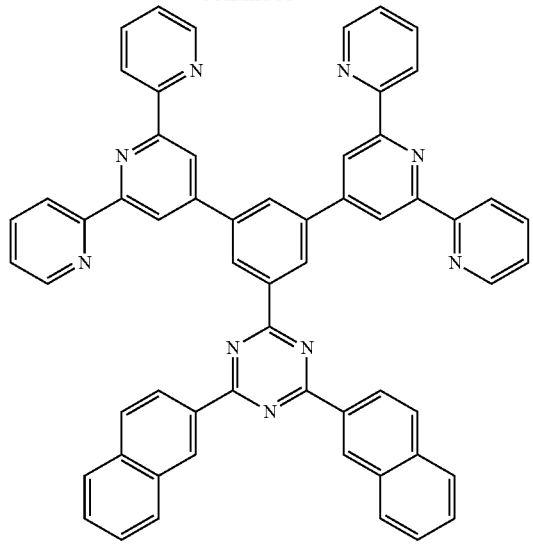

In a stream of argon, 100.0 mg of 2-[3,5-bis(4,4,5,5-tetramethyl-1,3,2-dioxabororan-2-yl)phenyl]-4,6-di(2-naphthyl)-1,3,5-triazine, 133 mg of 4'-bromo-2,2':6',2"-terpyridine and 14.0 mg of tetrakis(triphenylphosphine)palladium were suspended in suspended in a mixed solvent comprised of 1 mL of an aqueous 2M sodium carbonate solution and 4 mL of toluene, and the obtained mixture was distilled under reflux for 59 hours. The resultant reaction mixture was cooled to room temperature, and then distilled under a reduced pressure to remove all volatile materials. Water was added to the concentrate, and the thus-deposited solid was collected by filtration and washed with methanol. The thus-obtained crude product was purified by alumina chromatography using a hexane/chloroform (1:2-0:1) mixed solvent as an eluent to give 91.0 mg of the target 2-[3,5-bis(2,2':6',2"-terpyridin-4'-yl)phenyl]-4,6-di(2-naphthyl)-1,3,5-triazine as a white solid (yield: 69%).

$^1$H-NMR (CDCl$_3$): δ7.31 (ddd, J=7.6, 4.8, 1.2 Hz, 4H), 7.47-7.55 (m, 4H), 7.85 (ddd, J=7.6, 7.6, 1.8 Hz, 4H), 7.85-7.87 (m, 2H), 7.97 (d, J=8.5 Hz, 2H), 8.07 (d, J=7.7 Hz, 2H), 8.48 (t, J=1.7 Hz, 1H), 8.66-8.71 (m, 8H), 8.85 (dd, J=8.5, 1.7 Hz, 2H), 8.92 (s, 4H), 9.30 (d, J=1.7 Hz, 2H), 9.39 (brs, 2H).

Experiment Example 47

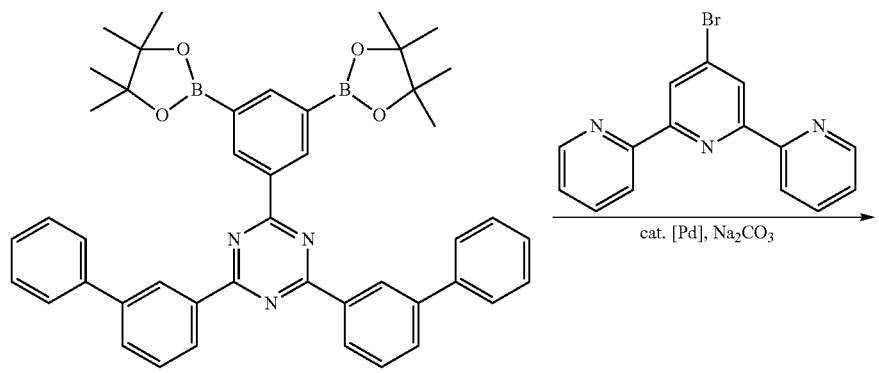

-continued

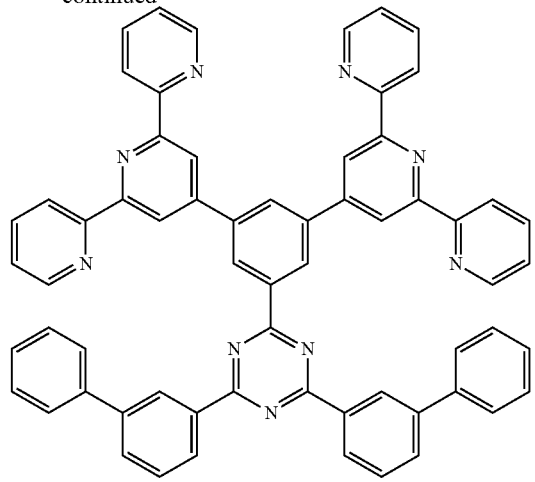

In a stream of argon, 100.0 mg of 4,6-bis(3-biphenylyl)-2-[3,5-bis(4,4,5,5-tetramethyl-1,3,2-dioxabororan-2-yl)phenyl]-1,3,5-triazine, 105 mg of 4'-bromo-2,2':6',2''-terpyridine and 12.9 mg of tetrakis(triphenylphosphine)palladium were suspended in a mixed solvent comprised of 1 mL of an aqueous 2M sodium carbonate solution and 3 mL of toluene, and the obtained mixture was distilled under reflux for 69 hours. The resultant reaction mixture was cooled to room temperature, and then distilled under a reduced pressure to remove all volatile materials. Water was added to the concentrate, and the thus-deposited solid was collected by filtration and washed with methanol. The thus-obtained crude product was purified by alumina chromatography using chloroform as an eluent to give 110 mg of the target 4,6-bis(3-biphenylyl)-2-[3,5-bis(2,2':6',2''-terpyridin-4'-yl)phenyl]-1,3,5-triazine as a white solid (yield: 85%).

$^1$H-NMR (CDCl$_3$): δ7.26-7.32 (m, 10H), 7.61 (t, J=7.7 Hz, 2H), 7.69 (brdd, J=7.9, 1.5 Hz, 4H), 7.79 (brd, J=7.4 Hz, 2H), 7.85 (ddd, J=7.6, 7.6, 1.8 Hz, 4H), 8.48 (t, J=1.7 Hz, 1H), 8.64 (ddd, J=4.7, 1.8, 0.8 Hz, 4H), 8.68 (brdt, J=7.9, 1.0 Hz, 4H), 8.77 (brdt, J=6.5, 1.6 Hz, 2H), 8.90 (s, 4H), 9.03 (t, J=1.6 Hz, 2H), 9.26 (d, J=1.7 Hz, 2H)

$^{13}$C-NMR (CDCl$_3$): δ119.5 (CH×4), 121.4 (CH×4), 123.9 (CH×4), 127.3 (CH×4), 127.5 (CH×2), 127.9 (CH×2), 128.2 (CH×2), 128.6 (CH×2), 128.9 (CH×4), 129.2 (CH×2), 130.3 (CH), 131.4 (CH×2), 136.6 (quart.×2), 136.9 (CH×4), 137.8 (quart.), 140.3 (quart.×2), 140.7 (quart.×2), 141.6 (quart.×2), 149.3 (CH×4), 149.9 (quart.×2), 156.2 (quart.×4), 156.2 (quart.×4), 171.3 (quart.), 171.9 (quart.×2).

Experiment Example 48

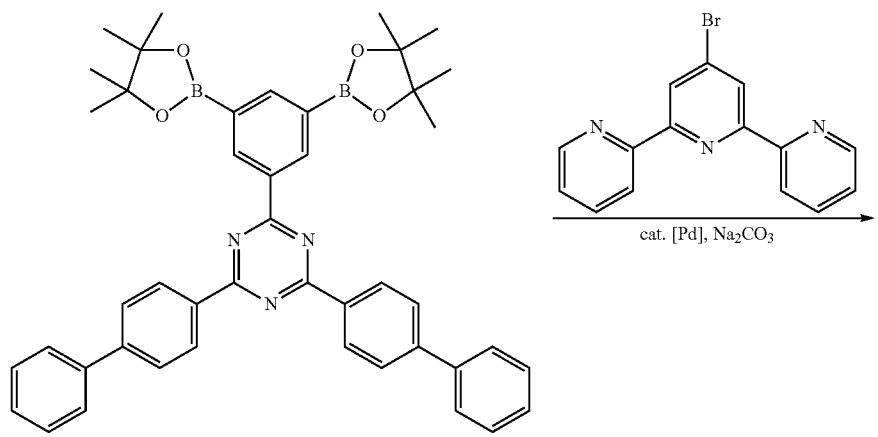

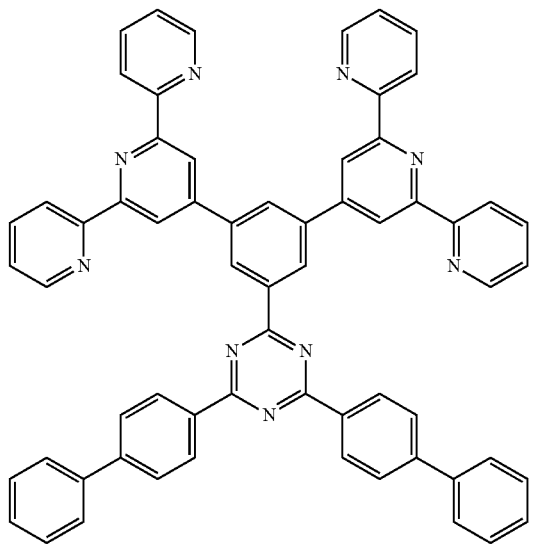

In a stream of argon, 100.0 mg of 4,6-bis(4-biphenylyl)-2-[3,5-bis(4,4,5,5-tetramethyl-1,3,2-dioxaboroaran-2-yl)phenyl]-1,3,5-triazine, 105 mg of 4'-bromo-2,2':6',2''-terpyridine and 12.9 mg of tetrakis(triphenylphosphine)palladium were suspended in a mixed solvent comprised of 1 mL of an aqueous 2M sodium carbonate solution and 3 mL of toluene, and the obtained mixture was distilled under reflux for 69 hours. The resultant reaction mixture was cooled to room temperature, and then distilled under a reduced pressure to remove all volatile materials. Water was added to the concentrate, and the thus-deposited solid was collected by filtration and washed with methanol. The thus-obtained crude product was purified by alumina chromatography using chloroform as an eluent to give 110 mg of the target 4,6-bis(4-biphenylyl)-2-[3,5-bis(2,2':6',2''-terpyridin-4'-yl)phenyl]-1,3,5-triazine as a white solid (yield: 62%).

$^1$H-NMR (CDCl$_3$): δ7.29-7.36 (m, 6H), 7.43 (t, J=7.7 Hz, 4H), 7.65 (brd, J=7.7 Hz, 4H), 7.76 (d, J=8.5 Hz, 4H), 7.85 (ddd, J=7.6, 7.6, 1.8 Hz, 4H), 8.44 (t, J=1.7 Hz, 1H), 8.67-8.71 (m, 8H), 8.85-8.88 (m, 4H), 8.88 (s, 4H), 9.24 (d, J=1.7 Hz, 2H).

Experiment Example 49

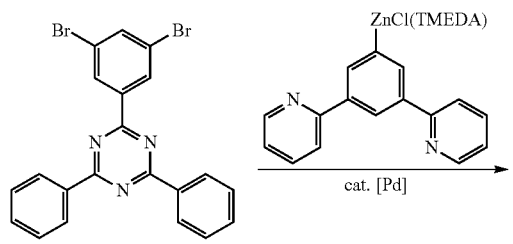

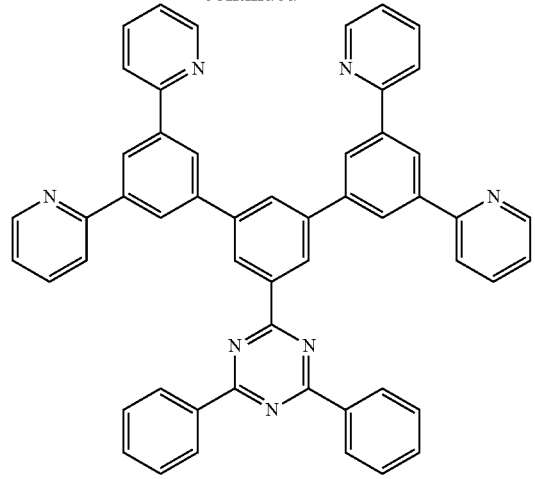

In a stream of argon, 3.34 g of 3,5-di(2-pyridyl)bromobenzene was dissolved in 43 mL of tetrahydrofuran, and then, 7.6 mL of a 1.58M buthyllithium hexane solution was added dropwise at −78° C. to the obtained solution. The obtained mixture was stirred at −78° C. for 15 minutes, and 3.24 g of dichloro(tetramethylethylenediamine)zinc was added to the mixture. The temperature of the obtained mixture was elevated to room temperature, and stirred for 30 minutes. To the obtained mixture, 2.00 g of 2-(3,5-dibromophenyl)-4,6-diphenyl-1,3,5-triazine and 98.9 mg of tetrakis(triphenylphosphine)palladium were added, and the obtained mixture was distilled under reflux for 19 hours. The resultant reaction mixture was cooled to room temperature, and then distilled under a reduced pressure to remove all volatile materials. Methanol was added to the concentrate, and the thus-deposited solid was collected by filtration. The thus-obtained crude product was purified by silica gel chromatography using chloroform as an eluent to give 2.10 g of the target 4,6-diphenyl-2-[3,5,3",5"-tetra(2-pyridyl)-(1,1':3',1"-terphenyl-5'-yl)-1,3,5-triazine as a white solid (yield: 64%).

¹H-NMR (CDCl₃): δ7.32 (dd, J=6.2, 6.1, 4H), 7.55-7.68 (m, 6H), 7.85 (t, J=7.7 Hz, 4H), 8.01 (5, J=8.0 Hz, 4H), 8.33 (s, 1H), 8.51 (s, 4H), 8.76 (s, 2H), 8.80 (d, J=4.8, 4H), 8.85 (d, J=8.0 Hz, 4H), 9.14 (s, 2H).

Experiment Example 50

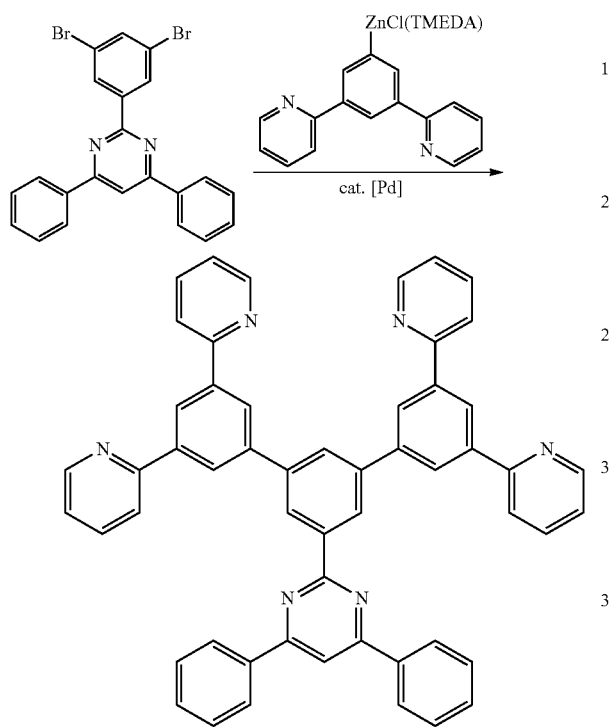

In a stream of argon, 3.34 g of 3,5-di(2-pyridyl)bromobenzene was dissolved in 43 mL of tetrahydrofuran, and then, 7.6 mL of a 1.58M buthyllithium hexane solution was added dropwise at −78° C. to the obtained solution. The obtained mixture was stirred at −78° C. for 15 minutes, and 3.25 g of dichloro(tetramethylethylenediamine)zinc was added to the mixture. The temperature of the obtained mixture was elevated to room temperature, and stirred for 30 minutes. To the obtained mixture, 2.00 g of 2-(3,5-dibromophenyl)-4,6-diphenylpyrimidine and 98.9 mg of tetrakis(triphenylphosphine)palladium were added, and the obtained mixture was distilled under reflux for 17 hours. The resultant reaction mixture was cooled to room temperature, and then distilled under a reduced pressure to remove all volatile materials. Methanol was added to the concentrate, and the thus-deposited solid was collected by filtration. The thus-obtained crude product was purified by silica gel chromatography using chloroform as an eluent to give 2.60 g of the target 4,6-diphenyl-2-[3,5,3",5"-tetra(2-pyridyl)-(1,1':3',1"-terphenyl-5'-yl)-pyrimidine as a white solid (yield: 79%).

¹H-NMR (CDCl₃): δ7.31 (dd, J=6.12, 6.14 Hz, 4H), 7.73-7.64 (m, 6H), 7.84 (t, J=7.7 Hz, 4H), 8.00 (d, J=8.0 Hz, 4H), 8.11 (s, 1H), 8.26 (s, 1H), 8.36 (d, J=9.6 Hz, 4H), 8.50 (s, 4H), 8.75 (s, 2H), 8.79 (d, J=4.0 Hz, 4H), 9.10 (s, 2H).

Experiment Example 51

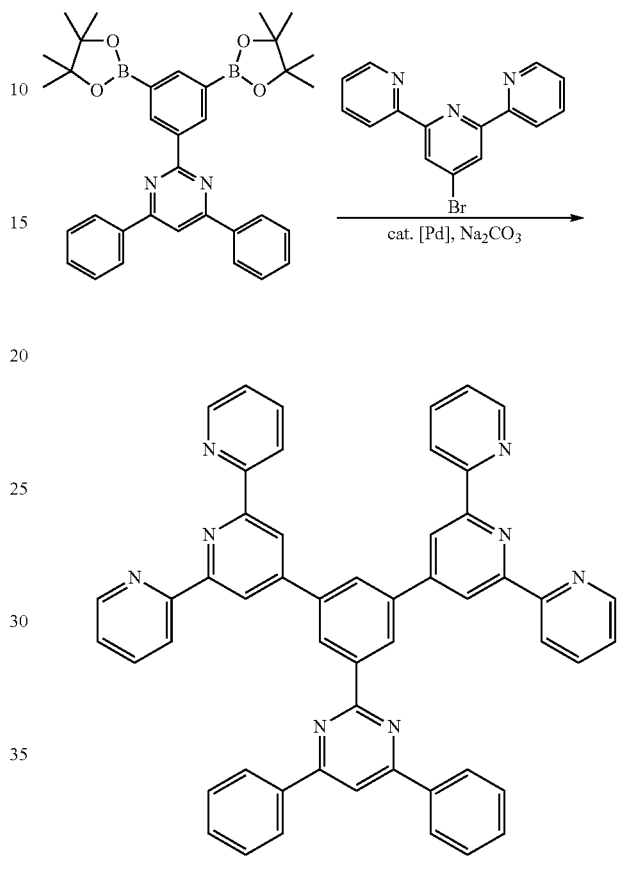

In a stream of argon, 100.0 mg of 2-[3,5-bis(4,4,5,5-tetramethyl-1,3,2-dioxabororan-2-yl)phenyl]-4,6-diphenylpyrimidine, 167 mg of 4'-bromo-2,2':6',2"-terpyridine and 20.6 mg of tetrakis(triphenylphosphine)palladium were suspended in a mixed solvent comprised of 0.8 mL of an aqueous 2M sodium carbonate solution and 5 mL of toluene, and the obtained mixture was distilled under reflux for 86 hours. The resultant reaction mixture was left to stand to room temperature, and then distilled under a reduced pressure to remove all volatile materials. Methanol was added to the concentrate, and the thus-deposited solid was collected by filtration and washed with water and methanol. The thus-obtained crude product was purified by silica gel chromatography using a hexane/chloroform (1:4) mixed solvent as an eluent to give 129 mg of the target 2-[3,5-bis(2,2':6',2"-terpyridin-4'-yl)phenyl]-4,6-diphenylpyrimidine as a white solid (yield: 94%).

¹H-NMR (CDCl₃): δ7.30 (dd, J=7.5, 2.4, 1.2 Hz, 4H), 7.48-7.54 (m, 6H), 7.84 (dd, J=8.0, 7.9, 1.9 Hz, 4H), 8.05 (s, 1H), 8.30 (dd, J=7.9, 1.6 Hz, 4H), 8.35 (t, J=1.7 Hz, 1H), 8.65-8.69 (m, 8H), 8.86 (s, 4H), 9.16 (d, J=1.7 Hz, 2H).

Experiment Example 52

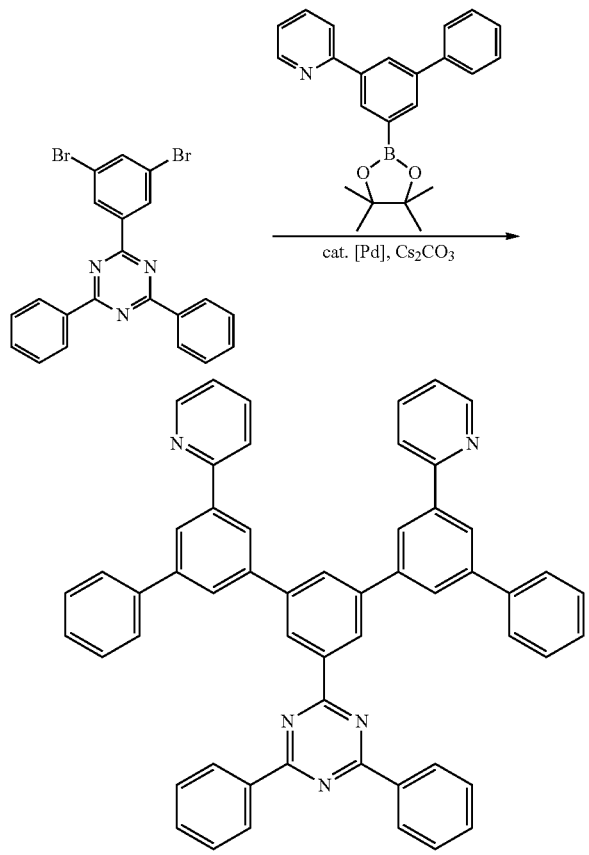

In a stream of argon, 542 mg of 2-[5-(4,4,5,5-tetramethyl-1,3,2-dioxabororan-2-yl)biphenyl-3-yl]pyridine, 329 mg of 2-(3,5-dibromophenyl)-4,6-diphenyl-1,3,5-triazine, 494 mg of cesium carbonate, 6.20 mg of palladium acetate and 26.3 mg of 2-dicyclohexylphosphino-2',4',6'-triisopropylbiphenyl were suspended in 20 mL of tetrahydrofuran, and the obtained mixture was distilled under reflux for 48 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was purified by silica gel chromatography using a hexane/chloroform (1:1) mixed solvent as an eluent to give 200 mg of the target 2,4-diphenyl-6-[5',5''-di(2-pyridyl)-1,1':3',1'':3'',1''':3''',1''''-quinquephenyl-5''-yl]-1,3,5-triazine as a white powder (yield: 38%).

$^1$H-NMR (CDCl$_3$): δ7.22 (ddd, J=7.4, 2.4, 1.1 Hz, 2H), 7.34 (tt, J=7.4, 1.2 Hz, 2H), 7.42-7.54 (m, 10H), 7.72-7.76 (m, 6H), 7.84 (dt, J=8.0, 1.0 Hz, 2H), 7.98 (dt, J=1.7 Hz, 2H), 8.17 (t, J=1.8 Hz, 1H), 8.25 (t, J=1.6 Hz, 2H), 8.30 (t, J=1.6 Hz, 2H), 8.69 (ddd, J=4.8, 0.90, 0.88 Hz, 2H), 8.74 (dd, J=8.1, 1.6 Hz, 4H), 9.02 (d, J=1.7 Hz, 2H).

$^{13}$C-NMR (CDCl$_3$): δ121.0 (CH×2), 122.5 (CH×2), 125.3 (CH×2), 125.4 (CH×2), 127.15 (CH×2), 127.23 (CH×2), 127.6 (CH×4), 127.7 (CH×2), 128.7 (CH×4), 128.9 (CH×4), 129.2 (CH×4), 130.9 (CH×4), 132.6 (CH), 136.2 (quart.×2), 136.9 (CH), 137.7 (quart.), 140.8 (quart.×2), 141.0 (quart.×2), 142.2 (quart.×2), 142.60 (quart.×2), 142.62 (quart.×2), 149.9 (CH), 157.3 (quart.×2), 171.8 (quart.), 171.9 (quart.×2).

Experiment Example 53

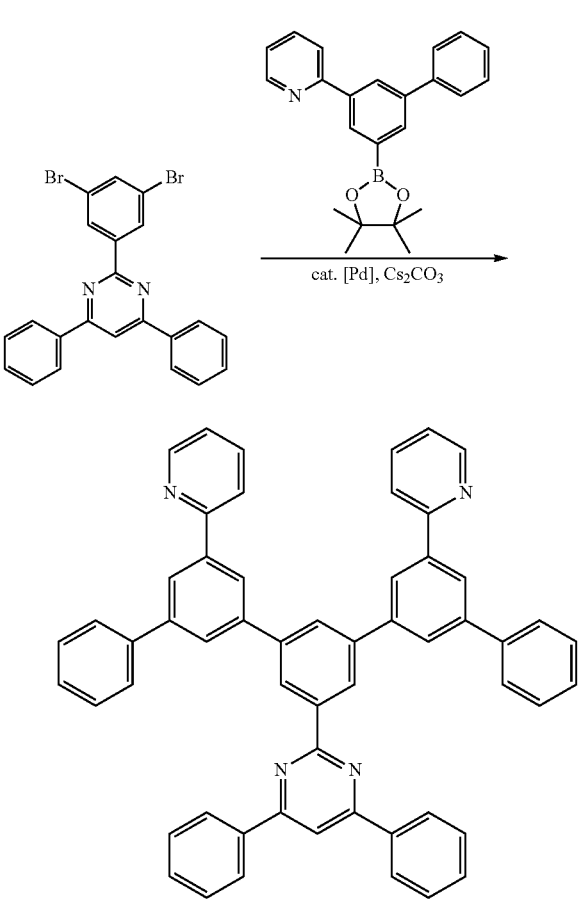

In a stream of argon, 163 g of 2-[5-(4,4,5,5-tetramethyl-1,3,2-dioxabororan-2-yl)biphenyl-3-yl]pyridine, 710 mg of 2-(3,5-dibromophenyl)-4,6-diphenylpyrimidine, 1.49 g of cesium carbonate, 137 mg of palladium acetate and 58.1 mg of 2-dicyclohexylphosphino-2',4',6'-triisopropylbiphenyl were suspended in 30 mL of dioxane, and the obtained mixture was distilled under reflux for 67 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was purified by silica gel chromatography using a methanol/chloroform (1:100-1:50) mixed solvent as an eluent to give 975 mg of the target 4,6-diphenyl-2-[5',5''-di(2-pyridyl)-1,1':3',1'':3'',1''':3''',1''''-quinquephenyl-5''-yl]pyrimidine as a white powder (yield: 83%).

$^1$H-NMR (CDCl$_3$): δ7.30-7.33 (m, 2H), 7.43 (t, J=7.3 Hz, 2H), 7.51-7.59 (m, 10H), 7.83-7.84 (m, 6H), 7.94 (d, J=7.9 Hz, 2H), 8.09-8.12 (m, 3H), 8.19 (bs, 1H), 8.35-8.39 (m, 8H), 8.79 (d, J=4.2 Hz, 2H), 9.09 (bs, 2H).

Experiment Example 54

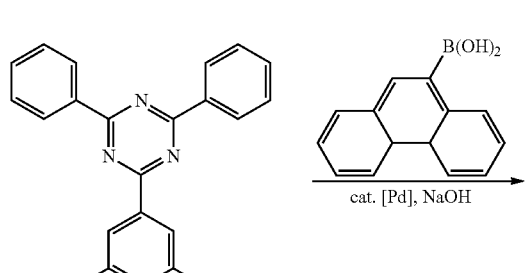

In a stream of argon, 1.37 g (6.16 mmol) of 9-phenanthreneboronic acid, 1.20 g (2.57 mmol) of 2-(3,5-dibromophenyl)-4,6-diphenyl-1,3,5-triazine and 72.1 mg (0.103 mmol) of dichlorobis(triphenylphosphine)palladium were suspended in 75 mL of tetrahydrofuran, and the temperature of the obtained suspension was elevated to 70° C. 4.81 mL (19.3 mmol) of an aqueous 4N NaOH solution was gradually added dropwise to the suspension, and the obtained mixture was distilled under reflux for 5 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was recrystallized from o-xylene to give 1.13 g of the target 2-[3,5-di(9-phenanthryl)phenyl]-4,6-diphenyl-1,3,5-triazine as grayish white solid (yield: 66%).

$^1$H-NMR (CDCl$_3$): δ.7.56 (t, J=7.1 Hz, 4H), 7.61 (t, J=7.3 Hz, 2H), 7.66 (t, J=8.2 Hz, 2H), 7.70 (t, J=8.0 Hz, 2H), 7.75 (t, J=8.4 Hz, 2H), 7.76 (t, J=8.3 Hz, 2H), 7.97 (s, 2H), 8.02 (d, J=8.0 Hz, 2H), 8.03 (s, 1H), 8.18 (d, J=8.1 Hz, 2H), 8.79 (d, J=8.3 Hz, 4H), 8.81 (d, J=8.4 Hz, 2H), 8.87 (d, J=8.4 Hz, 2H), 9.09 (s, 2H).

The melting point and Tg of the obtained compound are shown in Table 1, below.

Experiment Example 55

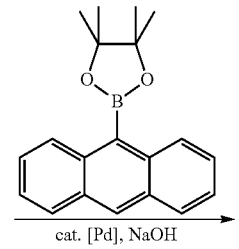

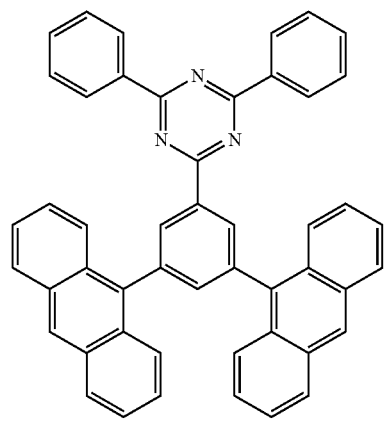

In a stream of argon, 1.00 g (3.28 mmol) of 9-(4,4,5,5-tetramethyl-1,3,2-dioxabororan-2-yl)anthracene, 0.64 g (1.37 mmol) of 2-(3,5-dibromophenyl)-4,6-diphenyl-1,3,5-triazine, 15.38 mg (0.069 mmol) of palladium acetate, and 0.21 mL of a toluene solution containing 0.21 mmol of tri-tert-butylphosphine were suspended in 65 mL of tetrahydrofuran, and the temperature of the obtained suspension was elevated to 70° C. 2.57 mL (10.3 mmol) of an aqueous 4N NaOH solution was gradually added dropwise to the suspension, and the obtained mixture was distilled under reflux for 3 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was purified by silica gel chromatography using a hexane/chloroform (5:1-2:1) mixed solvent as an eluent to give 0.39 g of the target 2-[3,5-di(9-anthryl)phenyl]-4,6-diphenyl-1,3,5-triazine as white solid (yield: 43%).

$^1$H-NMR (CDCl$_3$): δ.7.49-7.57 (m, 14H), 7.82 (s, 1H), 8.04 (d, J=8.7 Hz, 4H), 8.13 (d, J=8.2 Hz, 4H), 8.61 (s, 2H), 8.72 (d, J=8.7 Hz, 4H), 9.08 (s, 2H).

The melting point and Tg of the obtained compound are shown in Table 1, below.

Experiment Example 56

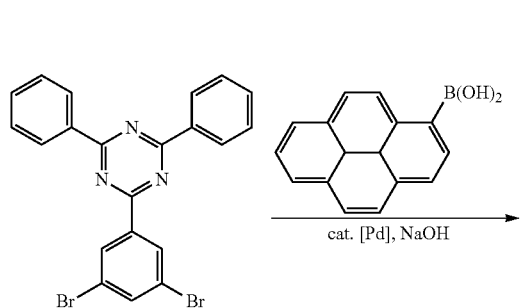

In a stream of argon, 1.26 g (5.13 mmol) of 1-pyreneboronic acid, 1.00 g (2.14 mmol) of 2-(3,5-dibromophenyl)-4,6-diphenyl-1,3,5-triazine and 60.1 mg (0.081 mmol) of dichlorobis(triphenylphosphine)palladium were suspended in 75 mL of tetrahydrofuran, and the temperature of the obtained suspension was elevated to 70° C. 4.01 mL (16.1 mmol) of an aqueous 4N NaOH solution was gradually added dropwise to the suspension, and the obtained mixture was distilled under reflux for 3 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was recrystallized from o-xylene to give 1.23 g of the target 2-[3,5-di(1-pyrenyl)-phenyl]-4,6-diphenyl-1,3,5-triazine as grayish white solid (yield: 81%).

$^{1}$H-NMR (CDCl$_3$): δ.7.55 (t, J=7.0 Hz, 4H), 7.60 (t, J=7.1 Hz, 2H), 8.08 (t, J=7.6, 2H), 8.11-8.21 (m, 7H), 8.24 (d, J=7.5 Hz, 2H), 8.27 (d, J=8.7 Hz, 2H), 8.31 (d, J=8.1 Hz, 2H), 8.38 (d, J=7.8 Hz, 2H), 8.48 (d, J=9.3 Hz, 2H), 8.80 (d, J=7.2 Hz, 4H), 9.20 (s, 2H).

The melting point and Tg of the obtained compound are shown in Table 1, below.

Experiment Example 57

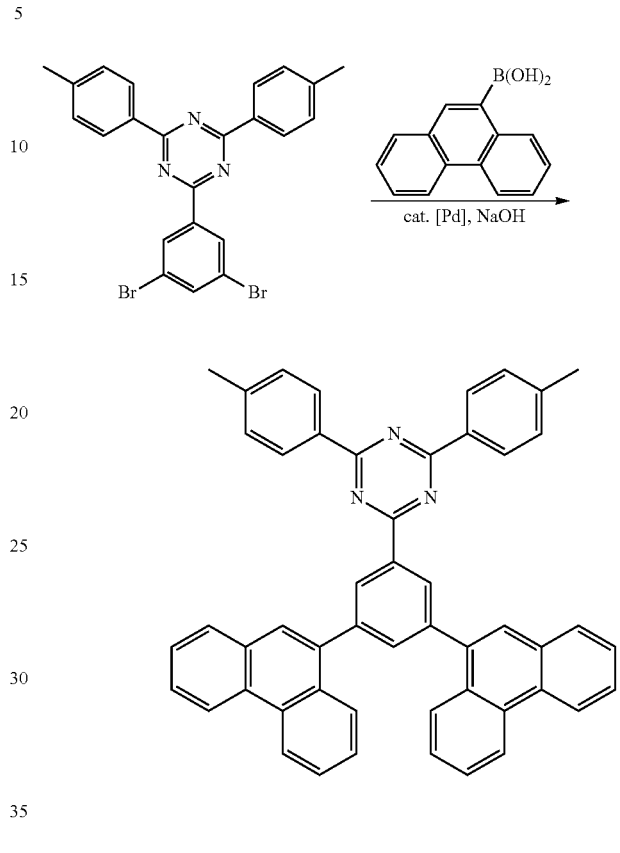

In a stream of argon, 1.29 g (5.81 mmol) of 9-phenanthreneboronic acid, 1.20 g (2.42 mmol) of 2-(3,5-dibromophenyl)-4,6-di-p-tolyl-1,3,5-triazine and 67.9 mg (0.097 mmol) of dichlorobis(triphenylphosphine)palladium were suspended in 108 mL of tetrahydrofuran, and the temperature of the obtained suspension was elevated to 70° C. 4.53 mL (18.2 mmol) of an aqueous 4N NaOH solution was gradually added dropwise to the suspension, and the obtained mixture was distilled under reflux for 2 hours. Further, 0.11 g (0.50 mmol) of 9-phenanthreneboronic acid was added, and the obtained mixture was distilled under reflux for 2 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was recrystallized from o-xylene to give 0.74 g of the target 2-[3,5-di(9-phenanthryl)-phenyl]-4,6-di-p-tolyl-1,3,5-triazine as grayish white solid (yield: 44%).

$^{1}$H-NMR (CDCl$_3$): δ.2.47 (s, 6H), 7.34 (d, J=8.0 Hz, 4H), 7.65 (t, J=7.6 Hz, 2H), 7.69 (t, J=7.4 Hz, 2H), 7.75 (t, J=6.9 Hz, 4H), 7.97 (s, 2H), 8.01 (s, 1H), 8.02 (d, J=7.4 Hz, 2H), 8.18 (d, J=8.1 Hz, 2H), 8.66 (d, J=8.2 Hz, 4H), 8.81 (d, J=8.3 Hz, 2H), 8.87 (d, J=8.2 Hz, 2H), 9.07 (s, 2H).

The melting point and Tg of the obtained compound are shown in Table 1, below.

Experiment Example 58

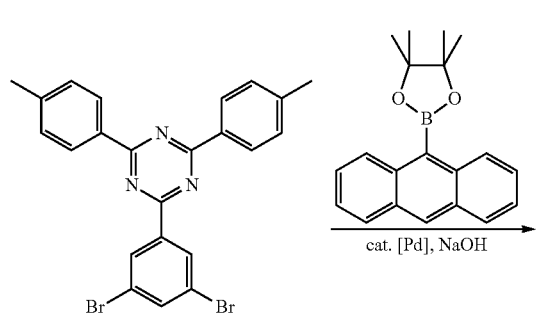

In a stream of argon, 1.35 g (4.44 mmol) of 9-(4,4,5,5-tetramethyl-1,3,2-dioxabororan-2-yl)anthracene, 1.00 g (2.02 mmol) of 2-(3,5-dibromophenyl)-4,6-di-p-tolyl-1,3,5-triazine and 56.7 mg (0.081 mmol) of dichlorobis-(triphenylphosphine)palladium were suspended in 100 mL of tetrahydrofuran, and the temperature of the obtained suspension was elevated to 70° C. 3.78 mL (15.1 mmol) of an aqueous 4N NaOH solution was gradually added dropwise to the suspension, and the obtained mixture was distilled under reflux for 23.5 hours. Then, 0.20 g (0.66 mmol) of 9-(4,4,5,5-tetramethyl-1,3,2-dioxabororan-2-yl)anthracene and 14 mg (0.02 mmol) of dichlorobis(triphenylphosphine)palladium were added, followed by distillation under reflux for 4 hours. Further, 0.20 g (0.66 mmol) of 9-(4,4,5,5-tetramethyl-1,3,2-dioxabororan-2-yl)anthracene and 14 mg (0.02 mmol) of dichlorobis(triphenylphosphine)palladium were added, followed by distillation under reflux for 1 hour. The resultant reaction mixture was left to stand to room temperature, and then distilled under a reduced pressure to remove all volatile materials. Methanol was added to the concentrate, and the thus-deposited solid was collected by filtration. The thus-obtained crude product was recrystallized from o-xylene to give 0.55 g of the target 2-[3,5-di(9-anthryl)phenyl]-4,6-di-p-tolyl-1,3,5-triazine as grayish white solid (yield: 39%).

$^1$H-NMR (CDCl$_3$): δ.2.44 (s, 6H), 7.29 (d, J=8.6 Hz, 4H), 7.48-7.56 (m, 8H), 7.80 (s, 1H), 8.04 (d, J=8.0 Hz, 4H), 8.13 (d, J=8.0 Hz, 4H), 8.60 (d, J=8.2 Hz, 4H), 8.60 (s, 2H), 9.07 (s, 2H).

The melting point and Tg of the obtained compound are shown in Table 1, below.

Experiment Example 59

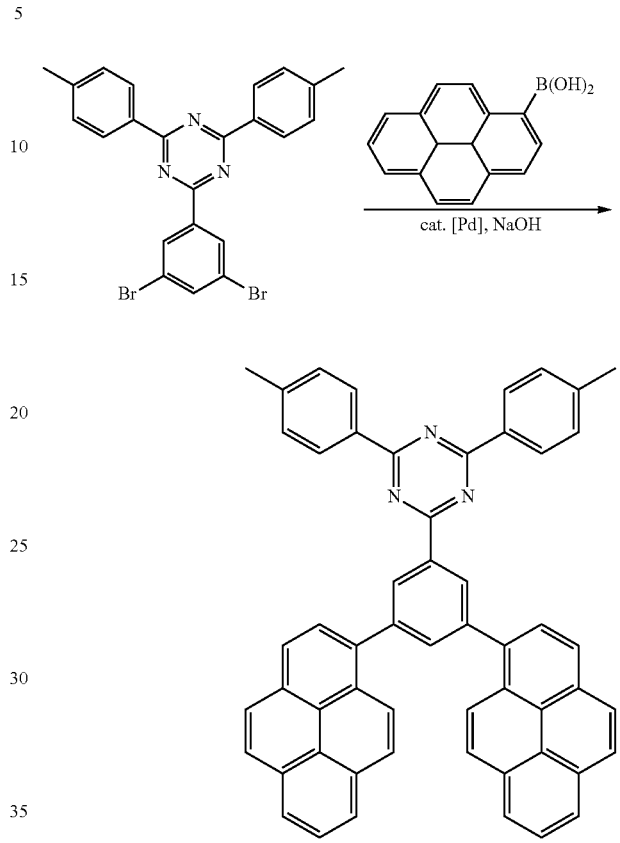

In a stream of argon, 1.20 g (4.87 mmol) of 1-pyreneboronic acid, 1.50 g (3.03 mmol) of 2-(3,5-dibromophenyl)-4,6-di-p-tolyl-1,3,5-triazine and 57 mg (0.081 mmol) of dichlorobis-(triphenylphosphine)palladium were suspended in 135 mL of tetrahydrofuran, and the temperature of the obtained suspension was elevated to 70° C. 3.81 mL (15.2 mmol) of an aqueous 4N NaOH solution was gradually added dropwise to the suspension, and the obtained mixture was distilled under reflux for 2 hours. Then, 29 mg (0.041 mmol) of dichlorobis(triphenylphosphine)palladium was added, followed by distillation under reflux for 2 hours. Further, 0.20 g (0.81 mmol) of 1-pyreneboronic acid was added, followed by distillation under reflux for 2 hours. The resultant reaction mixture was left to stand to room temperature, and then distilled under a reduced pressure to remove all volatile materials. Methanol was added to the concentrate, and the thus-deposited solid was collected by filtration. The thus-obtained crude product was recrystallized from o-xylene. The recrystallization by o-xylene was repeated three times in total to give 1.14 g of the target 2-[3,5-di(1-pyrenyl)phenyl]-4,6-di-p-tolyl-1,3,5-triazine as grayish white solid (yield: 51%).

$^1$H-NMR (CDCl$_3$): δ.2.46 (s, 6H), 7.33 (d, J=8.0 Hz, 4H), 8.08 (t, J=7.6 Hz, 2H), 8.16 (d, J=9.3 Hz, 2H), 8.19 (d, J=3.7 Hz, 4H), 8.21 (s, 1H), 8.24 (d, J=7.4 Hz, 2H), 8.27 (d, J=9.0 Hz, 2H), 8.29 (d, J=8.0 Hz, 2H), 8.37 (d, J=7.9 Hz, 2H), 8.48 (d, J=9.3 Hz, 2H), 8.67 (d, J=8.2 Hz, 4H), 9.18 (s, 2H).

The melting point and Tg of the obtained compound are shown in Table 1, below.

Experiment Example 60

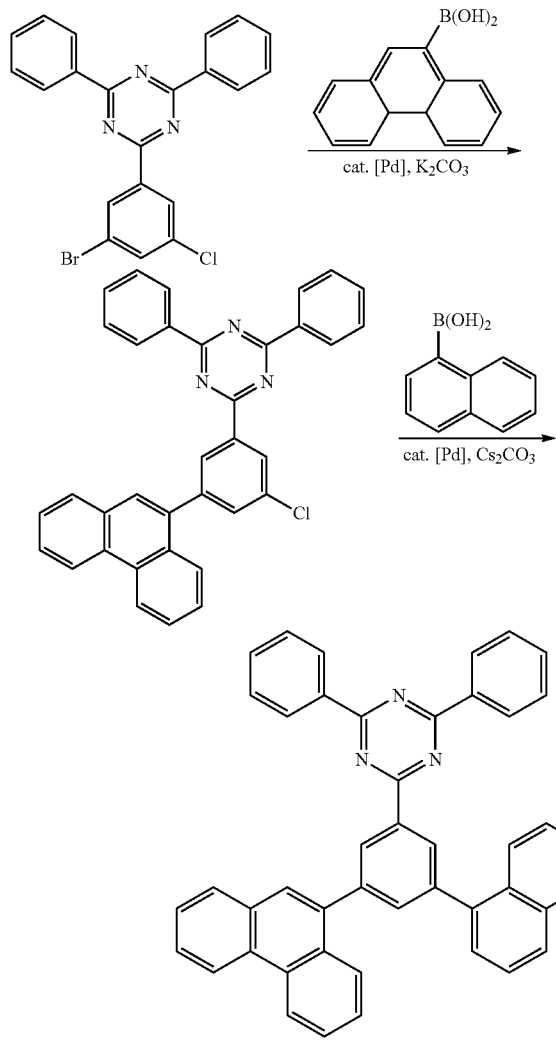

In a stream of argon, 0.52 g (2.36 mmol) of 9-phenantreneboronic acid, 0.91 g (2.15 mmol) of 2-(3-bromo-5-chlorophenyl)-4,6-diphenyl-1,3,5-triazine and 24.8 mg (0.022 mmol) of tetrakis(triphenylphosphine)palladium were suspended in a mixed solvent comprised of 80 mL of toluene and 10 mL of ethanol, and the temperature of the obtained suspension was elevated to 60° C. 6.45 mL (6.45 mmol) of an aqueous 1M $K_2CO_3$ solution was gradually added dropwise to the suspension, and the obtained mixture was distilled under reflux for 18 hours. The resultant reaction mixture was cooled to room temperature, and then distilled under a reduced pressure to remove all volatile materials. Methanol was added to the concentrate, and the thus-deposited solid was collected by filtration. The thus-obtained crude product was dissolved in chloroform and the obtained solution was filtered by celite. The filtrate was distilled to remove all volatile materials to give 1.02 g of an intermediate 2-[3-chloro-5-(9-phenanthryl)phenyl]-4,6-diphenyl-1,3,5-triazine as grayish white solid (yield: 91%).

Then in a stream of argon, 0.5 g (0.96 mmol) of the obtained 2-[3-chloro-5-(9-phenanthryl)phenyl]-4,6-diphenyl-1,3,5-triazine, 038 g (1.73 mmol) of 1-naphthaleneboronic acid, 12.9 mg (0.058 mmol) of palladium acetate and 1.13 g (3.46 mmol) of cesium carbonate were suspended in 50 mL of tetrahydrofuran, and the temperature of the obtained suspension was elevated to 70° C. and distilled under reflux for 40 hours. The resultant reaction mixture was cooled to room temperature, and then distilled under a reduced pressure to remove all volatile materials. Methanol was added to the concentrate, and the thus-deposited solid was collected by filtration. The thus-obtained crude product was purified by column chromatography to give 0.56 g of the target 2-[3-(1-naphthyl)-5-(9-phenanthryl)phenyl]-4,6-diphenyl-1,3,5-triazine as grayish white solid (yield: 95%).

$^1$H-NMR (CDCl$_3$): δ.7.53-7.77 (m, 15H), 7.96 (d, J=9.0 Hz, 2H), 8.00 (t, J=7.7 Hz, 2H), 8.15 (d, J=4.3 Hz, 1H), 8.16 (d, J=4.8 Hz, 1H), 8.78 (d, J=7.0 Hz, 4H), 8.81 (d, 8.5 Hz, 1H), 8.87 (d, J=8.2 Hz, 1H), 9.05 (d, 7.7 Hz, 2H).

Experiment Example 61

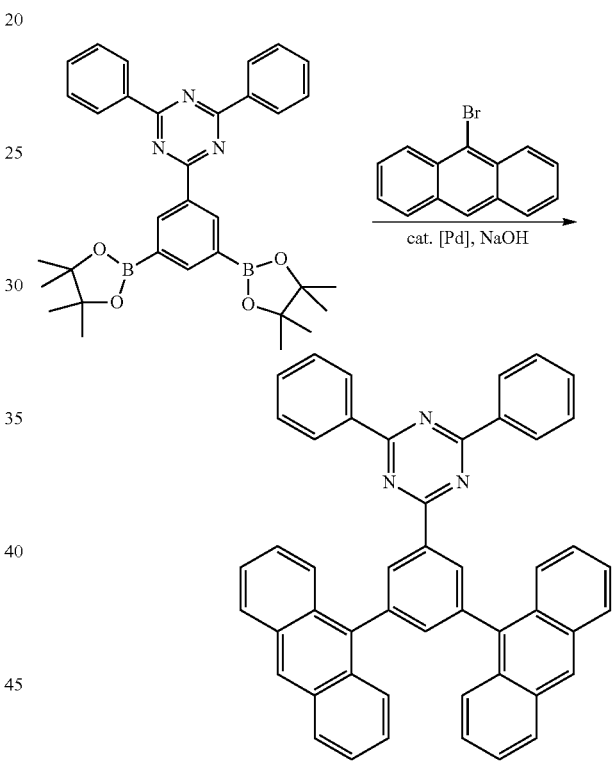

In a stream of argon, 0.62 g (2.13 mmol) of 9-bromoanthracene, 0.50 g (0.89 mmol) of 2-(3,5-bis(4,4,5,5-tetramethyl)-1,3,2-dioxabororan-2-yl)phenyl]-4,6-diphenyl-1,3,5-triazine and 18.7 mg (0.027 mmol) of dichlorobis-(triphenylphosphine)palladium were suspended in 40 mL of tetrahydrofuran, and the temperature of the obtained suspension was elevated to 70° C. 1.34 mL (5.34 mmol) of an aqueous 4N NaOH solution was gradually added dropwise to the suspension, and the obtained mixture was distilled under reflux for 3 hours. The resultant reaction mixture was cooled to room temperature, and then distilled under a reduced pressure to remove all volatile materials. Methanol was added to the concentrate, and the thus-deposited solid was collected by filtration. The thus-obtained crude product was purified by silica gel column chromatography using a hexane/chloroform (5:1-2:1) mixed solvent as an eluent to give 0.32 g of the target 2-[3,5-di(9-anthryl)phenyl]-4,6-diphenyl-1,3,5-triazine as white solid (yield: 54%).

$^1$H-NMR (CDCl$_3$): δ.7.49-7.57 (m, 14H), 7.82 (s, 1H), 8.04 (d, J=8.7 Hz, 4H), 8.13 (d, J=8.2 Hz, 4H), 8.61 (s, 2H), 8.72 (d, J=8.7 Hz, 4H), 9.08 (s, 2H).

Test Example 1

A glass substrate with a transparent indium-tin oxide (ITO) electrode was prepared, which had a stripe pattern comprised of ITO film with a 2 mm width. The substrate was washed with isopropyl alcohol and then surface-treated by irradiation of ultraviolet rays. Using the surface-treated substrate, an organic EL device with an emitting area of 4 mm$^2$ having a multilayer structure as illustrated in FIG. 1 was manufactured as follows.

Each layer was formed by vacuum deposition. The glass substrate was placed in a vacuum deposition chamber, and the inner pressure was reduced to 1.0×10$^{-4}$ Pa.

As illustrated in FIG. 1, organic compound layers, i.e., a hole injection layer 2, a hole transport layer 3, an emitting layer 4 and an electron transport layer 5 were formed in this order on the above-mentioned glass substrate 1. Further, a cathode layer 6 was formed.

The hole injection layer 2 was formed by vacuum-depositing phtalocyanine copper(II), previously purified by sublimation, into a thickness of 25 nm. The hole transport layer 3 was formed by vacuum-depositing N,N'-di(naphthylen-1-yl)-N,N'-diphenylbenzidine (NPD) into a thickness of 45 nm.

The emitting layer 4 was formed by vacuum-depositing a mixture of 97 mass % of 4,4'-bis(2,2-diphenylethen-1-yl) diphenyl (DPVBi) and 3 mass % of 4,4'-bis[4-(di-p-tolylamino)phenylethen-1-yl]biphenyl (DPAVBi) into a thickness of 40 nm. The electron transport layer 5 was formed by vacuum-depositing 2-[4,4"-di(2-pyridyl)-1,1':3',1"-terphenyl-5'-yl]-4,6-diphenylpyrimidine, synthesized in Experiment Example 1 according to the present invention, into a thickness of 20 nm.

The vacuum deposition of each organic material was conducted by subjecting each organic material to electric resistance heating to form a thin film at a deposition rate of 0.3 nm/sec to 0.5 nm/sec.

Then, a metal mask was arranged so as to be orthogonal to the ITO stripe, and a cathode layer 6 was vacuum-deposited. The vacuum deposition of the cathode layer 6 was conducted so as to have a double layer structure comprising a lithium fluoride layer with a thickness of 0.5 nm and an aluminum layer with a thickness of 100 nm. The measurement of thickness of each organic material thin film layer was conducted by stylus profilometer ("DEKTAK").

Finally the thus-obtained assembly of multi-layers was encapsulated with a glass cap and ultraviolet ray-curable epoxy resin (available from Nagase Chemtex Corporation). The encapsulation was conducted in a nitrogen atmosphere having an oxygen-and-moisture content of below 1 ppm within a glove box.

Luminous properties of the thus-manufactured blue EL device were evaluated by applying a direct current and using a luminance meter "BM-9" available from Topcon Corporation. The luminous properties, i.e., voltage (V), luminance (cd/m$^2$), current efficiency (cd/A) and power efficiency (lm/W) were measured at a current density of 20 mA/cm$^2$.

The luminous properties of the manufactured blue fluorescent device were as follows. Voltage 5.8V, luminance 2,160 cd/m$^2$, current efficiency 10.8 cd/A, power efficiency 5.9 lm/W. Luminance half-life of the device was 171 hours.

Test Example 2

By the same procedures as described in Test Example 1, an organic EL device was manufactured except that an emitting layer 4 was formed by vacuum-depositing tris(8-quinolinolato)aluminum (III) (Alq) into a thickness of 40 nm instead of the emitting layer formed from DPVBi/DPAVBi mixture in Test Example 1.

The thus-manufactured green fluorescent device exhibited a voltage of 5.1 V, a luminance of 958 cd/m$^2$, a current efficiency of 4.8 cd/A, and a power efficiency of 2.9 lm/W. Luminance half-life of the device was 1,618 hours.

Test Example 3

By the same procedures as described in Test Example 1, an organic EL device was manufactured except the hole injection layer 2, the hole transport layer 3, the emitting layer 4 and the electron transport layer 5 were formed as follows.

The hole injection layer 2 was formed by vacuum-depositing phtalocyanine copper (II), previously purified by sublimation, into a thickness of 10 nm. The hole transport layer 3 was formed by vacuum-depositing N,N'-di(naphthylen-1-yl)-N,N'-diphenylbenzidine (NPD) into a thickness of 30 nm. The emitting layer 4 was formed by co-vacuum-depositing into a thickness of 30 nm a host material of 4,4'-di(carbazol-9-yl)biphenyl (CBP) and a dopant of tris(2-phenylpyridine) iridium (III) (Ir(ppy)$_3$) at a dope concentration of 6%.

The electron transport layer 5 was formed by vacuum-depositing 2-[4,4"-di(2-pyridyl)-1,1':3',1"-terphenyl-5'-yl]-4,6-diphenylpyrimidine, synthesized in Experiment Example 1 according to the present invention, into a thickness of 50 nm. All other conditions and procedures remained the same.

The thus-manufactured green phosphorescent device exhibited a voltage of 7.5 V, a luminance of 6,610 cd/m$^2$, a current efficiency of 33.5 cd/A, and a power efficiency of 13.9 lm/W. Luminance half-life of the device was 230 hours.

Test Example 4

By the same procedures as described in Test Example 1, an organic EL device was manufactured except the electron transport layer 5 was formed by vacuum-depositing 2-[3,3"-di(2-pyridyl)-1,1':3',1"-terphenyl-5'-yl]-4,6-diphenylpyrimidine into a thickness of 20 nm instead of the electron transport layer formed in Test Example 1.

The thus-manufactured blue fluorescent device exhibited a voltage of 6.3 V, a luminance of 2,110 cd/m$^2$, a current efficiency of 10.6 cd/A, and a power efficiency of 5.3 lm/W. Luminance half-life of the device was 165 hours.

Comparative Test Example 1

By the same procedures as described in Test Example 1, an organic EL device was manufactured except that an electron transport layer 5 was formed by vacuum-depositing Alq into a thickness of 20 nm instead of the electron transport layer 5 formed from the cyclic azine derivative of the present invention.

The thus-manufactured blue fluorescent device exhibited a voltage of 7.1 V, a luminance of 1,883 cd/m$^2$, a current efficiency of 9.4 cd/A, and a power efficiency of 4.2 lm/W. Luminance half-life of the device was 163 hours.

Comparative Test Example 2

By the same procedures as described in Test Example 2, an organic EL device was manufactured except that an electron transport layer 5 was formed by vacuum-depositing Alq into a thickness of 20 nm instead of the electron transport layer 5 formed from the cyclic azine derivative of the present invention.

The thus-manufactured green fluorescent device exhibited a voltage of 5.6 V, a luminance of 957 cd/m$^2$, a current efficiency of 4.8 cd/A, and a power efficiency of 2.6 lm/W. Luminance half-life of the device was 1,318 hours.

Comparative Test Example 3

By the same procedures as described in Test Example 3, an organic EL device was manufactured except that an electron transport layer 5 was formed by vacuum-depositing Alq into a thickness of 50 nm instead of the electron transport layer 5 formed from the cyclic azine derivative of the present invention.

The thus-manufactured green phosphorescent device exhibited a voltage of 7.7 V, a luminance of 3,850 cd/m$^2$, a current efficiency of 16.9 cd/A, and a power efficiency of 6.7 lm/W. Luminance half-life of the device was 271 hours.

Comparative Test Example 4

By the same procedures as described in Test Example 3, an organic EL device was manufactured except that an electron transport layer 5 was formed by vacuum-depositing BAlq (bis(2-methyl-8-quinolinolato)-4-phenylphenolat-aluminum) into a thickness of 5 nm and Alq into a thickness of 45 nm in this order instead of the electron transport layer 5 formed from the cyclic azine derivative of the present invention.

The thus-manufactured green phosphorescent device exhibited a voltage of 9.3 V, a luminance of 6,170 cd/m$^2$, a current efficiency of 30.9 cd/A, and a power efficiency of 10.4 lm/W. Luminance half-life of the device was 202 hours.

Test Example 5

By the same procedures as described in Test Example 1, an organic EL device was manufactured except the electron transport layer 5 was formed by vacuum-depositing 2-[5-(9-phenanthryl)-4'-(2-pyridyl)biphenyl-3-yl]-4,6-diphenyl-1,3,5-triazine, synthesized in Experiment Example 15 according to the present invention, into a thickness of 20 nm instead of the electron transport layer formed in Test Example 1.

The thus-manufactured blue fluorescent device exhibited a voltage of 5.3 V, and a current efficiency of 10.5 cd/A. Luminance half-life of the device was 155 hours.

Test Example 6

By the same procedures as described in Test Example 5, an organic EL device was manufactured except the emitting layer 4 was formed by vacuum-depositing Alq$_3$ into a thickness of 40 nm instead of the emitting layer 4 in Test Example 5.

The thus-manufactured EL device exhibited a voltage of 5.2 V and a current efficiency of 2.5 cd/A at a current density of 20 mA/cm$^2$. Luminance half-life of the device was 2015 hours.

Test Example 7

By the same procedures as described in Test Example 5, an organic EL device was manufactured except the electron transport layer 5 was formed by vacuum-depositing Alq$_3$ into a thickness of 20 nm instead of the electron transport layer 5 in Test Example 5.

The thus-manufactured EL device exhibited a voltage of 6.9 V and a current efficiency of 6.1 cd/A at a current density of 20 mA/cm$^2$. Luminance half-life of the device was 53 hours.

Test Example 8

By the same procedures as described in Test Example 6, an organic EL device was manufactured except the electron transport layer 5 was formed by vacuum-depositing Alq$_3$ into a thickness of 20 nm instead of the electron transport layer 5 in Test Example 6.

The thus-manufactured EL device exhibited a voltage of 5.4 V and a current efficiency of 4.3 cd/A at a current density of 20 mA/cm$^2$. Luminance half-life of the device was 1,785 hours.

Test Example 9

By the same procedures as described in Test Example 5, an organic EL device was manufactured except the electron transport layer 5 was formed by vacuum-depositing 4,6-diphenyl-2-[5-(1-naphthyl)-4'-(2-pyridyl)biphenyl-3-yl]-1,3,5-triazine into a thickness of 20 nm instead of the electron transport layer 5 in Test Example 5.

The thus-manufactured EL device exhibited a voltage of 6.0 V and a current efficiency of 11.1 cd/A at a current density of 20 mA/cm$^2$. Luminance half-life of the device was 113 hours.

Test Example 10

By the same procedures as described in Test Example 5, an organic EL device was manufactured except the electron transport layer 5 was formed by vacuum-depositing 2-[5-(9-phenanthryl)-3'-(3-pyridyl)biphenyl-3-yl]-1,3,5-triazine into a thickness of 20 nm instead of the electron transport layer 5 in Test Example 5.

The thus-manufactured EL device exhibited a voltage of 6.1 V and a current efficiency of 11.5 cd/A at a current density of 20 mA/cm$^2$. Luminance half-life of the device was 117 hours.

Test Example 11

By the same procedures as described in Test Example 5, an organic EL device was manufactured except the electron transport layer 5 was formed by vacuum-depositing 2-[3-(2,2'-bipyridin-6-yl)-5-(9-phenanthryl)phenyl]-4,6-diphenyl-1,3,5-triazine into a thickness of 20 nm instead of the electron transport layer 5 in Test Example 5.

The thus-manufactured EL device exhibited a voltage of 5.3 V and a current efficiency of 8.0 cd/A at a current density of 20 mA/cm$^2$.

Test Example 12

By the same procedures as described in Test Example 5, an organic EL device was manufactured except the electron transport layer 5 was formed by vacuum-depositing 4,6-diphenyl-2-[5-(9-phenanthryl)-3'-(2-pyridyl)biphenyl-3-yl]-1,3,5-triazine into a thickness of 20 nm instead of the electron transport layer 5 in Test Example 5.

The thus-manufactured EL device exhibited a voltage of 6.6 V and a current efficiency of 9.7 cd/A at a current density of 20 mA/cm$^2$.

Test Example 13

By the same procedures as described in Test Example 5, an organic EL device was manufactured except the hole injection layer 2, the hole transport layer 3, the emitting layer 4 and the electron transport layer 5 were formed as follows.

The hole injection layer 2 was formed by vacuum-depositing phtalocyanine copper (II) into a thickness of 10 nm. The hole transport layer 3 was formed by vacuum-depositing N,N'-bis(1-naphthyl)-N,N'-diphenyl-4,4'-biphenyl (NPD) into a thickness of 30 nm. The emitting layer 4 was formed by vacuum-depositing into a thickness of 30 nm a mixture of 4,4'-bis(9H-carbazol-9-yl)biphenyl (CBP) and tris(2-phenylpyridinato) iridium (III) (Ir(ppy)$_3$) at a ratio of 94:6 by weight.

The electron transport layer 5 was formed by vacuum-depositing bis(2-methyl-8-quinolinolato)-4-phenylphenolato-aluminum (BAlq) into a thickness of 5 nm and 2-[5-(9,9-dimethylfluoren-2-yl)-4'-(2-pyridyl)biphenyl-3-yl]-4,6-diphenyl-1,3,5-triazine into a thickness of 45 nm in this order. All other conditions and procedures remained the same as in Test Example 5.

The thus-manufactured EL device exhibited a voltage of 7.7 V and a current efficiency of 29.2 cd/A at a current density of 20 mA/cm$^2$.

Test Example 14

By the same procedures as described in Test Example 13, an organic EL device was manufactured except the electron transport layer 5 was formed by vacuum-depositing bis(2-methyl-8-quinolinolato)-4-phenylphenolato-aluminum (BAlq) into a thickness of 5 nm and then vacuum-depositing Alq$_3$ into a thickness of 45 nm instead of the electron transport layer 5 in Test Example 13.

The thus-manufactured EL device exhibited a voltage of 9.0 V and a current efficiency of 26.7 cd/A at a current density of 20 mA/cm$^2$.

Test Example 15

By the same procedures as described in Test Example 1, an organic EL device was manufactured except the electron transport layer 5 was formed by vacuum-depositing 2-[3,5-bis(2,2':6',2''-terpyridin-4'-yl)phenyl]-4,6-diphenyl-1,3,5-triazine, synthesized in Experiment Example 44, into a thickness of 20 nm instead of the electron transport layer 5 in Test Example 1.

The thus-manufactured EL device exhibited a voltage of 5.5 V, a luminance of 2,230 cd/m$^2$, a current efficiency of 11.2 cd/A and a power efficiency of 6.4 lm/W. Luminance half-life of the device was 113 hours.

Test Example 16

By the same procedures as described in Test Example 15, an organic EL device having a multilayer structure as illustrated in FIG. 1 was manufactured by forming the hole injection layer 2, the hole transport layer 3, the emitting layer 4, the electron transport layer 5 and a cathode layer 6 in this order on the glass substrate 1, wherein the hole injection layer 2, the hole transport layer 3, the emitting layer 4 and the electron transport layer 5 were formed as follows. All other conditions and procedures remained the same.

The hole injection layer 2 was formed by vacuum-depositing phtalocyanine copper(II), previously purified by sublimation, into a thickness of 10 nm. The hole transport layer 3 was formed by vacuum-depositing N,N'-di(1-naphthyl)-N,N'-diphenylbenzidine (NPD) into a thickness of 30 nm.

The emitting layer 4 was formed by vacuum-depositing into a thickness of 30 nm a mixture of 4,4'-bis(9-carbazolyl)biphenyl (CBP) and tris(2-phenylpyridine)iridium(III) (Ir(ppy)$_3$) at a ratio of 94:6 by weight. The electron transport layer 5 was formed by vacuum-depositing 2-[3,5-bis(2,2':6',2''-terpyridin-4'-yl)phenyl]-4,6-diphenyl-1,3,5-triazine, synthesized in Experiment Example 44 according to the present invention, into a thickness of 50 nm.

The thus-manufactured EL device exhibited a voltage of 8.4 V, a luminance of 4,030 cd/m$^2$, a current efficiency of 20.2 cd/A, and a power efficiency of 7.5 lm/W. Luminance half-life of the device was 82 hours.

Test Example 17

By the same procedures as described in Test Example 15, an organic EL device was manufactured except the electron transport layer 5 was formed by vacuum-depositing a conventional electron transport material, Alq, into a thickness of 20 nm instead of the electron transport layer 5 in Test Example 15.

The thus-manufactured EL device exhibited a voltage of 7.2 V, a luminance of 1,859 cd/m$^2$, a current efficiency of 9.3 cd/A and a power efficiency of 4.0 lm/W. Luminance half-life of the device was 83 hours.

Test Example 18

By the same procedures as described in Test Example 16, an organic EL device was manufactured except the electron transport layer 5 was formed by vacuum-depositing a conventional electron transport material, Alq, into a thickness of 50 nm instead of the electron transport layer 5 with a thickness of 20 nm in Test Example 16.

The thus-manufactured EL device exhibited a voltage of 10.4 V, a luminance of 3,450 cd/m$^2$, a current efficiency of 17.3 cd/A and a power efficiency of 5.2 lm/W. Luminance half-life of the device was 108 hours.

Test Example 19

In this example, a mobility measuring element was manufactured and evaluated.

A glass substrate having an indium-tin oxide (ITO) transparent electrode was prepared, which had a stripe pattern comprised of ITO films with a 2 mm width. The glass substrate was washed with isopropyl alcohol and then surface-treated by irradiation of ultraviolet rays. A mobility-determining organic material was vacuum-deposited on the surface-treated substrate as described in detail below.

The glass substrate was placed in a vacuum deposition chamber, and its inner pressure was reduced to $3.6 \times 10^{-6}$ Torr, and 2-[3,5-di(1-pyrenyl)phenyl]-4,6-diphenyl-1,3,5-triazine was vacuum-deposited on the substrate at a deposition rate of 3 to 5 angstrom/sec by electrical resistance heating. The thus-formed thin film had a thickness of 1.8 μm as measured by stylus profilometer (DEKTAK).

A metal mask was arranged so as to be orthogonal to the ITO stripe, and an aluminum thin film with a width of 2 mm and a thickness of 100 nm was formed by vacuum deposition. Thus, a working area with 2 mm square for measuring mobility was formed. The substrate having the working area was encapsulated with ultraviolet ray-curable epoxy resin (available from Nagase Chemtex Corporation). The encapsulation was conducted in a nitrogen atmosphere having an oxygen-and-moisture content of below 1 ppm within a glove box.

The measurement of mobility using the above-mentioned mobility measuring element will be described.

The mobility of charge transport material can be measured by various methods, but, a generally adopted time-of-flight mobility measuring method was used. The measurement of mobility was made by determining the rate of transfer to the Al electrode, of charge generated upon irradiation of nitrogen laser from the transparent ITO electrode side. The measurement was made at room temperature using a mobility measuring apparatus available from Optel Co., Ltd., Japan.

The mobility of 2-[3,5-di(1-pyrenyl)phenyl]-4,6-diphenyl-1,3,5-triazine was $7.6 \times 10^{-5}$ cm$^2$/V·sec. This mobility value was higher than that ($1 \times 10^{-6}$ cm$^2$/V·sec) of hydroxyquinoline aluminum complex (Alq) which is the conventional electron transport material described in JP 2002-158091 A.

Test Example 20

By the same method as mentioned in Test Example 19, mobility of 2-[3,5-di(9-phenanthryl)phenyl]-4,6-di-p-tolyl-1,3,5-triazine was measured. The mobility was $2.4 \times 10^{-5}$ cm$^2$/V·sec.

Test Example 21

By the same method as mentioned in Test Example 19, mobility of 2-[3,5-di(1-pyrenyl)phenyl]-4,6-di-p-tolyl-1,3,5-triazine was measured. The mobility was $6.0 \times 10^{-5}$ cm$^2$/V·sec.

Test Example 22

By the same method as mentioned in Test Example 19, mobility of 2-[3,5-di(9-anthryl)phenyl]-4,6-diphenyl-1,3,5-triazine was measured. The mobility was $2.9 \times 10^{-4}$ cm$^2$/V·sec.

Test Example 23

Measurement of melting point and Tg of cyclic azine derivatives according to the present invention showed that the melting point and Tg were higher than those of an azine derivative A, represented by the following formula, and described in JP 2008-280330 A. The melting point and Tg of cyclic azine derivatives according to the present invention and the azine derivative A are shown in Table 1, below.

TABLE 1

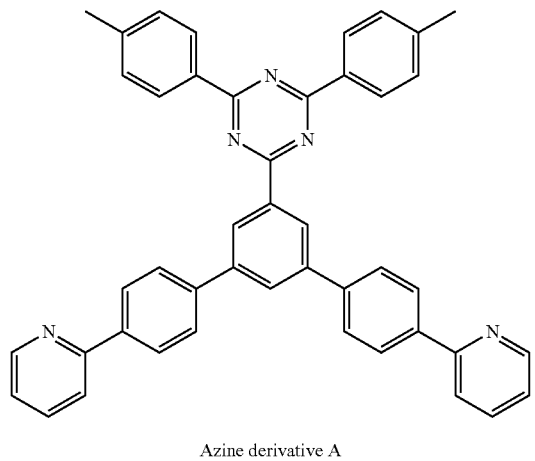 [SMILES: Cc1ccc(-c2nc(-c3ccc(C)cc3)nc(-c3cc(-c4ccc(-c5ccccn5)cc4)cc(-c4ccc(-c5ccccn5)cc4)c3)n2)cc1]

Azine derivative A

|  | Melting point (° C.) | Tg (° C.) |
|---|---|---|
| Example 54 | 357 | 147 |
| Example 55 | 407 | 142 |
| Example 56 | 340 | 155 |
| Example 57 | 325 | 156 |
| Example 58 | 388 | — |
| Example 59 | 340 | 160 |
| Azine derivative A | 279 | 108 |

As seen from the above-mentioned working examples, it was confirmed that the cyclic azine derivatives according to the present invention give fluorescent or phosphorescent EL devices which are drivable at a low power consumption and exhibit a prolonged life. The cyclic azine derivative of the present invention suitable not only as a material for the emitting layer in an organic EL devices as specifically described in the above Test Examples, but also as a material for other fluorescent or phosphorescent EL devices and for coated EL devices.

The organic EL devices of the present invention can be applied broadly to fields including flat panel displays, and lighting equipments to which low power consumption and long life are required.

INDUSTRIAL APPLICABILITY

The cyclic azine compound having the novel chemical structure according to the present invention is suitable as an organic compound layer of fluorescent or phosphorescent EL devices. Especially when the cyclic azine compound is used for an electron transport layer, the fluorescent or phosphorescent EL devices exhibit improved derivability at a low power consumption and enhanced light emission at high efficiency.

More specifically, thin films of the cyclic azine compound according to the present invention has outstanding properties in surface smoothness, amorphousness, heat resistance, electron transportability, hole blocking capability, resistance to oxidation and reduction, moisture resistance, oxygen resistance and electron injection property. Therefore, said film is useful as a material for an organic EL device, especially as a material for an electron transport layer, a hole blocking layer and a light emitting host layer of an organic EL device. The cyclic azine compound according to the present invention is also a wide band-gap compound, therefore, it is suitable for not only fluorescent EL devices but also phosphorescent EL devices.

The invention claimed is:

1. A cyclic azine compound represented by the formula (1)

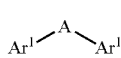

(1)

wherein, in the formula (1), each Ar$^1$ represents a phenyl, naphthyl or pyridyl group which are unsubstituted or substituted by an alkyl group having 1 to 4 carbon atoms, a phenyl group or a pyridyl group; and A represents a group selected from the group consisting of those which are represented by the following formulae (3) to (5):

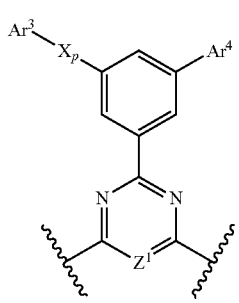

(3)

wherein, in the formula (3), Ar$^3$ represents a phenyl group, a pyridyl group or a pyrimidyl group; Ar$^4$ represents an anthryl group which is unsubstituted or substituted by an alkyl group having 1 to 4 carbon atoms or a phenyl group, a phenanthryl group which is unsubstituted or substituted by an alkyl group having 1 to 4 carbon atoms or a phenyl group, a fluorenyl group which is unsubstituted or substituted by an alkyl group having 1 to 4 carbon atoms or a phenyl group, a benzofluorenyl group which is unsubstituted or substituted by an alkyl group having 1 to 4 carbon atoms or a phenyl group, an unsubstituted pyrenyl group, an unsubstituted triphenylenyl group; X represents a phenylene group or a pyridylene group; p represents an integer of 0 to 2 provided that, when p is 2, the two Xs may be the same or different; and Z$^1$ represents a nitrogen atom;

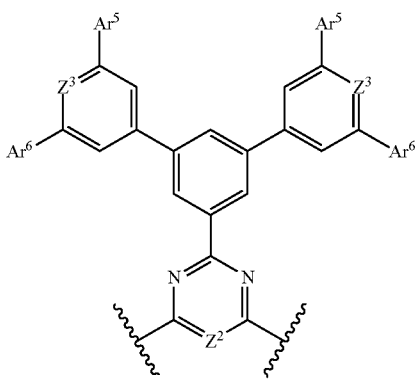

(4)

wherein, in the formula (4), each Ar$^5$ represents a pyridyl group, and each Ar$^6$ represent a phenyl group or a pyridyl group; Z$^2$ represents a nitrogen atom and each Z$^3$ represents a carbon atom or a nitrogen atom,

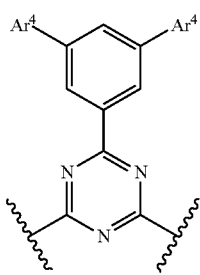

(5)

wherein, in the formula (5), each Ar$^4$ independently represents an anthryl group which is unsubstituted or substituted by an alkyl group having 1 to 4 carbon atoms or a phenyl group, a phenanthryl group which is unsubstituted or substituted by an alkyl group having 1 to 4 carbon atoms or a phenyl group, a fluorenyl group which is unsubstituted or substituted by an alkyl group having 1 to 4 carbon atoms or a phenyl group, a benzofluorenyl group which is unsubstituted or substituted by an alkyl group having 1 to 4 carbon atoms or a phenyl group, an unsubstituted pyrenyl group, an unsubstituted triphenylenyl group.

2. The cyclic azine compound according to claim 1, wherein each Ar$^4$ in the formula (5) represents an anthryl group which is unsubstituted or substituted by an alkyl group having 1 to 4 carbon atoms or a phenyl group, a phenanthryl group which is unsubstituted or substituted by an alkyl group having 1 to 4 carbon atoms or a phenyl group, a fluorenyl group which is unsubstituted or substituted by an alkyl group having 1 to 4 carbon atoms or a phenyl group, an unsubstituted pyrenyl group, or an unsubstituted triphenylenyl group.

3. A process for preparing a cyclic azine compound represented by the formula (1b):

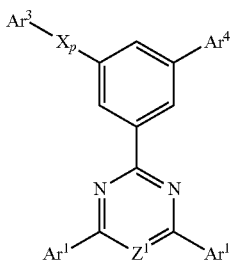

(1b)

wherein, in the formula (1b), each Ar$^1$ represents a phenyl, naphthyl or pyridyl group which are unsubstituted or substituted by an alkyl group having 1 to 4 carbon atoms, a phenyl group or a pyridyl group; Ar$^3$ represents a phenyl group, a pyridyl group or a pyrimidyl group; Ar$^4$ represents an anthryl group which is unsubstituted or substituted by an alkyl group having 1 to 4 carbon atoms or a phenyl group, a phenanthryl group which is unsubstituted or substituted by an alkyl group having 1 to 4 carbon atoms or a phenyl group, a fluorenyl group which is unsubstituted or substituted by an alkyl group having 1 to 4 carbon atoms or a phenyl group, a benzofluorenyl group which is unsubstituted or substituted by an alkyl group having 1 to 4 carbon atoms or a phenyl group, an unsubstituted pyrenyl group, an unsubstituted triphenylenyl group; X represents a phenylene group or a pyridylene group; p represents an integer of 0 to 2 provided that, when p is 2, the two Xs may be the same or different; and Z$^1$ represents a nitrogen atom; characterized by coupling a compound represented by the formula (10) with a compound represented by the formula (11) in the presence of a palladium catalyst and in the presence or absence of a base;

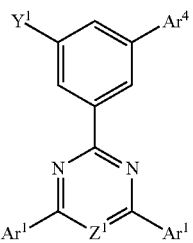

(10)

wherein, in the formula (10), each Ar$^1$ is the same as defined above; Ar$^4$ is the same as defined above; Z$^1$ represents a nitrogen atom; and Y$^1$ represents a chlorine, bromine or iodine atom;

Ar$^3$-Xp-M (11)

wherein, in the formula (11), Ar$^3$ represents a phenyl group, a pyridyl group or a pyrimidyl group; X represents a phenylene group or a pyridylene group; p represents an integer of 0 to 2 provided that, when p is 2, the two Xs may be the same or different; and M represents a metal group or a hetero atom group.

4. A process for preparing a cyclic azine compound represented by the formula (1c):

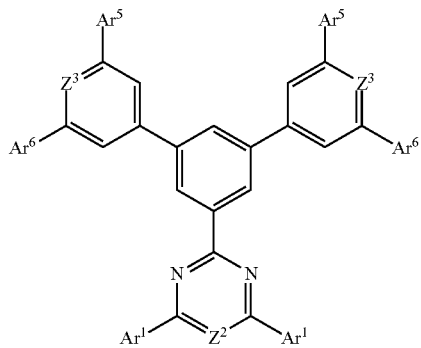

(1c)

wherein, in the formula (1c), each Ar$^1$ represents a phenyl, naphthyl or pyridyl group which are unsubstituted or substituted by an alkyl group having 1 to 4 carbon atoms, a phenyl group or a pyridyl group; each Ar$^5$ represents a pyridyl group, and each Ar$^6$ represent a phenyl group or a pyridyl group; and Z$^2$ represents a nitrogen atom and each Z$^3$ represents a carbon or nitrogen atom; characterized by coupling a compound represented by the formula (12) with a compound represented by the formula (13) in the presence of a palladium catalyst and a base;

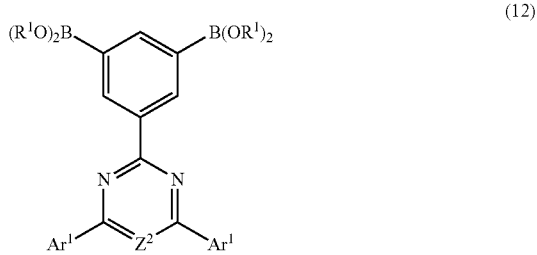

(12)

wherein, in the formula (12), each $Ar^1$ is the same as defined above; $Z^2$ represents a nitrogen atom; each $R^1$ represents a hydrogen atom, an alkyl group having 1 to 4 carbon atoms or a phenyl group; and groups $R^1$ in the two —$B(OR^1)_2$ groups may be the same or different, and two groups $R^1$ in each of the two —$B(OR^1)_2$ groups may form a ring together with the oxygen atoms and the boron atom;

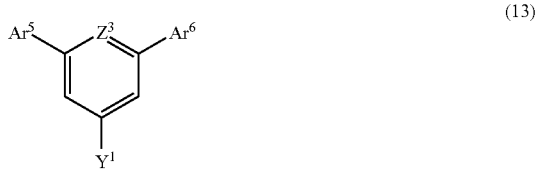

(13)

wherein, in the formula (13), $Ar^5$ is the same as defined above, and $Ar^6$ is the same as defined above; and $Z^3$ represents a carbon or nitrogen atom; and $Y^1$ represents a chlorine, bromine or iodine atom.

5. A process for preparing a cyclic azine compound represented by the formula (1d):

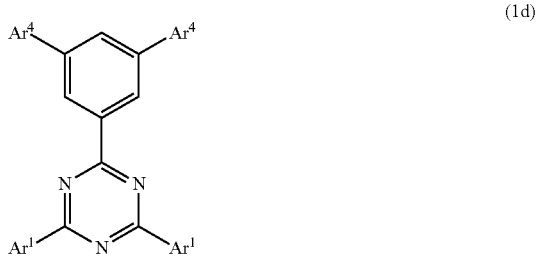

(1d)

wherein, in the formula (1d), each $Ar^1$ represents an aromatic group, which is unsubstituted or substituted by an alkyl group having 1 to 4 carbon atoms, a phenyl group or a pyridyl group;

and each $Ar^4$ independently represents an unsubstituted or substituted aromatic hydrocarbon group having 2 to 4 rings; characterized by coupling a compound represented by the formula (14) with a compound represented by the formula (15) in the presence of a palladium catalyst and a base;

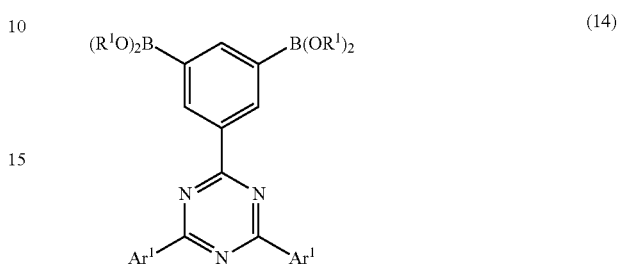

(14)

wherein, in the formula (14), each $Ar^1$ represents a phenyl, naphthyl or pyridyl group which are unsubstituted or substituted by an alkyl group having 1 to 4 carbon atoms, a phenyl group or a pyridyl group; each $R^1$ represents a hydrogen atom, an alkyl group having 1 to 4 carbon atoms or a phenyl group; and groups $R^1$ in the two $B(OR^1)_2$ groups may be the same or different, and two groups $R^1$ in each of the two —$B(OR^1)_2$ groups may form a ring together with the oxygen atoms and the boron atom;

$Ar^4Y^1$ (15)

wherein, in the formula (15), $Ar^4$ represents an anthryl group which is unsubstituted or substituted by an alkyl group having 1 to 4 carbon atoms or a phenyl group, a phenanthryl group which is unsubstituted or substituted by an alkyl group having 1 to 4 carbon atoms or a phenyl group, a fluorenyl group which is unsubstituted or substituted by an alkyl group having 1 to 4 carbon atoms or a phenyl group, a benzofluorenyl group which is unsubstituted or substituted by an alkyl group having 1 to 4 carbon atoms or a phenyl group, an unsubstituted pyrenyl group, an unsubstituted triphenylenyl group; and $Y^1$ represents a chlorine, bromine or iodine atom.

6. An organic electroluminescent device comprising as a constituent a cyclic azine compound represented by the formula (1):

(1)

wherein, in the formula (1), each $Ar^1$ represents an aromatic group, which is unsubstituted or substituted by an alkyl group having 1 to 4 carbon atoms, a phenyl group or a pyridyl group; and A represents a group selected from the group consisting of those which are represented by the following formulae (3) to (5):

(3)

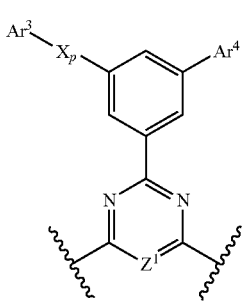

wherein, in the formula (3), Ar³ represents a phenyl group, a pyridyl group or a pyrimidyl group; Ar⁴ represents an anthryl group which is unsubstituted or substituted by an alkyl group having 1 to 4 carbon atoms or a phenyl group, a phenanthryl group which is unsubstituted or substituted by an alkyl group having 1 to 4 carbon atoms or a phenyl group, a fluorenyl group which is unsubstituted or substituted by an alkyl group having 1 to 4 carbon atoms or a phenyl group, a benzofluorenyl group which is unsubstituted or substituted by an alkyl group having 1 to 4 carbon atoms or a phenyl group, an unsubstituted pyrenyl group, an unsubstituted triphenylenyl group; X represents a phenylene group or a pyridylene group; p represents an integer of 0 to 2 provided that, when p is 2, the two Xs may be the same or different; and $Z^1$ represents a nitrogen atom;

(4)

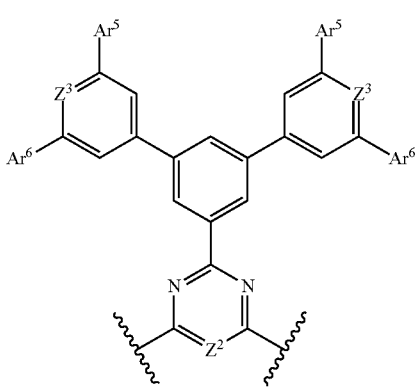

wherein, in the formula (4), each Ar⁵ represents a pyridyl group, and each Ar⁶ represent a phenyl group or a pyridyl group; $Z^2$ represents a nitrogen atom and each $Z^3$ represents a carbon atom or a nitrogen atom; and (5)

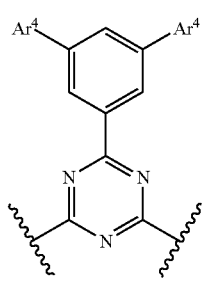

wherein, in the formula (5), each Ar⁴ is the same as defined above.

7. The process for preparing a cyclic azine compound according to claim 3, wherein the palladium catalyst has a tertiary phosphine as a ligand.

8. The process for preparing a cyclic azine compound according to claim 4, wherein the palladium catalyst has a tertiary phosphine as a ligand.

9. The process for preparing a cyclic azine compound according to 5, wherein the palladium catalyst has a tertiary phosphine as a ligand.

10. The process for preparing a cyclic azine compound according to claim 3, wherein the metal group or the hetero atom group, represented by M in the formulae (7) and (11), is a group represented by the following formula:

—B(OR¹)₂ or —ZnR² wherein R¹ represents a hydrogen atom, an alkyl group having 1 to 4 carbon atoms or a phenyl group; two groups R¹ in the group —B(OR¹)₂ may be the same or different and the two groups R¹ in the group —B(OR¹)₂ may form a ring together with the oxygen atoms and the boron atom; and R² represents a halogen atom.

* * * * *

UNITED STATES PATENT AND TRADEMARK OFFICE
CERTIFICATE OF CORRECTION

PATENT NO. : 9,120,773 B2
APPLICATION NO. : 13/391046
DATED : September 1, 2015
INVENTOR(S) : Aihara et al.

Page 1 of 1

It is certified that error appears in the above-identified patent and that said Letters Patent is hereby corrected as shown below:

In the Claims

Column 142, line 35 (claim 5, line 21) please change "$Ar^4Y^1$" to -- $Ar^4-Y^1$ --
Column 143, line 13 (claim 6, line 10) please change "$Ar^a$" to -- $Ar^3$ --

Signed and Sealed this
Tenth Day of May, 2016

Michelle K. Lee
*Director of the United States Patent and Trademark Office*